US011058762B2

(12) United States Patent
Geall et al.

(10) Patent No.: US 11,058,762 B2
(45) **Date of Patent: *Jul. 13, 2021**

(54) IMMUNOGENIC COMPOSITIONS AND USES THEREOF

(75) Inventors: Andrew Geall, Littleton, MA (US); Gillis Otten, Rowley, MA (US); Susan Barnett, San Francisco, CA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/130,869

(22) PCT Filed: Jul. 6, 2012

(86) PCT No.: PCT/US2012/045854

§ 371 (c)(1), (2), (4) Date: Apr. 15, 2014

(87) PCT Pub. No.: WO2013/006842

PCT Pub. Date: Jan. 10, 2013

(65) Prior Publication Data

US 2014/0242152 A1 Aug. 28, 2014

Related U.S. Application Data

(60) Provisional application No. 61/505,105, filed on Jul. 6, 2011.

(51) Int. Cl.

| | |
|---|---|
| ***A61K 39/155*** | (2006.01) |
| ***A61K 39/245*** | (2006.01) |
| ***A61K 39/12*** | (2006.01) |
| ***A61P 31/20*** | (2006.01) |
| ***A61P 31/14*** | (2006.01) |
| ***A61K 39/00*** | (2006.01) |

(52) U.S. Cl.

CPC ............ *A61K 39/155* (2013.01); *A61K 39/12* (2013.01); *A61K 39/245* (2013.01); *A61P 31/14* (2018.01); *A61P 31/20* (2018.01); *A61K 2039/53* (2013.01); *A61K 2039/545* (2013.01); *A61K 2039/55505* (2013.01); *A61K 2039/55555* (2013.01); *A61K 2039/55566* (2013.01); *A61K 2039/55588* (2013.01); *C12N 2710/16134* (2013.01); *C12N 2760/18534* (2013.01); *C12N 2770/36143* (2013.01)

(58) Field of Classification Search

None

See application file for complete search history.

(56) References Cited

U.S. PATENT DOCUMENTS

| | | | |
|---|---|---|---|
| 7,604,803 | B2 | 10/2009 | Bacon et al. |
| 7,862,829 | B2 | 1/2011 | Johnston et al. |
| 10,487,332 | B2 | 11/2019 | Geall |

FOREIGN PATENT DOCUMENTS

| | | | | |
|---|---|---|---|---|
| EP | 0 880 360 | B1 * | 10/2002 | ............ A61K 39/00 |
| JP | 2000505802 | A | 5/2000 | |
| WO | 97/28818 | A1 | 8/1997 | |
| WO | 99/30733 | A1 | 6/1999 | |
| WO | 2002/09645 | A2 | 2/2002 | |
| WO | 2005/007689 | A1 | 1/2005 | |
| WO | 2006/061643 | A1 | 6/2006 | |
| WO | 2009/042794 | A2 | 4/2009 | |
| WO | 2009/074861 | A2 | 6/2009 | |
| WO | 2009/156852 | A1 | 6/2009 | |
| WO | 2010/036948 | A2 | 4/2010 | |
| WO | 2011/005799 | A2 | 1/2011 | |
| WO | 2011/127316 | A1 | 10/2011 | |
| WO | WO 2012/006369 | A2 | 1/2012 | |
| WO | 2012/030901 | A1 | 3/2012 | |

OTHER PUBLICATIONS

Elkington et al., "Ex Vivo Profiling of CD8+ -T-Cell Responses to Human Cytomegalovirus Reveals Broad and Multispecific Reactivities in Healthy Virus Carriers" 77(9) Journal of Virology 6226-5240 (2003).*

Frolov et al., "Alphavirus-based expression vectors: Strategies and applications" 93 Proceedings of the National Academy of Sciences USA (1996).*

Tubulekas et al., "Alphavirus expression vectors and their use as recombinant vaccines: a minireview" 190 Gene 191-195 (1997).*

Sawai et al., "A Novel Method of Cell-Specific mRNA Transfection" 64 Molecular Genetics and Metabolism 44-51 (1998).*

Xu et al., "Characterization of immune Responses Elicited in Macaques Immunized Sequentially with Chimeric VEE/SIN Alphavirus Replicon Particles Expressing SIVGag and/or HIVEnv and with Recombinant HIVgp140Env Protein," Aids Research and Human Retroviruses, Mary Ann Liebert, 22(10):1022-1030 (2006).

Barnett et al., "Antibody-Mediated Protection against Mucosal Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).

Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).

(Continued)

*Primary Examiner* — Nancy J Leith

(74) *Attorney, Agent, or Firm* — Birch, Stewart, Kolasch & Birch, LLP

(57) ABSTRACT

This invention generally relates to immunogenic compositions that comprise an RNA component and a polypeptide component. Immunogenic compositions that deliver antigenic epitopes in two different forms—a first epitope from a pathogen, in RNA-coded form; and a second epitope from the same pathogen, in polypeptide form—are effective in inducing immune response to the pathogen. The invention also relates to a kit comprising an RNA-based priming composition and a polypeptide-based boosting composition. The kit may be used for sequential administration of the priming and the boosting compositions.

21 Claims, 13 Drawing Sheets

Specification includes a Sequence Listing.

(56) References Cited

OTHER PUBLICATIONS

Anderson et al. "Incorporation of pseudouridine into mRNA enhances translation by diminishing PKR activation," Nucleic Acids Research, 38(17):5884-5892 (2010).
Defang et al., "Induction of neutralizing antibodies to Hendra and Nipah glycoproteins using a Venezuelan equine encephalitis virus in vivo expression system," Vaccine Elsevier Ltd. GB, 29(2):212-220 (2010).
Genini et al., "Serum antibody response to the gH/gL/pUL128-131 five protein complex of Serum antibody response to the gH/gL/pUL128-131 five-protein complex of human cytomegalovirus (HCMV) in primary and reactivated HCMV infections," Journal of Clinical Virology, 52:113-118 (2011).
Graham, Barney, "Biological challenges and technological opportunities for respiratory syncytial virus vaccine development," Immunological Reviews, 239(1):149-166 (2011).
Hidmark et al.,"Humoral Responses against Coimmunized Protein Antigen but Not against Alphavirus-Encoded Antigens Require Alpha/Beta Interferon Signaling," Journal of Virology, 80(14):7100-7110 (2006).
NäSlund et al., "Role of innate signalling pathways in the immunogenicity of alphaviral replicon-based vaccines," Virology Journal, 8(1):36 (2011).
Van Bleek et al., "RSV 2010: Recent advances in research on respiratory syncytial virus and other pneumoviruses," Vaccine, 29(43):7285-7291 (2011).
Carine et al., "Vaccination of calves using the BRSV nucleocapsid protein in a DNA prime-protein boost strategy stimulates cell-mediated immunity and protects the lungs against BRSV replication and pathology," Vaccine Elsevier Ltd, GB, 26(37):4840-4848 (2008).
Saccoccio, Frances Maria, "Thesis: CMV Vaccine Development based on Epithelial Entry Mediators UL128, UL130, and UL131," Jun. 3, 2011, Retrieved from the Internet: URL:https//digarchive.library.vcu.edu/bitstreamjhandle/10156/3452/SACCOCCIO FRANCES PhD.pdf?sequence=1-1retrieved on Mar. 18, 20148] Impact on future vaccine design; p. 160 (2011). Chapter: Peptides to UL130 and UL131. Neutralize CMV Infection of Mucosal Epithelial Cells; p. 96.
Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier Ltd, GB, 25(41):7132-7144, (2007).
Thompson et al., "Mucosal and systemic adjuvant activity of alphavirus replicon particles," Proceedings of the National Academy of Sciences,103(10):3722-3727 (2006).
Reap et al., Development and preclinical evaluation of an alphavirus replicon particle vaccine for cytomegalovirus, Vaccine, Elsevier Ltd, GB, 25(42):7441-7449, (2007).
Bernstein et al., "Randomized, double-blind, Phase 1 trial of an alphavirus replicon vaccine for cytomegalovirus in CMV seronegative adult volunteers," Vaccine, 28:484-493 (2010).
International Search Report for International Application No. PCT/US2012/045854 dated May 9, 2014.
Lee, John S., et al., "Multiagent vaccines vectored by Venezuelan, equine encephalitis virus replicon elicits immune responses to Marburg virus and protection against anthrax and botulinum neurotoxin in mice," Vaccine, Elsevier, Amsterdam, NL, vol. 24, No. 47-48; pp. 6886-6892; Nov. 17, 2006.
Xu et al., "Sequential priming and boosting with heterologous HIV immunogens predominantly stimulated T cell immunity against conserved epitopes," AIDS; 20(18); 2293-2303; Nov. 28, 2006.
Zhu, W., et al. "Vaccines for Gonorrhea: Can We Rise to the Challenge?", Frontiers in Microbiology, vol. 2, Jan. 1, 2011.
Jeffs et al., "A Scalable, Extrusion-Free Method for Efficient Liposomal Encapsulation of Plasmid DNA," Pharmaceutical Research (Mar. 2005), vol. 22, No. 3, pp. 362-372.

* cited by examiner

IMMUNOGENIC COMPOSITIONS AND USES THEREOF

RELATED APPLICATION

This application is a U.S. National Phase of International Application No. PCT/US2012/045854, filed Jul. 6, 2012 and published in English, which claims the benefit of U.S. Provisional Application No. 61/505,105 filed on Jul. 6, 2011; the entire contents of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 5, 2012, is named PAT54514.txt and is 92,631 bytes in size.

BACKGROUND OF THE INVENTION

Nucleic acid based vaccines are an attractive approach to vaccination. For example, intramuscular (IM) immunization of plasmid DNA encoding an antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype. DNA vaccines are generally effective in generating cell mediated immunity (such as interferon-γ secreting antigen-specific T-cells and antigen-specific cytotoxic T-cells), but less effective in generating antibodies against the encoded and expressed antigen.

WO 99/30733 discloses a method of enhancing immune response to a nucleic acid vaccine by simultaneous administration of the protein that is encoded by the nucleic acid. The two components do not need to be administered in the same composition. Both components need to be administered during the induction phase of the immune response, with the protein preferably being masked or held back until after the nucleic acid has primed the immune system. In some examples, the vaccine comprised naked DNA and naked protein antigen in physical admixture. In others examples, the protein antigen was formulated for delayed release in a biodegradable polymer-alum formulation admixed with naked DNA.

WO 97/28818 discloses a vaccine that delivers a nucleic acid and a protein antigen to antigen presenting cells. The nucleic acid may encode the same protein as the protein antigen. The nucleic acid and protein are "complexed," e.g., by covalent conjugation. The complex may be formulated as a synthetic virus-like particle. It is also suggested that liposomal systems may be used.

U.S. Pat. No. 7,604,803 discloses the co-delivery of nucleic acid and its encoded protein to the same cell using a liposomal system. The DNA molecule and its encoded protein are entrapped within the same liposomal vehicle, such that the two entities arrive at antigen-presenting cells together, resulting in the processing and presentation of the protein form of the antigen, together with the expression of the DNA-encoded form of the antigen in the same cell.

WO 2009/156852 discloses a prime/boost approach to raise an immune response in a subject. The method comprises: (i) administering at least one dose of a priming immunogenic composition to the subject, to elicit a primary immune response against a pathogen; and (ii) administering a boosting immunogenic composition to the subject, to elicit, within 21 days of its administration or sooner, a protective anamnestic immune response against the pathogen.

WO 2009/074861 discloses a vaccine comprising (i) a nucleic acid sequence encoding at least one influenza virus antigen coated onto carrier particles, and (ii) an assistor protein for sequential or concomitant administration. The assistor protein and the antigen encoded by the nucleic acid molecule share at least one common epitope.

WO 2006/061643 discloses a prime-boost vaccination method using herpes viral vectors, in particular, a heterologous prime-boost regimen using two different non-replicating viral vectors, one of which is a herpes virus vector. The two vectors share a common epitope that is associated with a target antigen or disease.

WO 2010/036948 discloses the use of a priming composition and a boosting composition to prime and boost an immune response. The priming composition comprises a DNA plasmid that comprises a nucleic acid molecule encoding an influenza virus hemagglutinin (HA) or an epitope-bearing domain thereof. The boosting composition comprises an influenza vaccine.

It is known that non-coding plasmid DNA has an immuno-adjuvant action when co-entrapped with peptides in liposomal vesicles (Gursel, M. et al. Vaccine (1999) 17: 1376-1383) and that DNA with CpG motifs has an adjuvant effect on naked DNA and peptide vaccines (Klinman, D. M. et al. Vaccine (1999) 17: 19-25).

Concerns have been raised regarding the safety of DNA-based vaccines. The introduced DNA molecules could potentially integrate into the host genome or, due to their distribution to various tissues, could lead to undesirable sustained expression of antigens. In addition, certain DNA viruses have also been used to deliver DNA molecules. Because of their infectious properties, such viruses achieve a very high transfection rate. The viruses used are genetically modified to prevent the formation of functional infectious particles in the transfected cell. Despite these precautions, however, it is not possible to rule out the risk of uncontrolled propagation of the introduced gene and viral genes, for example due to potential recombination events. This also entails the risk of the DNA being inserted into an intact gene of the host cell's genome by e.g. recombination, with the consequence that the host gene may be mutated and thus completely or partially inactivated or may give rise to misinformation. In other words, synthesis of a host gene product which is vital to the cell may be completely suppressed or, alternatively, a modified or incorrect gene product is expressed.

RNA molecules encoding an antigen or a derivative thereof may also be used as vaccines. RNA vaccines offer certain advantages as compared to DNA vaccines. However, compared with DNA-based vaccines, relatively minor attention has been given to RNA-based vaccines. RNAs are highly susceptible to degradation by nucleases when administered as a therapeutic or vaccine. Additionally, RNAs are not actively transported into cells. See, e.g., Vajdy, M., et al.,

*Mucosal adjuvants and delivery systems for protein-, DNA- and RNA-based vaccines*, Immunol Cell Biol, 2004. 82(6): p. 617-27.

Toll-like receptors (TLRs) are a group of pattern recognition receptors which bind to pathogen-associated molecular patterns (PAMPS) from bacteria, fungi, protozoa and viruses, and act as a first line of defense against invading pathogens. Many TLRs have been identified in humans, mice, and other mammalian species. DNA molecules (such as bacterial or viral DNA) are recognized by TLR9, whereas RNA molecules (such as single stranded viral RNA) are recognized by TLR7 or TLR8.

U.S. Pat. No. 7,862,829 discloses a method of producing an immune response by administering an antigen and an alphavirus-based adjuvant. The method is based on the discovery that alphavirus, a (+)ssRNA virus, can act as an adjuvant to enhance an immune response against an antigen, even though the antigen is not presented on or expressed by the virus. The alphavirus particles may be delivered by liposomal system.

There is a need to improve the efficacy of protein subunit vaccines and nucleic acid vaccines such as RNA vaccines.

SUMMARY OF THE INVENTION

Certain terms that are used to describe the invention in this are defined and explained herein in Section 6.

This invention generally relates to immunogenic compositions that comprise an RNA component and a polypeptide component Immunogenic compositions that deliver antigenic epitopes in two different forms—a first epitope from a pathogen, in RNA-coded form; and a second epitope from the same pathogen, in polypeptide form—can enhance the immune response to the pathogen, as compared to immunization with RNA alone, or polypeptide alone. Preferably, the first epitope and the second epitope are the same epitope.

The invention also relates to a kit comprising an RNA-based priming composition and a polypeptide-based boosting composition for sequential administration. The kit is suitable for, for example, a "RNA prime, protein boost" immunization regimen to generate an immune response to a pathogen.

The invention also relates to methods for treating or preventing an infectious disease, methods for inducing an immune response, or methods of vaccinating a subject, by co-delivery of an RNA molecule and a polypeptide molecule (co-administration).

The invention also relates to methods for treating or preventing an infectious disease, methods for inducing an immune response, or methods of vaccinating a subject, by sequential administration of an RNA molecule and a polypeptide molecule (prime-boost).

In one aspect, the invention provides an immunogenic composition comprising: (i) a self-replicating RNA molecule that encodes a first polypeptide antigen comprising a first epitope; and (ii) a second polypeptide antigen comprising a second epitope; wherein the first and second epitope are epitopes from the same pathogen. The first and and second epitopes can be the same epitope. The first and second epitopes can be different epitopes.

In some embodiments, the first polypeptide antigen and the second polypeptide antigen are substantially the same.

The first polypeptide antigen can be a soluble or membrane anchored polypeptide and the second polypeptide antigen can be a soluble polypeptide.

In some embodiments, the first polypeptide antigen is a fusion polypeptide that further comprises a third epitope from a different pathogen. In some embodiments, the second polypeptide antigen is a fusion polypeptide that further comprises a third epitope from a different pathogen. The first and second epitopes can be epitopes from the same subspecies of the pathogen.

The self-replicating RNA can be an alphavirus-derived RNA replicon. The self-replicating RNA molecule can comprise one or more modified nucleotides.

In some embodiments, the immunogenic composition further comprises a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, or a cationic nanoemulsion.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion or combinations thereof.

In some embodiments, the pathogen is a virus, and the first polypeptide antigen and second polypeptide antigen are viral antigens. The viral antigens can be RSV-F antigens. Preferably, the RSV-F antigens comprise an amino acid sequence selected from SEQ ID NOs:25-40.

The viral antigens can be from Cytomegalovirus (CMV). In some embodiments, the CMV antigens are independently selected from the group consisting of a gB antigen, a gH antigen, a gL antigen, a gM antigen, a gN antigen, a gO antigen, a UL128 antigen, a UL129 antigen, and a UL130 antigen.

In some embodiments, the immunogenic composition further comprises an adjuvant. The adjuvant can be MF59.

The invention also relates to pharmaceutical compositions that comprise an immunogenic composition as described herein and a pharmaceutically acceptable carrier and/or a pharmaceutically acceptable vehicle.

The invention also relates to methods for treating or preventing an infectious disease comprising administering to a subject in need thereof a therapeautically effective amount of a composition as described herein.

The invention also relates to methods of inducing an immune response in a subject comprising administering to a subject in need thereof a therapeutically effective amount of a composition as described herein.

The invention also relates to methods of vaccinating a subject, comprising administering to a subject in need thereof a composition as described herein.

The invention also relates to kits comprising: (i) a priming composition comprising a self-replicating RNA molecule that encodes a first polypeptide antigen that comprises a first epitope from a pathogen; and (ii) a boosting composition comprising a second polypeptide antigen that comprises a second epitope from the pathogen. The first and second polypeptide antigens can be substantially the same. The first polypeptide antigen can be a soluble or membrane anchored polypeptide, and the second polypeptide antigen can be a soluble polypeptide. The first polypeptide antigen can be a fusion polypeptide. The second polypeptide antigen can be a fusion polypeptide. The self-replicating RNA can be an alphavirus-derived RNA replicon. The self-replicating RNA molecule can comprise one or more modified nucleotides.

In some embodiments, the priming composition of the kit further comprises a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, or a cationic nanoemulsion.

In some embodiments, the RNA molecule of the kit is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion or combinations thereof.

In some embodiments, the pathogen of the kit is a virus, and the first polypeptide antigen and second polypeptide antigen are viral antigens. The viral antigens can be from respiratory syncytial virus (RSV). The viral antigens can be a RSV-F antigen. Preferably, the RSV-F antigens comprise an amino acid sequence selected from SEQ ID NOs:25-40.

In some embodiments, the viral antigens are from Cytomegalovirus (CMV). In some embodiments, the CMV antigens are independently selected from the group consisting of a gB antigen, a gH antigen, a gL antigen, a gM antigen, a gN antigen, a gO antigen, a UL128 antigen, a UL129 antigen, and a UL130 antigen.

In some embodiments, the priming composition of the kit, the boosting composition of the kit, or both, comprise an adjuvant. The adjuvant can be MF59. The priming composition, the boosting composition, or both can comprise a pharmaceutically acceptable carrier and/or a pharmaceutically acceptable vehicle.

The invention also relates to methods for treating or preventing an infectious disease comprising: (i) administering to a subject in need thereof at least once a therapeutically effective amount of a priming composition comprising a self-replicating RNA molecule that encodes a first polypeptide antigen that comprises a first epitope from a pathogen; and subsequently administering the subject at least once a therapeutically effective amount of a boosting composition comprising a second polypeptide antigen that comprises a second epitope from said pathogen; wherein said first epitope and second epitope are the same epitope.

The invention also relates to methods for inducing an immune response in a subject comprising (i) administering to a subject in need thereof at least once a therapeutically effective amount of a priming composition comprising a self-replicating RNA molecule that encodes a first polypeptide antigen that comprises a first epitope from a pathogen; and subsequently administering the subject at least once a therapeutically effective amount of a boosting composition comprising a second polypeptide antigen that comprises a second epitope from said pathogen; wherein said first epitope and second epitope are the same epitope.

The invention also relates to methods for vaccinating a subject, comprising administering to a subject in need thereof at least once a therapeutically effective amount of a priming composition comprising a self-replicating RNA molecule that encodes a first polypeptide antigen that comprises a first epitope from a pathogen; and subsequently administering the subject at least once a therapeutically effective amount of a boosting composition comprising a second polypeptide antigen that comprises a second epitope from said pathogen; wherein said first epitope and second epitope are the same epitope.

In some embodiments, the first polypeptide antigen and the second polypeptide antigen are substantially the same.

The first polypeptide antigen can be a soluble or membrane anchored polypeptide and the second polypeptide antigen can be a soluble polypeptide.

In some embodiments, the first polypeptide antigen is a fusion polypeptide that further comprises a third epitope from a different pathogen. In some embodiments, the second polypeptide antigen is a fusion polypeptide that further comprises a third epitope from a different pathogen. The first and second epitopes can be epitopes from the same subspecies of the pathogen.

The self-replicating RNA can be an alphavirus-derived RNA replicon. The self-replicating RNA molecule can comprise one or more modified nucleotides.

In some embodiments, the immunogenic composition further comprises a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, or a cationic nanoemulsion.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion or combinations thereof.

In some embodiments, the pathogen is a virus, and the first polypeptide antigen and second polypeptide antigen are viral antigens. The viral antigens can be RSV-F antigens. Preferably, the RSV-F antigens comprise an amino acid sequence selected from SEQ ID NOs:25-40.

The viral antigens can be from Cytomegalovirus (CMV). In some embodiments, the CMV antigens are independently selected from the group consisting of a gB antigen, a gH antigen, a gL antigen, a gM antigen, a gN antigen, a gO antigen, a UL128 antigen, a UL129 antigen, and a UL130 antigen.

In some embodiments, the immunogenic composition further comprises an adjuvant. The adjuvant can be MF59.

The invention also relates to pharmaceutical compositions that comprise an immunogenic composition as described herein and a pharmaceutically acceptable carrier and/or a pharmaceutically acceptable vehicle.

DETAILED DESCRIPTION OF THE INVENTION

1. Overview

Figure 1:
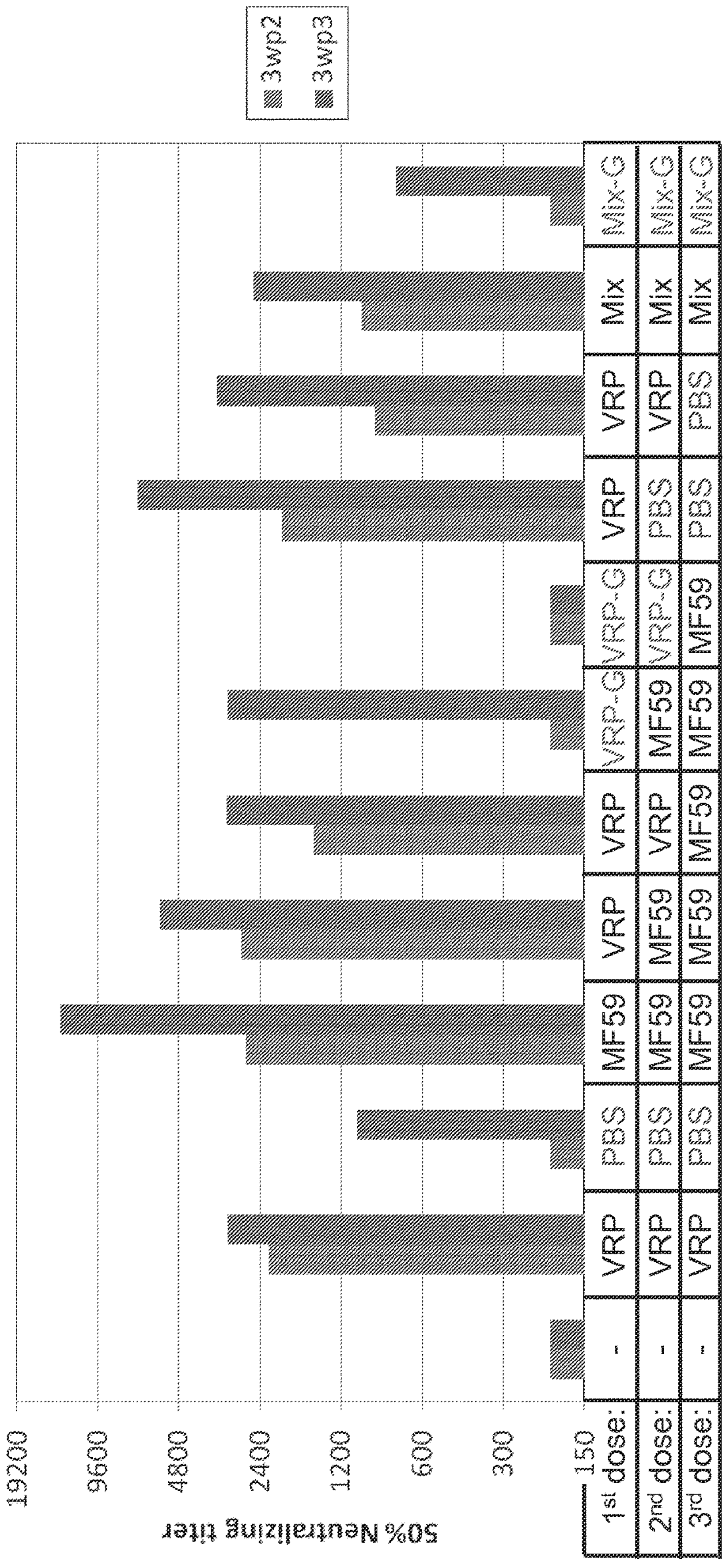
FIG. 1 is a graph showing neutralizing antibody tires elicited by a three dose immunization regimen in which VRPs that express gH/gL, VRP that express green fluorescent protein (VRP-G), and purified gH/gL administered that were administered in various orders or were mixed and coadministered. (see Example VI, Table VI-1) Key: VRP=gH/gL expressingVRP, VRP-G=green fluorescent protein expressing VRP, PBS=gHsol/gL subunit in PBS, MF59=gHsol/gL in MF59, Mix=gH/gL VRP+gHsol/gL (no adjuvant), Mix-G=VRP-G+gHsol/gL (no adjuvant).

One particular advantage of an RNA vaccine is that RNA molecules are self-adjuvanting. For example, the inventors observed that RNA molecules (formulated in liposomes) induced several serum cytokines, including IFN-α, IP-10 (CXCL-10), IL-6, KC (CXCL1), IL-5, IL-13, MCP-1, and MIP-α, within 24 hours of intramuscular injection into a mouse model. The cytokines can enhance the host immune response to the protein antigen that was encoded by the RNA molecule.

Vaccination strategies that combine an RNA molecule and a polypeptide molecule (e.g., administering an immunogenic composition that has an RNA component and a protein component; or sequential administration regimens such as "RNA prime, protein boost") provide several benefits. For example, the polypeptide molecule can enhance total antibody titers in the host, while the RNA molecule can enhance the production of antibodies that recognize an antigen in its native structure. Thus the combination can induce an antibody response with an enhanced ratio of functional antibodies (e.g., neutralizing antibodies) to total antibodies. Furthermore, RNA molecules promote type 1 T helper responses (Th1, IFN-$\gamma^{hi}$, IL-$4^{lo}$), whereas protein molecules promote type 2 T helper responses. Thus, combining an RNA molecule and a polypeptide molecule can promote both T cell-mediated immunity as well as humoral immunity. In addition, RNA molecules may be delivered to cells using delivery systems such as liposomes or oil-in-water emulsions. Liposomes and oil-in-water emulsions are also known to have adjuvant activities. Thus, the adjuvant activity of the RNA together with adjuvant activity of the delivery system can act synergistically to enhance the immune response to an antigen. Finally, multivalency may be achieved by combining a polypeptide antigen with an RNA that encodes a different antigen from the same pathogen.

(A) Co-Administration of an RNA Molecule and a Polypeptide Molecule

In one aspect, the invention relates to immunogenic compositions that comprise an RNA component and a polypeptide component Immunogenic compositions that deliver antigenic epitopes in two different forms—a first epitope from a pathogen, in RNA-coded form; and a second epitope from the same pathogen, in polypeptide form—can enhance the immune response to the pathogen.

Preferably, the first epitope and the second epitope are the same epitope (i.e., the first antigen, in RNA-coded form, and the second antigen, in polypeptide form, share at least one common epitope). For example, the RNA component of the immunogenic composition can encode a protein that is substantially the same as the polypeptide component of the immunogenic composition (e.g., the amino acid sequence encoded by the RNA molecule and the polypeptide component of the immunogenic composition share at least about 90% sequence identity across the length of the shorter antigen). Alternatively, the two antigens have the same epitope, such as the same immunodominant epitope(s).

As described herein, the inventors have evaluated the efficacies of immunogenic compositions that comprise (i) a self-replicating RNA molecule that encodes a viral antigen, and (ii) the viral antigen in polypeptide form. Viral antigens that were used in these studies include HIV gp140 and RSV-F antigens. The results demonstrated that co-administering an RNA molecule that encodes a viral antigen, together with the viral antigen in polypeptide form, potentiated the immune response to the antigen, resulting in higher antibody titers as compared to administering the RNA molecule alone. In addition, co-administering a viral antigen in RNA-coded form and in polypeptide form enhanced isotype switching from $IgG_1$ to $IgG_{2a}$, producing a more balanced $IgG_1$:$IgG_{2a}$ subtype profile as compared to administering the polypeptide antigen alone. Finally, the studies disclosed herein also show that administrating an antigen in RNA-coded form and polypeptide from can enhance CD4+ and CD8+ T cell-mediated immunity.

The immunogenic compositions described herein can be formulated as a vaccine to induce or enhance the host immune response to a pathogen. Also provided herein are methods of using the immunogenic compositions of the invention to induce or enhance an immune response in a subject in need thereof.

(B) Prime-Boost

In another aspect, the invention relates to a kit comprising: (i) a priming composition comprising a self-replicating RNA molecule that encodes a first polypeptide antigen that comprises a first epitope, and (ii) a boosting composition comprising a second polypeptide antigen that comprises a second epitope; wherein said first epitope and second epitope are the same epitope (i.e., the first antigen, in RNA-coded form, and the second antigen, in polypeptide form, share at least one common epitope). The kit may be used for sequential administration of the priming and the boosting compositions.

In another aspect, the invention relates to a method for treating or preventing an infectious disease, a method for inducing an immune response in a subject, or a method of vaccinating a subject, comprising: (i) administering to a subject in need thereof at least once a therapeutically effective amount of a priming composition comprising a self-replicating RNA molecule that encodes a first polypeptide antigen that comprises a first epitope, and (ii) subsequently administering the subject at least once a therapeutically effective amount of a boosting composition comprising a second polypeptide antigen that comprises a second epitope; wherein said first epitope and second epitope are the same epitope (i.e., the first antigen, in RNA-coded form, and the second antigen, in polypeptide form, share at least one common epitope).

As described herein, the inventors have evaluated RNA prime, protein boost vaccination strategies. These studies demonstrate several benefits of the RNA prime, protein boost strategy, as compared to a protein prime, protein boost strategy, including, for example, increased antibody titers, a more balanced $IgG_1$:$IgG_{2a}$ subtype profile, induction of $T_H1$ type, CD4+ T cell-mediated immune response that was similar to that of viral particles, and reduced production of non-neutralizing antibodies.

Preferably, the RNA molecule in the priming composition encodes a protein that is substantially the same as the polypeptide molecule in the boosting composition (e.g., the amino acid sequence encoded by the RNA molecule in the priming composition and the polypeptide in the boosting composition share at least about 90% sequence identity across the length of the shorter antigen). Alternatively, the two antigens have the same epitope, such as the same immunodominant epitope(s).

The priming and boosting compositions described herein can be formulated as a vaccine to induce or enhance the immune response to a pathogen. Also provided herein are methods of using the priming and boosting compositions of the invention to induce or enhance an immune response in a subject in need thereof.

The invention also relates to immunogenic compositions, pharmaceutical compositions, or kits as described herein for use in therapy, and to the use of immunogenic compositions, pharmaceutical compositions, or kits as described herein for the manufacture of a medicament for enhancing or generating an immune response.

2. Immunogenic Compositions

In one aspect, the invention provides an immunogenic composition comprising an RNA component and a polypeptide component. The immunogenic composition comprises: (i) a self-replicating RNA molecule that encodes a first polypeptide antigen comprising a first epitope (the RNA component); and (ii) a second polypeptide antigen comprising a second epitope (the polypeptide component); wherein said first epitope and second epitope are epitopes from the same pathogen.

The first epitope and second epitope can be the same epitope, or different epitopes if desired. The first epitope and second epitope can be from the same polypeptide of the pathogen, or different polypeptides of the pathogen. The first epitope and second epitope can also be epitopes which are highly conserved between different strains or subspecies of the pathogen, such as those epitopes with limited or no mutational variations. For example, the first epitope and the second epitope can be different epitopes from the same pathogen (e.g., the first epitope is from RSV F and the second epitope is from RSV G).

In certain embodiments, the first polypeptide antigen and the second polypeptide antigen are derived from the same protein from the pathogen. For example, the RNA molecule may encode a first polypeptide antigen comprising a full-length protein from a pathogen (e.g., a viral protein), or an antigenic portion thereof, optionally fused with a heterologous sequence that may facilitate the expression, production, purification or detection of the viral protein encoded by the RNA. The second polypeptide antigen may be a recombinant protein comprising the full-length protein, or an antigenic portion thereof, optionally fused with a heterologous sequence (e.g., His-tag) that may facilitate the expression, production, purification or detection of the second polypeptide antigen. Alternatively, the first polypeptide antigen, the second polypeptide antigen, or both, may comprise a mutation variant of a protein from a pathogen (e.g., a viral protein having amino acid substitution(s), addition(s), or deletion(s)).

Preferably, the amino acid sequence identity between the first polypeptide antigen and the second polypeptide antigen is at least about 40%, least about 50%, least about 60%, least about 65%, least about 70%, at least about 75%, at least about 80%, at least about 85%, at least about 90%, at least about 95%, at least about 96%, at least about 97%, at least about 98%, or at least about 99%. In certain embodiments, the first polypeptide antigen and the second polypeptide antigen are the same antigen.

In certain embodiments, the first polypeptide antigen and the polypeptide second antigen share at least 1, at least 2, at least 3, at least 4, or at least 5 common B-cell or T-cell epitopes. In certain embodiments, the first polypeptide antigen and the second polypeptide antigen have at least one common immunodominant epitope. In certain embodiments, the first polypeptide antigen and the second polypeptide antigen have the same immunodominant epitope(s), or the same primary immunodominant epitope.

In certain embodiments, the first polypeptide antigen is a soluble or membrane anchored polypeptide, and the second polypeptide antigen is a soluble polypeptide. For example, if the wild type viral protein is a transmembrane surface protein, the RNA molecule may comprise the full-length coding sequence to produce the first (membrane-anchored) antigen, while the transmembrane region of the viral protein may be deleted to produce the second polypeptide antigen (which is soluble).

In certain embodiment, the first antigen or the second antigen is a fusion polypeptide further comprising a third epitope. The third epitope may be from a different pathogen, or from a different antigen of the same pathogen.

A. Antigens

Antigens suitable for inclusion in the immunogenic compositions described herein (either in RNA-coded form or in polypeptide form) may be derived from any pathogen (e.g., a bacterial pathogen, a viral pathogen, a fungal pathogen, a protozoan pathogen, or a multi-cellular parasitic pathogen), allergen or tumor.

In certain embodiments, the first and second antigens are derived from a viral pathogen. Exemplary viral pathogens include, e.g., respiratory syncytial virus (RSV), hepatitis B virus (HBV), hepatitis C virus (HCV), Dengue virus, herpes simplex virus (HSV; e.g., HSV-I, HSV-II), molluscum contagiosum virus, vaccinia virus, variola virus, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza virus (flu), para-influenza virus, mumps virus, measles virus, papovavirus, hepadnavirus, flavivirus, retrovirus, arenavirus (e.g., Lymphocytic Choriomeningitis Virus, Junin virus, Machupo virus, Guanarito virus, or Lassa virus), norovirus, yellow fever virus, rabies virus, Filovirus (e.g., Ebola virus or marbug virus), hepatitis C virus, hepatitis B virus, hepatitis A virus, Morbilliviruses (e.g., measles virus), Rubulaviruses (e.g., mumps virus), Rubiviruses (e.g., *rubella* virus), bovine viral diarrhea virus. For example, the antigen can be CMV glycoprotein gH, or gL; Parvovirus; HIV glycoprotein gp120 or gp140, HIV p55 gag, pol; or RSV-F antigen, etc.

In some embodiments, the first and second antigens are derived from a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

In some embodiments the first and second antigens are derived from a parasite from the *Plasmodium* genus, such as *P. falciparum, P. vivax, P. malariae* or *P. ovale*. Thus the invention may be used for immunising against malaria. In some embodiments the first and second antigens are derived from a parasite from the Caligidae family, particularly those from the *Lepeophtheirus* and *Caligus* genera e.g. sea lice such as *Lepeophtheirus salmonis* or *Caligus rogercresseyi*.

In certain embodiments, first and second antigens are derived from a bacterial pathogen. Exemplary bacterial pathogens include, e.g., *Neisseria* spp, including *N. gonorrhea* and *N. meningitides; Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including *M. catarrhalis*, also known as *Branhamella catarrhalis; Bordetella* spp, including *B. pertussis, B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *H pylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. neumoniae, C. psittaci; Leptsira* spp., including *L. interrogans; Treponema* spp., including *T. pallidum, T. denticola, T. hyodysenteriae.*

In certain embodiments, first and second antigens are derived from a fungal pathogen (e.g., a yeast or mold pathogen). Exemplary fungal pathogens include, e.g., *Aspergillus fumigatus, A. flavus, A. niger, A. terreus, A. nidulans, Coccidioides immitis, Coccidioides posadasii, Cryptococcus neoformans, Histoplasma capsulatum, Candida albicans*, and *Pneumocystis jirovecii.*

In certain embodiments, first and second antigens are derived from a protozoan pathogen. Exemplary protozoan pathogens include, e.g., *Toxoplasma gondii* and *Strongyloides stercoralis.*

In certain embodiments, the first and second antigens are derived from a multi-cellular parasitic pathogen. Exemplary multicellular parasitic pathogens include, e.g., trematodes (flukes), cestodes (tapeworms), nematodes (roundworms), and arthropods.

In some embodiments, the first and second antigens are derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and Sorghum, the orders of Asterales and Urticales including herbs of the genera *Ambrosia, Artemisia*, and *Parietaria*. Other important inhalation allergens are those from house dust mites of the genus *Dermatophagoides* and Euroglyphus, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments, the first and second antigens are derived from a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

1. RSV

In some aspects, the pathogen is RSV. RSV is an enveloped non-segmented negative-strand RNA virus in the family Paramyxoviridae, genus *Pneumovirus*. To infect a host cell, paramyxoviruses such as RSV, like other enveloped viruses such as influenza virus and HIV, require fusion of the viral membrane with a host cell's membrane. For RSV, the conserved fusion protein (RSV-F glycoprotein) fuses the viral and cellular membranes by coupling irreversible protein refolding with juxtaposition of the membranes. In current models based on paramyxovirus studies, the RSV-F protein initially folds into a metastable "pre-fusion" conformation. During cell entry, the pre-fusion conformation undergoes refolding and conformational changes to its stable "post-fusion" conformation. See, also, Swanson et al., *PNAS USA* 108(23):9619-9624 (2011) regarding pre-fusion and post-fusion RSV-F structures.

In certain embodiments, the first and second antigens are from RSV. For example, the first and second antigens can independently be derived from the RSV surface glycoproteins Fusion (F), Glycoprotein (G), Small Hydrophobic protein (SH), the matrix proteins M and M2, the nucleocapsid proteins N, P and L, and the nonstructural proteins NS1 and NS2. In certain preferred embodiments, the first and second antigens are each an RSV-F antigen.

The F glycoprotein of RSV is a type I single-pass integral membrane protein having four general domains: N-terminal ER-translocating signal sequence (SS), ectodomain (ED), transmembrane domain (TM), and a cytoplasmic tail (CT). CT contains a single palmitoylated cysteine residue. The sequence of F protein is highly conserved among RSV isolates, but is constantly evolving (Kim et al. (2007) *J Med Virol* 79: 820-828). Unlike most paramyxoviruses, the F protein in RSV can mediate entry and syncytium formation independent of the other viral proteins (HN is usually necessary in addition to F in other paramyxoviruses).

The RSV-F glycoprotein is translated from mRNA into an approximately 574 amino acid protein designated $F_0$. Post-translational processing of $F_0$ includes removal of an N-terminal signal peptide by a signal peptidase in the endoplasmic reticulum. $F_0$ is also cleaved at two sites (approximately 109/110 and approximately 136/137) by cellular proteases (in particular furin) in the trans-Golgi. This cleavage results in the removal of a short intervening sequence and generates two subunits designated $F_1$ (~50 kDa; C-terminal; approximately residues 137-574) and $F_2$ (~20 kDa; N-terminal; approximately residues 1-109) that remain associated with each other. $F_1$ contains a hydrophobic fusion peptide at its N-terminus and also two amphipathic heptad-repeat regions (HRA and HRB). HRA is near the fusion peptide and HRB is near the transmembrane domain. Three $F_1$-$F_2$ heterodimers are assembled as homotrimers of $F_1$-$F_2$ in the virion.

RSV-F antigens suitable for inclusion in the immunogenic compositions described herein, either in RNA enconded form or as polypeptides, include RSV-F glycoprotein and RSV-F glycoprotein variants. Suitable RSV-F glycoprotein variants include, for example, full length F protein and truncated variants such as soluble ecto-domains, each optionally containing one or more mutations, such as furin-cleavage mutations, trypsin-cleavage mutations, fusion peptide mutations (e.g., deletions in whole or in part), mutations that stabilize the HRB trimer, and mutations that destabilize the HRA trimer.

Full length and truncated RSV-F glycoprotiens, including those with one or more such mutations in a variety of combinations are well known in the art and are disclosed for example in WO2011/008974, the disclosure of which is incorporated herein by reference in its entirety.

The skilled addressee is directed to the following sections of WO2011/008974 which disclose exemplary RSV-F antigens that can be used, in RNA form or as polypeptides, in the immunogenic compositions: (i) page 15, line 20 through page 16, line 27, which describes RSV-F, its amino acid sequence and domain structure; (ii) page 16, line 28 through page 18, line 11, which describes soluble ectodomains of RSV-F; (iii) page 18, line 14 through page 20, line 15, which describes furin-cleavage mutations, trypsin-cleavage mutations, fusion peptide mutations; (iv) page 20, line 16 through page 21, line 8, and page 26, line 29 through page 30, line 14, which describe optional oligomerization sequences; (v) page 20, lines 9-24, which describe introduced protease cleavage sites; (vi) and page 30, line 18 through page 32, line 18, which describe mutations that stabilize the HRB trimer, destabilize the HRA trimer and other mutations that can be included.

In particular embodiments, the sequence of amino acid residue 100-150 of the RSV-F glycoprotein, such as SEQ ID NO:1 or SEQ ID NO:2 disclosed in WO2011/008974, or the soluble ecto domains thereof, is:

(Furmet)
(SEQ ID NO: 25)
TPATNNRARKELPRFMNYTLNNAKKTNVTLSKKRKKKFLGFLLGVGSAIA
S (Furdel)
(SEQ ID NO: 26)
TPATNNRARQELPRFMNYTLNNAKKTNVTLSKK---RFLGFLLGVGSAIA
S (OFurex)
(SEQ ID NO: 27)
TPATNNQAQNELPQFMNYTLNNANNTNVTLSQNQNQNFLGFLLGVGSAIA
S (NFurex)
(SEQ ID NO: 28)
TPATNNQAQNELPQFMNYTLNNAQQTNVTLSQNQNQNFLGFLLGVGSAIA
S (Dp21Furex)
(SEQ ID NO: 29)
TPATNNQAQN---------------------QNQNQNFLGFLLGVGSAIA
S (Dp23Fures)
(SEQ ID NO: 30)
TPATNNQAQN-----------------------QNQNFLGFLLGVGSAIA
S -continued (Dp23furdel)
(SEQ ID NO: 31)
TPATNNRARQ-----------------------QQQRFLGFLLGVGSAIA
S (Nterm Furin)
(SEQ ID NO: 32)
TPATNNRARRELPQFMNYTLNNAQQTNVTLSQNQNQNFLGFLLGVGSAIA
S (Cterm Furin)
(SEQ ID NO: 33)
TPATNNQAQNELPQFMNYTLNNAQQTNVTLSKKRKRRFLGFLLGVGSAIA
S (Fusion peptide deletion 1)
(SEQ ID NO: 34)
TPATNNRARRELPRFMNYTLNNAKKTNVTLSKKRKRR---------
SAIAS, (Fusion peptide deletion 2)
(SEQ ID NO: 35)
TPATNNRARRELPRFMNYTLNNAKKTNVTLSKKRKRR------
GVGSAIAS, (Fusion peptide deletion 3)
(SEQ ID NO: 36)
TPATNNRARRELPRFMNYTLNNAKKTNVTLSKKRKRR--------
ASAIAS,
or (Factor Xa)
(SEQ ID NO: 37)
TPATNNIEGRELPRFMNYTLNNAKKTNVTLSKKIEGRFLGFLLGVGSAIA
S.

In the foregoing sequences, the symbol "-" indicates that the amino acid at that position is deleted.

In particular embodiments, the sequence of the RSV-F antigen comprises:

RSV-F Fusion Deletion 1 Truncated HIS
(SEQ ID NO: 38)
MELLILKANAITTILTAVTFCFASGQNITEEFYQSTCSAVSKGYLSALRTGWYTSVITIELSNIKENKCNGTDAKVKLIKQ
ELDKYKNAVTELQLLMQSTPATNNRARRELPRFMNYTLNNAKKTNVTLSKKRKRRSAIASGVAVSKVLHLEGEVNKIKSAL
LSTNKAVVSLSNGVSVLTSKVLDLKNYIDKQLLPIVNKQSCSISNIETVIEFQQKNNRLLEITRERSVNAGVTTPVSTYML
TNSELLSLINDMPITNDQKKLMSNNVQIVRQQSYSIMSIIKEEVLAYVVQLPLYGVIDTPCWKLHTSPLCTTNTKEGSNIC
LTRTDRGWYCDNAGSVSFFPQAETCKVQSNRVFCDTMNSLTLPSEVNLCNVDIFNPKYDCKIMTSKTDVSSSVITSLGAIV
SCYGKTKCTASNKNRGIIKTFSNGCDYVSNKGVDTVSVGNTLYYVNKQEGKSLYVKGEPIINFYDPLVFPSDEFDASISQV
NEKINQSLAFIRKSDELLHNVNAGKSTTNGGSAGSGHHHHHH RSV-F Fusion Deletion 2 Truncated HIS
(SEQ ID NO: 39)
MELLILKANAITTILTAVTFCFASGQNITEEFYQSTCSAVSKGYLSALRTGWYTSVITIELSNIKENKCNGTDAKVKLIKQ
ELDKYKNAVTELQLLMQSTPATNNRARRELPRFMNYTLNNAKKTNVTLSKKRKRRGVGSAIASGVAVSKVLHLEGEVNKIK
SALLSTNKAVVSLSNGVSVLTSKVLDLKNYIDKQLLPIVNKQSCSISNIETVIEFQQKNNRLLEITRERSVNAGVTTPVST
YMLTNSELLSLINDMPITNDQKKLMSNNVQIVRQQSYSIMSIIKEEVLAYVVQLPLYGVIDTPCWKLHTSPLCTTNTKEGS
NICLTRTDRGWYCDNAGSVSFFPQAETCKVQSNRVFCDTMNSLTLPSEVNLCNVDIFNPKYDCKIMTSKTDVSSSVITSLG
AIVSCYGKTKCTASNKNRGIIKTFSNGCDYVSNKGVDTVSVGNTLYYVNKQEGKSLYVKGEPIINFYDPLVFPSDEFDASI
SQVNEKINQSLAFIRKSDELLHNVNAGKSTTNGGSAGSGHHHHHH -continued RSV-F Fusion Deletion 3 Truncated HIS (SEQ ID NO: 40)

```
MELLILKANAITTILTAVTFCFASGQNITEEFYQSTCSAVSKGYLSALRTGWYTSVITIELSNIKENKCNGTDAKVKLIKQ

ELDKYKNAVTELQLLMQSTPATNNRARRELPRFMNYTLNNAKKTNVTLSKKRKRRASAIASGVAVSKVLHLEGEVNKIKSA

LLSTNKAVVSLSNGVSVLTSKVLDLKNYIDKQLLPIVNKQSCSISNIETVIEFQQKNNRLLEITRERSVNAGVTTPVSTYM

LTNSELLSLINDMPITNDQKKLMSNNVQIVRQQSYSIMSIIKEEVLAYVVQLPLYGVIDTPCWKLHTSPLCTTNTKEGSNI

CLTRTDRGWYCDNAGSVSFFPQAETCKVQSNRVFCDTMNSLTLPSEVNLCNVDIFNPKYDCKIMTSKTDVSSSVITSLGAI

VSCYGKTKCTASNKNRGIIKTFSNGCDYVSNKGVDTVSVGNTLYYVNKQEGKSLYVKGEPIINFYDPLVFPSDEFDASISQ

VNEKINQSLAFIRKSDELLHNVNAGKSTTNGGSAGSGHHHHHH
```

The sequences presented above contain a signal peptide and a HIS tag. The RSV-F protein used in the invention can contain any of the amino acid sequences shown above, with or without the signal peptide and/or HIS tag.

Examples of additional RSV F antigens that can be used in the invention include SEQ ID NOS: 6, 8 and 10 as disclosed in WO2009/079796 at pages 58-60, which are incorporated herein by reference.

The RSV-F polypeptide suitable for inclusion in the immunogenic compositions described herein may be in any desired form and conformation, including any desired mixture of forms and conformations. For example, the RSV-F polypeptide can be a monomer, or can be a trimer comprising three monomer polypeptides. Trimers can be monodispersed or can be in the form of a rosette, for example, due to interactions between the fusion peptides of individual timers. The immunogenic compositions may comprise RSV-F polypeptides that are monomers, trimers, a combination of monomers and trimers (e.g., in dynamic equilibrium), rosettes of trimers, and any combination of the foregoing. The forms and conformations of RSV-F, including monomers, trimers, a combination of monomers and trimers (e.g., in dynamic equilibrium), rosettes of trimers, cleaved and uncleaved forms, and pre-fusion and post-fusion forms are well known in the art, and are disclosed for example in WO2011/008974, the disclosure of which is incorporated herein by reference in its entirety. The skilled addressee is directed WO2011/008974, in particular at page 24, line 10 through page 26 line 27 and Examples 2-7, which RSV-F proteins in a variety of forms and conformations and methods for making them.

2. CMV

In some aspects, the pathogen is CMV, and the first and second antigens are independently derived from CMV. In certain embodiments, the first and second antigens are derived from a capsid protein, an envelope glycoprotein (such as gB, gH, gL, gM, gN), or a tegument protein. In certain embodiments, the first and second antigens are derived from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30, or US34A.

The CMV antigen may also be a fusion polypeptide of one or more CMV proteins, such as pp65/IE1 (Reap et al., Vaccine (2007) 25:7441-7449), gH/gL (Chowdary et al., Nature Structural & Molecular Biology, 17, 882-888 (2010)).

Suitable CMV antigens include gB, gH, gL, gO, and can be from any CMV strain. For example, CMV proteins can be from Merlin, AD169, VR1814, Towne, Toledo, TR, PH, TB40, or Fix strains of CMV. Exemplary sequences of CMV proteins that may be used for the invention are shown in Table 1.

TABLE 1

| | |
|---|---|
| Full length gH polynucleotide | (CMV gH FL) SEQ ID NO: 7 |
| Full length gH polypeptide | (CMV gH FL) SEQ ID NO: 8 |
| Full length gL polynucleotide | (CMV gL FL) SEQ ID NO: 11 |
| Full length gL polypeptide | (CMV gL FL) SEQ ID NO: 12 |
| Full length gO polynucleotide | (CMV gO FL) SEQ ID NO: 17 |
| Full length gO polypeptide | (CMV gO FL) SEQ ID NO: 18 |
| gH sol polynucleotide | (CMV gH sol) SEQ ID NO: 9 |
| gH sol polypeptide | (CMV gH sol) SEQ ID NO: 10 |
| Full length UL128 polynucleotide | (CMV UL128 FL) SEQ ID NO: 19 |
| Full length UL128 polypeptide | (CMV UL128 FL) SEQ ID NO: 20 |
| Full length UL130 polynucleotide | (CMV UL130 FL) SEQ ID NO: 21 |
| Full length UL130 polypeptide | (CMV UL130 FL) SEQ ID NO: 22 |
| Full length UL131 polynucleotide | (CMV UL131 FL) SEQ ID NO: 23 |
| Full length UL131 polypeptide | (CMV UL131 FL) SEQ ID NO: 24 |
| Full length gB polynucleotide | (CMV gB FL) SEQ ID NO: 1 |
| Full length gB polypeptide | (CMV gB FL) SEQ ID NO: 2 |
| gB sol 750 polynucleotide | (CMV gB 750) SEQ ID NO: 3 |
| gB sol 750 polypeptide | (CMV gB 750) SEQ ID NO: 4 |
| gB sol 692 polynucleotide | (CMV gB 692) SEQ ID NO: 5 |
| gB sol 692 polypeptide | (CMV gB 692) SEQ ID NO: 6 |
| Full length gM polynucleotide | (CMV gM FL) SEQ ID NO: 13 |
| Full length gM polypeptide | (CMV gM FL) SEQ ID NO: 14 |
| Full length gN polynucleotide | (CMV gN FL) SEQ ID NO: 15 |
| Full length gN polypeptide | (CMV gN FL) SEQ ID NO: 16 |

gB Antigens

In certain embodiments, the first antigen, the second antigen, or both, may be a gB antigen. A gB antigen can be full length gB protein or can omit one or more regions of the protein. Alternatively, fragments of a gB protein can be used. gB amino acids are numbered according to the full-length gB amino acid sequence (CMV gB FL) shown in SEQ ID NO: 2, which is 907 amino acids long. Suitable regions of a gB protein, which can be excluded from the full-length protein or included as fragments include: the signal sequence (amino acids 1-24), a gB-DLD disintegrin-like domain (amino acids 57-146), a furin cleavage site (amino acids 459-460), a heptad repeat region (679-693), a membrane spanning domain (amino acids 751-771), and a cytoplasmic domain from amino acids 771-906. In some embodiments, a gB antigen includes amino acids 67-86 (Neutralizing Epitope AD2) and/or amino acids 532-635 (Immunodominant Epitope AD1). Specific examples of gB antigens include "gB sol 692," which includes the first 692 amino acids of gB, and "gB sol 750," which includes the first 750 amino acids of gB. The signal sequence, amino acids 1-24, can be present or absent from gB sol 692 and gB sol 750 as desired.

In some embodiments, the gB antigen is a gB fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, or 875 amino acids.

The invention may also use a gB antigen comprising an amino acid sequence that is at least 75% identical to SEQ ID NO: 2 (e.g., at least 80%, at least 85%, at least 90%, at least 95%, at least 97%, at least 98%, at least 99%, or 100% identical to SEQ ID NO: 2).

gH Antigens

In certain embodiments, the first antigen, the second antigen, or both, may be a gH antigen. A gH antigen can be a full-length gH protein (CMV gH FL, SEQ ID NO:8, for example, which is a 743 amino acid protein). gH has a membrane spanning domain and a cytoplasmic domain starting at position 716 to position 743. Removing amino acids from 717 to 743 provides a soluble gH (e.g., CMV gH sol, SEQ ID NO: 10).

In some embodiments, the gH antigen is a gH fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or 725 amino acids.

The invention may also use a gH antigen comprising an amino acid sequence that is at least 75% identical to SEQ ID NO: 8 or 10 (e.g., at least 80%, at least 85%, at least 90%, at least 95%, at least 97%, at least 98%, at least 99%, or 100% identical to SEQ ID NO: 8 or 10).

gL Antigens

In certain embodiments, the first antigen, the second antigen, or both, may be a gL antigen. A gL antigen can be a full-length gL protein (CMV gL FL, SEQ ID NO:12, for example, which is a 278 amino acid protein). Alternatively, a gL fragment can be used. For example, the number of amino acids in the fragment can comprise 10, 15, 20, 30, 40, 50, 60, 70, 80, 90, 100, 125, 150, 175, 200, 225, or 250 amino acids.

The invention may also use a gL antigen comprising an amino acid sequence that is at least 75% identical to SEQ ID NO: 12 (e.g., at least 80%, at least 85%, at least 90%, at least 95%, at least 97%, at least 98%, at least 99%, or 100% identical to SEQ ID NO: 12).

gO Antigens

In certain embodiments, the first antigen, the second antigen, or both, may be a gO antigen. A gO antigen can be a full-length gO protein (CMV gO FL, SEQ ID NO:18, for example, which is a 472 amino acid protein). Alternatively, the gO antigen can be a gO fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, or 450 amino acids.

The invention may also use a gO antigen comprising an amino acid sequence that is at least 75% identical to SEQ ID NO: 18 (e.g., at least 80%, at least 85%, at least 90%, at least 95%, at least 97%, at least 98%, at least 99%, or 100% identical to SEQ ID NO: 18).

gM Antigens

In certain embodiments, the first antigen, the second antigen, or both, may be a gM antigen. A gM antigen can be a full-length gM protein (CMV gM FL, SEQ ID NO:14, for example, which is a 371 amino acid protein). Alternatively, the gM antigen can be a gM fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, or 350 amino acids.

The invention may also use a gM antigen comprising an amino acid sequence that is at least 75% identical to SEQ ID NO: 14 (e.g., at least 80%, at least 85%, at least 90%, at least 95%, at least 97%, at least 98%, at least 99%, or 100% identical to SEQ ID NO: 14).

gN Antigens

In certain embodiments, the first antigen, the second antigen, or both, may be a gN antigen. A gN antigen can be a full-length gN protein (CMV gN FL, SEQ ID NO:16, for example, which is a 135 amino acid protein). Alternatively, the gN antigen can be a gN fragment of 10 amino acids or longer. For example, the number of amino acids in the fragment can comprise 10, 15, 20, 30, 40, 50, 60, 70, 80, 90, 100, or 125 amino acids.

The invention may also use a gN antigen comprising an amino acid sequence that is at least 75% identical to SEQ ID NO: 16 (e.g., at least 80%, at least 85%, at least 90%, at least 95%, at least 97%, at least 98%, at least 99%, or 100% identical to SEQ ID NO: 16).

UL128 Antigens

In certain embodiments, the first antigen, the second antigen, or both, may be a UL128 antigen. A UL128 antigen can be a full-length UL128 protein (CMV UL128 FL, SEQ ID NO:20, for example, which is a 171 amino acid protein). Alternatively, the UL128 antigen can be a UL128 fragment of 10 amino acids or longer. For example, the number of amino acids in the fragment can comprise 10, 15, 20, 30, 40, 50, 60, 70, 80, 90, 100, 125, or 150 amino acids.

The invention may also use a UL128 antigen comprising an amino acid sequence that is at least 75% identical to SEQ ID NO: 20 (e.g., at least 80%, at least 85%, at least 90%, at least 95%, at least 97%, at least 98%, at least 99%, or 100% identical to SEQ ID NO: 20).

UL130 Antigens

In certain embodiments, the first antigen, the second antigen, or both, may be a UL130 antigen. A UL130 antigen can be a full-length UL130 protein (CMV UL130 FL, SEQ ID NO:22, for example, which is a 214 amino acid protein). Alternatively, the UL130 antigen can be a UL130 fragment of 10 amino acids or longer. For example, the number of amino acids in the fragment can comprise 10, 15, 20, 30, 40, 50, 60, 70, 80, 90, 100, 125, 150, 175, or 200 amino acids.

The invention may also use a UL130 antigen comprising an amino acid sequence that is at least 75% identical to SEQ ID NO: 22 (e.g., at least 80%, at least 85%, at least 90%, at least 95%, at least 97%, at least 98%, at least 99%, or 100% identical to SEQ ID NO: 22).

UL131 Antigens

In certain embodiments, the first antigen, the second antigen, or both, may be a UL131 antigen. A UL131 antigen can be a full-length UL131 protein (CMV UL131, SEQ ID NO:24, for example, which is a 129 amino acid protein). Alternatively, the UL131 antigen can be a UL131 fragment of 10 amino acids or longer. For example, the number of amino acids in the fragment can comprise 10, 15, 20, 30, 40, 50, 60, 70, 80, 90, 100, 125, 150, 175, or 200 amino acids.

The invention may also use a UL131 antigen comprising an amino acid sequence that is at least 75% identical to SEQ ID NO: 24 (e.g., at least 80%, at least 85%, at least 90%, at least 95%, at least 97%, at least 98%, at least 99%, or 100% identical to SEQ ID NO: 24).

The CMV antigen may be a fusion polypeptide. For example, the antigen may comprise a first domain and a second domain, wherein (i) the first domain comprises a first CMV antigen and (ii) the second domain comprises a second CMV antigen. The first CMV antigen and the second CMV antigen are independently selected from a gB, gH, gL, gO, gM, gN, UL128, UL130, or UL131 antigen described above.

Two or more CMV antigens may also be co-delivered in the form of a complex, or in a form that can form a complex in vivo (e.g., gH/gL complex, gM/gN complex, gH/gL/UL128/UL130/UL131 pentameric compelx). For example, the immunogenic composition may comprise an RNA molecule that encode two or more separate proteins, e.g, gH and gL. The immunogenic composition may also comprise two or more polypeptide antigens, e.g., gH and gL.

B. The RNA Molecule

The immunogenic composition described herein comprises an RNA component and a polypeptide component. Preferably, the RNA is a self-replicating RNA.

The composition can contain more than one RNA molecule encoding an antigen, e.g., two, three, five, ten or more RNA molecules. Alternatively or in addition, one RNA molecule may also encode more than one antigen, e.g., a bicistronic, or tricistronic RNA molecule that encodes different or identical antigens.

The sequence of the RNA molecule may be codon optimized or deoptimized for expression in a desired host, such as a human cell.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O]N), which may further increases translation efficacy.

If desired, the RNA molecule can comprise one or more modified nucleotides in addition to any 5' cap structure. There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxy-isopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethyl cytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hmSC (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-

$C_6$)-alkylcytosine, 5-methylcytosine, 5-($C_2$-$C_6$)-alkenylcytosine, 5-($C_2$-$C_6$)-allcynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), mSC, mSU, m6A, s2U, W, or 2'-O-methyl-U. Many of these modified nucleobases and their corresponding ribonucleosides are available from commercial suppliers. See, e.g., WO 2011/005799 which is incorporated herein by reference.

If desired, the RNA molecule can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

Self-Replicating RNA

In some aspects, the cationic oil in water emulsion contains a self-replicating RNA molecule. In certain embodiments, the self-replicating RNA molecule is derived from or based on an RNA virus or a retrovirus. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. Cells transfected with self-replicating RNA briefly produce of antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins or antigens by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other nonstructural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

When delivered to a vertebrate cell, a self-replicating RNA molecule can lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the gene product.

One suitable system for achieving self-replication is to use an alphavirus-based RNA replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based replicons are (+)-stranded replicons that can be translated after delivery to a cell to give of a replicase (or replicase-transcriptase). The replicase is translated as a polyprotein which auto-cleaves to provide a replication complex which creates genomic (−)-strand copies of the +-strand delivered RNA. These (−)-strand transcripts can themselves be transcribed to give further copies of the (+)-stranded parent RNA and also to give a subgenomic transcript which encodes the desired gene product. Translation of the subgenomic transcript thus leads to in situ expression of the desired gene product by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) a polypeptide antigen. The polymerase can be an alphavirus replicase e.g. comprising alphavirus protein nsP4.

Whereas natural alphavirus genomes encode structural virion proteins in addition to the non-structural replicase, it is preferred that an alphavirus based self-replicating RNA molecule of the invention does not encode alphavirus structural proteins. Thus the self-replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes a polypeptide antigen. In some embodiments the RNA may have additional (downstream) open reading frames e.g. that encode another desired gene products. A self-replicating RNA molecule can have a 5' sequence which is compatible with the encoded replicase.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA). Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more modified nucleotides (e.g., pseudouridine, N6-methyladenosine, 5-methylcytidine, 5-methyluridine).

The self-replicating RNA molecule may encode a single polypeptide antigen or, optionally, two or more of polypeptide antigens linked together in a way that each of the sequences retains its identity (e.g., linked in series) when expressed as an amino acid sequence. The polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol[90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

The self-replicating RNA of the invention may be delivered by a variety of methods, such as naked RNA delivery or in combination with lipids, polymers or other compounds that facilitate entry into the cells. The RNA molecules of the present invention can be introduced into target cells or subjects using any suitable technique, e.g., by direct injection, microinjection, electroporation, lipofection, biolystics, and the like.

C. The Polypeptide Molecule

The immunogenic composition described herein comprises a polypeptide component and an RNA component. The polypeptide component encompasses multi-chain polypeptide structures, such as a polypeptide complex (e.g., a complex formed by two or more proteins), or a large polypeptide structure, such as VLP.

Suitable antigens that can be used as the polypeptide component (the "second polypeptide antigen") of the immunogenic composition include proteins and peptides from any pathogen, such as a bacterial pathogen, a viral pathogen, a fungal pathogen, a protozoan pathogen, or a multi-cellular parasitic pathogen. Exemplary antigens include any one of the antigens described above, such as an antigen derived from RSV, HIV, or CMV. The composition can contain more than one polypeptide antigen. Alternatively or in addition, the polypeptide may also be a fusion polypeptide comprising two or more epitopes from two different proteins of the same pathogen, or two or more epitopes from two different pathogens.

The polypeptide antigen may include additional sequences, such as a sequence to facilitate expression, production, purification or detection (e.g., a poly-His sequence).

The polypeptide antigen will usually be isolated or purified. Thus, they will not be associated with molecules with which they are normally, if applicable, found in nature.

Polypeptides will usually be prepared by expression in a recombinant host system. Generally, they are produced by expression of recombinant constructs that encode the ectodomains in suitable recombinant host cells, although any suitable methods can be used. Suitable recombinant host cells include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese), bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), *Tetrahymena* cells (e.g., *Tetrahymena thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGELCR.pIX cell lines (ProBioGen) which are described, for example, in *Vaccine* 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insert cell expression systems are commercially available in kit form from, inter *alia*, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., Yeast Genetic Engineering (Barr et al., eds., 1989) Butterworths, London.

Recombinant constructs encoding a polypeptide can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

Polypeptides can be purified using any suitable methods. For example, methods for purifying polypeptides by immunoaffinity chromatography are known in the art. Ruiz-Arguello et al., *J. Gen. Virol.*, 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the polypeptides can include a "tag" that facilitates purification, such as an epitope tag or a HIS tag. Such tagged polypeptides can conveniently be purified, for example from conditioned media, by chelating chromatography or affinity chromatography.

D. Optional RNA Delivery Systems

In addition to the protein component and the RNA component, additional components, such as lipids, polymers or other compounds may be optionally included in the immunogenic composition as described herein to facilitate the entry of RNA into target cells.

Although RNA can be delivered as naked RNA (e.g. merely as an aqueous solution of RNA), to enhance entry into cells and also subsequent intercellular effects, the RNA molecule is preferably administered in combination with a delivery system, such as a particulate or emulsion delivery system. A large number of delivery systems are well known to those of skill in the art.

For example, the RNA molecule may be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

The RNA molecule of the present invention can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

Three particularly useful delivery systems are (i) liposomes (ii) non-toxic and biodegradable polymer microparticles (iii) cationic submicron oil-in-water emulsions.

1. Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols, and some useful phospholipids are listed in Table 2. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

TABLE 2

| Phospholipids | |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . . ) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol . . . ) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol . . . ) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Distearpyl-sn-Glycero-3-phosphatidylethanolamine |
| DSPG | 1,2-Distearoyl-sn-Glycero-3[Phosphatidyl-rac-(1-glycerol . . . ) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol) . . . ] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107: 276-87.

A mixture of DSPC, DlinDMA, PEG-DMPG and cholesterol is used in the examples. A separate aspect of the invention is a liposome comprising DSPC, DlinDMA, PEG-DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but at least half of the RNA (and ideally all of it) is encapsulated.

2. Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) Pharmaceutical Research 20: 247-251. An alternative way of making polymeric microparticles is by molding and curing e.g. as disclosed in WO2009/132206.

Microparticles of the invention can have a zeta potential of between 40-100 mV.

RNA can be adsorbed to the microparticles, and adsorption is facilitated by including cationic materials (e.g. cationic lipids) in the microparticle.

3. Oil-in-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery according to the present invention can utilise an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene can also be obtained from yeast or other suitable microbes. In some embodiments, Squalene is preferably obtained from non-animal sources, such as from olives, olive oil or yeast. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ϵ or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; $[(CH_3)_2C[=CHCH_2CH_2C(CH_3)]_2=CHCH_2-]_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilisation of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N—(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP), N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecylammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemethanaminium chloride (DEBDA), dialkyldimetylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_2Me_6$; $C_{12}Bu_6$), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol, including but not limited to cholesteryl-3β-oxysuccinamidoethylenetrimethylammonium salt, cholesteryl-3β-oxysuccinamidoethylene dimethylamine, cholesteryl-3β-carboxyamidoethylenetrimethylammonium salt, cholesteryl-3β-carboxyamidoethylenedimethylamine. Other useful cationic lipids are described in US 2008/0085870 and US 2008/0057080, which are incorporated herein by reference.

The cationic lipid is preferably biodegradable (metabolisable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON™ X-100 surfactant, or t-octylphenoxypolyethoxyethanol) being of particular interest; (octylphenoxy) polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as BRIJ® surfactants), such as triethyleneglycol monolauryl ether (BRIJ® 30 surfactant); polyoxyethylene-9-lauryl ether; and sorbitan esters (commonly known as the Spans), such as sorbitan trioleate (SPAN® 85 surfactant) and sorbitan monolaurate. Preferred surfactants for including in the emulsion are polysorbate 80 (TWEEN™ 80 surfactant); polyoxyethylene sorbitan monooleate), SPAN® 85 surfactant (sorbitan trioleate), lecithin and TRITON™ X-100 surfactant.

Mixtures of these surfactants can be included in the emulsion e.g. TWEEN™ 80/SPAN® 85 surfactant mixtures, or TWEEN® 80/TRITON™-X100 surfactant mixtures. A combination of a polyoxyethylene sorbitan ester such as polyoxyethylene sorbitan monooleate (TWEEN® 80 surfactant) and an octoxynol such as t-octylphenoxy-polyethoxyethanol (TRITON™ X-100 surfactant) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as TRITON™ X-100 surfactant) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These these typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion. These methods can also provide a submicron emulsion with a tight particle size distribution.

Preferred emulsions can be filter sterilised i.e. their droplets can pass through a 220 nm filter. As well as providing a sterilisation, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

The RNA molecules of the invention can also be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have been transfected with the RNA molecule. The appropriate amount of cells to deliver to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

E. Adjuvants

In certain embodiments, the immunogenic compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

1. Mineral Containing Compositions

Mineral containing compositions suitable for use as adjuvants include mineral salts, such as aluminum salts and calcium salts. The immunogenic composition may include mineral salts such as hydroxides (e.g., oxyhydroxides), phosphates (e.g., hydroxyphosphates, orthophosphates), sulfates, etc. (see, e.g., Vaccine Design: The Subunit and Adjuvant Approach (Powell, M. F. and Newman, M J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In certain embodiments, the aluminum based adjuvant is alum (aluminum potassium sulfate ($AlK(SO_4)_2$), or an alum derivative, such as that formed in-situ by mixing an antigen in phosphate buffer with alum, followed by titration and precipitation with a base such as ammonium hydroxide or sodium hydroxide.

Another aluminum-based adjuvant suitable for use in vaccine formulations is aluminum hydroxide adjuvant ($Al(OH)_3$) or crystalline aluminum oxyhydroxide (AlOOH), which is an excellent adsorbant, having a surface area of approximately 500 $m^2/g$. Alternatively, the aluminum based adjuvant can be aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In certain embodiments, the adjuvant comprises both aluminum phosphate and aluminum hydroxide. In a more particular embodiment, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep=4). Alternatively, pretreatment of aluminum hydroxide with phosphate lowers its isoelectric point, making it a preferred adjuvant for more basic antigens.

2. Oil-Emulsions

Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) VACCINE 19: 2673-2680; Frey et al. (2003) Vaccine 21:4234-4237. MF59 is used as the adjuvant in the FLUAD™ influenza virus trivalent subunit vaccine.

Particularly preferred oil-emulsion adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN® 80 surfactant (polyoxyethylenesorbitan monooleate), and/or 0.25-1.0% SPAN 85TM surfactant (sorbitan trioleate), and, optionally, N-acetylmuramyl-L-alanyl-D-isogluatminyl-L-alanine-2-(1'-2'-dipalmitoyl-SM-glycero-3-huydroxyphosphophoryloxy)-ethylamine (MTP-PE), for example, the submicron oil-in-water emulsion known as "MF59" (WO 90/14837; U.S. Pat. Nos. 6,299,884; 6,451,325; and Ott et al., "MF59—Design and Evaluation of a Safe and Potent Adjuvant for Human Vaccines" in Vaccine Design: The Subunit and Adjuvant Approach (Powell, M. F. and Newman, MJ. eds.) (New York: Plenum Press) 1995, pp. 277-296). MF59 contains 4-5% w/v Squalene (e.g. 4.3%), 0.25-0.5% w/v TWEEN® 80 surfactant, and 0.5% w/v SPAN 85TM surfactant and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v TWEEN® 80 surfactant, and 0.75% w/v SPAN 85™ surfactant and optionally MTP-PE. Yet another submicron oil-in-water emulsion is MF75, also known as SAF, containing 10% squalene, 0.4% TWEEN® 80 surfactant, 5% pluronic—blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

3. Other Immunological Adjuvants

Saponins are a heterologous group of sterol glycosides and triterpenoid glycosides that are found in the bark, leaves, stems, roots and even flowers of a wide range of plant species. Saponins isolated from the bark of the Quillaia saponaria Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS 17, QS 18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Saponin formulations may include sterols, cholesterols and lipid formulations. Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) Adv. Drug Del. Rev. 32:247-271. See also Sjolander et al. (1998) Adv. Drug Del. Rev. 32:321-338.

Virosomes and Virus Like Particles (VLPs) generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in WO 03/024480; WO 03/024481; Niikura et al. (2002) Virology 293:273-280; Lenz et al. (2001) J. Immunol. 166(9):5346-5355' Pinto et al. (2003) J. Infect. Dis. 188: 327-338; and Gerber et al. (2001) J. Virol. 75(10):4752-4760. Virosomes are discussed further in, for example, Gluck et al. (2002) Vaccine 20:B10-B16. Immunopotentiating reconstituted influenza virosomes (IRIV) are used as the subunit antigen delivery system in the intranasal trivalent INFLEXAL™ product (Mischler and Metcalfe (2002) Vaccine 20 Suppl 5:B17-B23) and the INFLUVAC PLUS™ product.

Bacterial or microbial derivatives suitable for use as adjuvants include, but are not limited to:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) Bioorg. Med. Chem. Lett. 9:2273-2278.

(2) Lipid A Derivatives: Lipid A derivatives include derivatives of lipid A from *Escherichia coli* such as OM-174. OM-174 is described for example in Meraldi et al. (2003) Vaccine 21:2485-2491; and Pajak et al. (2003) Vaccine 21:836-842. Another exemplary adjuvant is the synthetic phospholipid dimer, E6020 (Eisai Co. Ltd., Tokyo, Japan), which mimics the physicochemical and biological properties of many of the natural lipid A's derived from Gram-negative bacteria.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) Nucl. Acids Res. 31(9): 2393-2400; WO 02/26757; and WO 99/62923 for examples of possible analog substitutions. The adjuvant effect of CpG oligonucleotides is further discussed in Krieg (2003) Nat. Med. 9(7):831-835; McCluskie et al. (2002) FEMS Immunol. Med. Microbiol. 32: 179-185; WO 98/40100; U.S. Pat. Nos. 6,207,646; 6,239,116; and 6,429,199.

The CpG sequence may be directed to TLR9, such as the motif GTCGTT or TTCGTT. See Kandimalla et al. (2003) Biochem. Soc. Trans. 31 (part 3):654-658. The CpG sequence may be specific for inducing a ThI immune response, such as a CpG-A ODN, or it may be more specific for inducing a B cell response, such a CpG-B ODN. CpG-A and CpG-B ODNs are discussed in Blackwell et al. (2003) J. Immunol. 170(8):4061-4068; Krieg (2002) TRENDS Immunol. 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) BBRC 306:948-953; Kandimalla et al. (2003) Biochem. Soc. Trans. 31 (part 3):664-658' Bhagat et al. (2003) BBRC 300:853-861; and WO03/035836.

Immunostimulatory oligonucleotides and polymeric molecules also include alternative polymer backbone structures such as, but not limited to, polyvinyl backbones (Pitha et al. (1970) Biochem. Biophys. Acta 204(1):39-48; Pitha et al. (1970) Biopolymers 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

Adjuvant IC31, Intercell AG, Vienna, Austria, is a synthetic formulation that contains an antimicrobial peptide, KLK, and an immunostimulatory oligonucleotide, ODNIa. The two component solution may be simply mixed with antigens (e.g., particles in accordance with the invention with an associated antigen), with no conjugation required.

ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), *cholera* ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) Infect. Immun 70(6):3012-3019; Pizza et al. (2001) Vaccine 19:2534-2541; Pizza et al. (2000) J. Med. Microbiol. 290(4-5):455-461; Scharton-Kersten et al. (2000) Infect. Immun. 68(9):5306-5313' Ryan et al. (1999) Infect. Immun. 67(12):6270-6280; Partidos et al. (1999) Immunol. Lett. 67(3):209-216; Peppoloni et al. (2003) Vaccines 2(2): 285-293; and Pine et al. (2002) J. Control Release 85(1-3): 263-270. Numerical reference for amino acid substitutions is preferably based on the alignments of the A and B subunits of ADP-ribosylating toxins set forth in Domenighini et al. (1995) MoI. Microbiol. 15(6): 1165-1167.

Bioadhesives and mucoadhesives may also be used as adjuvants. Suitable bioadhesives include esterified hyaluronic acid microspheres (Singh et al. (2001) J. Cont. Release 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

Examples of liposome formulations suitable for use as adjuvants are described in U.S. Pat. Nos. 6,090,406; 5,916,588; and EP Patent Publication No. EP 0 626 169.

Adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

PCPP formulations suitable for use as adjuvants are described, for example, in Andrianov et al. (1998) Biomaterials 19(1-3): 109-115; and Payne et al. (1998) Adv. Drug Del. Rev. 31(3): 185-196.

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

Examples of imidazoquinoline compounds suitable for use as adjuvants include Imiquimod and its analogues, which are described further in Stanley (2002) Clin. Exp. Dermatol. 27(7):571-577; Jones (2003) Curr. Opin. Investig. Drugs 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α. examples of benzonaphthyridine compounds suitable for use as adjuvants include:

Examples of benzonaphthyridine compounds suitable for use as adjuvants, as well as methods of formulating and manufacturing, include those described in WO 2009/111337.

Lipopeptides suitable for use as adjuvants are described above. Other exemplary lipopeptides include, e.g., LP 40, which is an agonist of TLR2. See, e.g., Akdis, et al, Eur. J. Immunology, 33: 2717-26 (2003). Murein lipopeptides are lipopeptides derived from *E. coli*. See, Hantke, et al., Eur. J. Biochem., 34: 284-296 (1973). Murein lipopeptides comprise a peptide linked to N-acetyl muramic acid, and are thus related to Muramyl peptides, which are described in Baschang, et al., Tetrahedron, 45(20): 6331-6360 (1989).

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

Microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 μm in diameter. In certain embodiments, the particle diameter is about 200 nm to about 30 μm, and in other embodiments the particle diameter is about 500 nm to 10 μm.

3. Kits (A) Kits for Co-Administration of an RNA Molecule and a Polypeptide Molecule The invention also provides kits, wherein an RNA molecule encoding a first polypeptide antigen (the RNA component); and a second polypeptide antigen (the polypeptide component), are in separate containers. For example, the kit can contain a first container comprising a composition comprising an RNA molecule encoding a first polypeptide antigen, and a second container comprising a composition comprising a second polypeptide antigen. The polypeptide or the RNA molecule can be in liquid form or can be in solid form (e.g., lyophilized).

The kits described may be used for co-delivery of the RNA component and the polypeptide component of the immunogenic compositions described herein (e.g., the RNA component and the polypeptide component are mixed prior to administration for simultaneous delivery, e.g., mixed within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, or about 5 minutes prior to administration).

(B) Kits for Prime-Boost

In another aspect, the invention provides a kit comprising: (i) a priming composition comprising a self-replicating RNA molecule that encodes a first polypeptide antigen that comprises a first epitope; and (ii) a boosting composition comprising a second polypeptide antigen that comprises a second epitope; wherein said first epitope and second epitope are the same epitope. The kits are suitable for sequential administration of the RNA and the polypeptide, such as a "RNA prime, protein boost" immunization regimen to generate an immune response to a pathogen.

Suitable antigens that can be used as the RNA-coded antigen (the first polypeptide antigen) for the priming composition, or the polypeptide antigen (the second polypeptide antigen) for the boosting composition include proteins and peptides from any pathogen, such as a bacterial pathogen, a viral pathogen, a fungal pathogen, a protozoan pathogen, or a multi-cellular parasitic pathogen. Exemplary antigens include any one of the antigens described above, such as an antigen derived from RSV, HIV, or CMV.

The RNA molecule of the priming composition can be delivered as naked RNA (e.g. merely as an aqueous solution of RNA). Alternatively, to enhance entry into cells and also subsequent intercellular effects, the priming composition may optionally comprise a delivery system (such as a particulate or emulsion delivery system), so that the RNA molecule is administered in combination with the delivery system. Exemplary delivery systems are described above. The delivery system may be in the same container as the RNA molecule (e.g., pre-formulated), or in a different container from the RNA (e.g., the RNA and the delivery system are separately packaged, and may be combined, e.g., within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, or about 5 minutes prior to administration).

The priming composition, the boosting composition, or both, may optionally include one or more immunoregulatory agents such as adjuvants, as described herein. The immunoregulatory agent may be in the same container as the priming or boosting composition, or in a separate contained that can be combined with the priming or boosting composition prior to administration.

The priming composition comprising the RNA molecule or the boosting composition comprising the polypeptide can be in liquid form or can be in solid form (e.g., lyophilized).

(C) Other Components of the Kits

Suitable containers include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a third container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a fourth container comprising an adjuvant (such as an aluminum containing adjuvant or MF59).

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions, the priming compositions, or the boosting compositions described above.

4. Pharmaceutical Compositions

In one aspect, the invention relates to pharmaceutical compositions comprising an RNA component and a polypeptide component. The pharmaceutical composition comprises: (i) a self-replicating RNA molecule that encodes a first polypeptide antigen comprising a first epitope (the RNA component); and (ii) a second polypeptide antigen comprising a second epitope (the polypeptide component); wherein said first epitope and second epitope are epitopes from the same pathogen; and (iii) a pharmaceutically acceptable carrier and/or a pharmaceutically acceptable vehicle.

In another aspect, the invention relates to a kit comprising: (i) a priming composition comprising a self-replicating RNA molecule that encodes a first polypeptide antigen that comprises a first epitope; and (ii) a boosting composition comprising a second polypeptide antigen that comprises a second epitope; wherein said first epitope and second epitope are the same epitope; and wherein the priming composition, the boosting composition, or both, comprise(s) a pharmaceutically acceptable carrier and/or a pharmaceutically acceptable vehicle.

The pharmaceutical compositions typically include a pharmaceutically acceptable carrier and/or a suitable delivery system as described herein (such as liposomes, nanoemulsions, PLG micro- and nanoparticles, lipoplexes, chitosan micro- and nanoparticles and other polyplexes for RNA delivery). If desired other pharmaceutically acceptable components can be included, such as excipients and adjuvants. These pharmaceutical compositions can be used as vaccines.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used. Suitable pharmaceutically acceptable carriers for use in the pharmaceutical compositions include plain water (e.g. w.f.i.) or a buffer e.g. a phosphate buffer, a Tris buffer, a borate buffer, a succinate buffer, a histidine buffer, or a citrate buffer. Buffer salts will typically be included in the 5-20 mM range.

The pharmaceutical compositions are preferably sterile, and may be sterilized by conventional sterilization techniques.

The compositions may contain pharmaceutically acceptable auxiliary substances as required to approximate physiological conditions such as pH adjusting and buffering agents, and tonicity adjusting agents and the like, for example, sodium acetate, sodium chloride, potassium chloride, calcium chloride, sodium lactate and the like.

Preferably, the pharmaceutical compositions of the invention may have a pH between 5.0 and 9.5, e.g. between 6.0 and 8.0.

Pharmaceutical compositions of the invention may include sodium salts (e.g. sodium chloride) to give tonicity. A concentration of 10±2 mg/ml NaCl is typical e.g. about 9 mg/ml.

Pharmaceutical compositions of the invention may have an osmolarity of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably non-pyrogenic e.g. containing <1 EU (endotoxin unit, a standard measure) per dose, and preferably <0.1 EU per dose. Pharmaceutical compositions of the invention are preferably gluten free.

The concentrations of the polypeptide molecule and/or the RNA molecule in the pharmaceutical compositions can vary, and will be selected based on fluid volumes, viscosities, body weight and other considerations in accordance with the particular mode of administration selected and the intended recipient's needs. However, the pharmaceutical compositions are formulated to provide an effective amount of RNA+ polypeptide (either administered simultaneously, or administered sequentially, such as RNA prime, protein boost), such as an amount (either in a single dose or as part of a series) that is effective for treatment or prevention. This amount varies depending upon the health and physical condition of the individual to be treated, age, the taxonomic group of individual to be treated (e.g. non-human primate, primate, etc.), the capacity of the individual's immune system to react to the antigen encoded protein or peptide, the condition to be treated, and other relevant factors. It is expected that the amount will fall in a relatively broad range that can be determined through routine trials. The RNA content of compositions will generally be expressed in terms of the amount of RNA per dose. A preferred dose has ≤200 μg, ≤100 μg, ≤50 μg, or ≤10 μg RNA, and expression can be seen at much lower levels e.g. ≤1 μg/dose, ≤100 ng/dose, ≤10 ng/dose, ≤1 ng/dose, etc. The amount of polypeptide in each dose will generally comprise from about 0.1 to about 100 μg of polypeptide, with from about 5 to about 50 μg being preferred and from about 5 to about 25 μg/dose being alternatively preferred.

The amount of adjuvant, if any, will be an amount that will induce an immunomodulating response without significant adverse side effect. An optional amount for a particular vaccine can be ascertained by standard studies involving observation of a vaccine's antibody titers and their virus neutralization capabilities. The amount of adjuvant will be from about 1 to about 100 μg/dose, with from about 5 to about 50 μg/dose being preferred, and from about 20 to about 50 μg/dose being alternatively preferred.

Formulations suitable for parenteral administration, such as, for example, by intraarticular (in the joints), intravenous or intraperitoneal injection, and preferably by intramuscular, intradermal or subcutaneous injection, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials. Injection solutions and suspensions can be prepared from sterile powders, granules, and tablets. Cells transduced by the RNA molecules can also be administered intravenously or parenterally.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

It is recognized that polypeptide and RNA molecules, when administered orally, must be protected from digestion. Protection of polypeptide and RNA molecules can typically be accomplished either by complexing the RNA molecule or the polypeptide molecule with a composition to render the RNA/polypeptide resistant to acidic and enzymatic hydrolysis, or by packaging the RNA molecule or the polypeptide molecule in an appropriately resistant carrier such as a liposome. Means of protecting nucleic acids (such as RNA molecules) and polypeptides from digestion are well known in the art.

The pharmaceutical compositions can be encapsulated, e.g., in liposomes, or in a formulation that provides for slow release of the active ingredient. For example, the RNA molecule may be formulated as liposomes, then administered as a priming composition. Alternatively, liposome-formulated RNA may be mixed with the polypeptide molecule to produce the RNA+ polypeptide immunogenic composition of the invention. Alternatively, the RNA molecule and the polypeptide molecule can be co-encapsulated in liposomes.

The compositions described herein (priming compositions, boosting compositions, or immunogenic compositions comprising an RNA and a polypeptide), alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable suppository formulations may contain the RNA, the polypeptide, or the polypeptide and RNA combination as described herein, and a suppository base. Suitable suppository bases include natural or synthetic triglycerides or paraffin hydrocarbons. It is also possible to use gelatin rectal capsules filled with the polypeptide and RNA molecules as described herein, and a suitable base, for example, liquid triglycerides, polyethylene glycols, and paraffin hydrocarbons.

5. Methods of Generating or Enhancing Immune Responses (A) Co-Administration of an RNA Molecule and a Polypeptide Molecule In another aspect, the invention provides a method for inducing, generating or enhancing an immune response in a subject in need thereof, such as a vertebrate, preferably a mammal, comprising administering an effective amount of an immunogenic composition comprising an RNA component and a polypeptide component. The composition comprises: (i) a self-replicating RNA molecule that encodes a first polypeptide antigen comprising a first epitope (the RNA component); and (ii) a second polypeptide antigen comprising a second epitope (the polypeptide component); wherein said first epitope and second epitope are epitopes from the same pathogen. The immune response is preferably protective and preferably involves antibodies and/or cell-mediated immunity. The method may be used to induce a primary immune response and/or to boost an immune response.

In another aspect, the immunogenic compositions disclosed herein may be used in the manufacture of a medicament for inducing, generating, or enhancing an immune response in a subject in need thereof, such as a vertebrate, preferably a mammal.

In another aspect, the invention provides a method for treating or preventing an infectious disease in a subject (such as a vertebrate, preferably a mammal) in need thereof, comprising administering an effective amount of an immunogenic composition comprising an RNA component and a polypeptide component. The composition comprises: (i) a self-replicating RNA molecule that encodes a first polypeptide antigen comprising a first epitope(the RNA component); and (ii) a second polypeptide antigen comprising a second epitope (the polypeptide component); wherein said first epitope and second epitope are epitopes from the same pathogen.

In another aspect, the compositions disclosed herein may be used in the manufacture of a medicament for treating or preventing an infectious disease in a subject in need thereof, such as a vertebrate, preferably a mammal.

In another aspect, the invention provides a method for vaccinating a subject, such as a vertebrate, preferably a mammal, or immunizing a subject against a pathogen (e.g., a bacterial pathogen, a viral pathogen, a fungal pathogen, a protozoan pathogen, or a multi-cellular parasitic pathogen), comprising administering to a subject in need thereof an effective amount of an immunogenic composition comprising an RNA component and a polypeptide component. The composition comprises: (i) a self-replicating RNA molecule that encodes a first polypeptide antigen comprising a first epitope (the RNA component); and (ii) a second polypeptide antigen comprising a second epitope (the polypeptide component); wherein said first epitope and second epitope are epitopes from the same pathogen.

In another aspect, the compositions disclosed herein may be used in the manufacture of a medicament for vaccinating a subject in need thereof, such as a vertebrate, preferably a mammal.

When the RNA molecule and the polypeptide molecule are co-administered, it may still be desirable to package the polypeptide molecule and RNA molecule separately. The two components may be combined, e.g., within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, or about 5 minutes prior to administration. For example, the polypeptide molecule and RNA molecule can be combined at a patient's bedside.

(B) Prime-Boost

One aspect of the invention relates to the "prime and boost" immunization regimes in which the immune response induced by a priming composition is boosted by a boosting composition. For example, following priming (at least once) with an antigen (e.g., a polypeptide antigen, an RNA-coded antigen, an attenuated pathogen, or a combination thereof), a boosting composition comprising substantially the same antigen in the same form (e.g., protein prime, protein boost; RNA prime, RNA boost; etc.), substantially the same antigen in a different form (e.g., RNA prime, protein boost; in which the RNA and the protein are directed to the same target antigen), or a different antigen in the same or a different form (e.g., RNA prime targeting antigen 1, protein boost targeting antigen 2, wherein antigen 1 and antigen 2 are different but share a common epitope), may be administered to boost the immune response in the primed host.

In another aspect, the invention provides a method for inducing, generating or enhancing an immune response in a subject in need thereof, such as a vertebrate, preferably a mammal, comprising: (i) administering to a subject in need thereof at least once a therapeutically effective amount of a priming composition comprising a self-replicating RNA molecule that encodes a first polypeptide antigen that comprises a first epitope; and (ii) subsequently administering the subject at least once a therapeutically effective amount of a boosting composition comprising a second polypeptide antigen that comprises a second epitope; wherein said first epitope and second epitope are the same epitope. The immune response is preferably protective and preferably involves antibodies and/or cell-mediated immunity.

In another aspect, the priming and boosting compositions disclosed herein may be used in the manufacture of a medicament for inducing, generating, or enhancing an immune response in a subject in need thereof, such as a vertebrate, preferably a mammal.

In another aspect, the invention provides a method for treating or preventing an infectious disease in a subject (such as a vertebrate, preferably a mammal) in need thereof, comprising: (i) administering to a subject in need thereof at least once a therapeutically effective amount of a priming composition comprising a self-replicating RNA molecule that encodes a first polypeptide antigen that comprises a first epitope; and (ii) subsequently administering the subject at least once a therapeutically effective amount of a boosting composition comprising a second polypeptide antigen that comprises a second epitope; wherein said first epitope and second epitope are the same epitope.

In another aspect, the priming and boosting compositions disclosed herein may be used in the manufacture of a medicament for treating or preventing an infectious disease in a subject in need thereof, such as a vertebrate, preferably a mammal.

In another aspect, the invention provides a method for vaccinating a subject, such as a vertebrate, preferably a mammal, or immunizing a subject against a pathogen (e.g., a bacterial pathogen, a viral pathogen, a fungal pathogen, a protozoan pathogen, or a multicellular parasitic pathogen), comprising: (i) administering to a subject in need thereof at least once a therapeutically effective amount of a priming composition comprising a self-replicating RNA molecule that encodes a first polypeptide antigen that comprises a first epitope; and (ii) subsequently administering the subject at least once a therapeutically effective amount of a boosting composition comprising a second polypeptide antigen that comprises a second epitope; wherein said first epitope and second epitope are the same epitope.

In another aspect, the priming and boosting compositions disclosed herein may be used in the manufacture of a medicament for vaccinating a subject in need thereof, such as a vertebrate, preferably a mammal.

The priming composition and the boosting composition may be substantially the same (e.g., RNA+ protein prime, RNA+ protein boost), or may be different (e.g., RNA+ protein prime, protein boost).

The antigens (either in polypeptide form or in RNA-coded form) to be included in the priming and boosting compositions need not be identical, but should share at least one common epitope (e.g., the priming composition comprising an RNA molecule that encodes a first polypeptide antigen that comprises a first epitope; the boosting composition comprising a second polypeptide antigen that comprises a second epitope; wherein said first epitope and second epitope are the same epitope).

One embodiment of the invention uses an "RNA prime, protein boost" immunization strategy. Following priming (at least once) with an RNA molecule, a polypeptide molecule is subsequently administered to boost the immune response in the primed host.

Another embodiment of the invention uses an "RNA+ protein prime, protein boost" strategy. Following priming (at least once) with an immunogenic composition comprising an RNA molecule and a polypeptide molecule, a polypeptide molecule is subsequently administered to boost the immune response in the primed host.

The subject may be primed and/or boosted more than once. For example, the immunization strategy can be prime, prime, boost; or prime, boost, boost. In certain embodiment, the priming composition is administered as least twice, at least 3 times, at least 4 times, or at least 5 times. In certain embodiment, the boost composition is administered as least twice, at least 3 times, at least 4 times, or at least 5 times.

Administration of the boosting composition is generally weeks or months after administration of the priming composition, such as about 1 week, about 2 weeks, about 3 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 1 month, about 2 months, about 3 months, about 4 months, about 5 months, about 6 months, about 7 months, about 8 months, about 9 months, about 10 months, about 11 months, about 12 months, about 18 months, about 2 years, about 3 years, about 4 years, about 5 years, about 6 years, about 7 years, about 8 years, about 9 years, or about 10 years after the priming composition is administered.

(C) Additional Considerations for Administration

Suitable animal subjects for administration of the compositions disclosed herein include, for example, fish, birds, cattle, pigs, horses, deer, sheep, goats, bison, rabbits, cats, dogs, chickens, ducks, turkeys, and the like. The mammal is preferably a human. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

Preferred routes of administration include, but are not limited to, intramuscular, intraperitoneal, intradermal, subcutaneous, intravenous, intraarterial, and intraoccular injection. Oral and transdermal administration, as well as administration by inhalation or suppository is also contemplated. Particularly preferred routes of administration include intramuscular, intradermal and subcutaneous injection. According to some embodiments of the present invention, the composition is administered to a host animal using a needleless injection device, which are well-known and widely available.

It is sometimes advantageous to employ a vaccine that targets a particular target cell type (e.g., an antigen presenting cell or an antigen processing cell).

Catheters or like devices may be used to deliver the composition of the invention, as polypeptide+naked RNA, polypeptide+RNA formulated with a delivery system (e.g., RNA encapsulated in liposomes), RNA only, or polypeptide only into a target organ or tissue. Suitable catheters are disclosed in, e.g., U.S. Pat. Nos. 4,186,745; 5,397,307; 5,547,472; 5,674,192; and 6,129,705, all of which are incorporated herein by reference. The RNA molecules of the invention can also be introduced directly into a tissue, such as muscle. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of RNA into cells of a mammal. These methods are useful not only for in vivo introduction of RNA into a mammal, but also for ex vivo modification of cells for reintroduction into a mammal.

The present invention includes the use of suitable delivery systems, such as liposomes, polymer microparticles or submicron emulsion microparticles with encapsulated or adsorbed RNA, or RNA+polypeptide, to deliver the RNA, or RNA+polypeptide, to elicit an immune response. The invention includes liposomes, microparticles, submicron emulsions, or combinations thereof, with adsorbed and/or encapsulated RNA, or RNA+polypeptide.

The compositions disclosed herein that include one or more antigens, or are used in conjunction with one or more antigens, may be administered to patients at substantially the same time as (e.g., during the same medical consultation or visit to a healthcare professional or vaccination centre) other vaccines, e.g., at substantially the same time as a measles vaccine, a mumps vaccine, a *rubella* vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

6. Definitions

The term "about", as used here, refers to +/−10% of a value.

An "antigen" refers to a molecule containing one or more epitopes (either linear, conformational or both), that elicits an immunological response.

An "epitope" is a portion of an antigen that is recognized by the immune system (e.g., by an antibody, an immunoglobulin receptor, a B cell receptor, or a T cell receptor). An epitope can be linear or conformational. Commonly, an epitope is a polypeptide or polysaccharide in a naturally occurring antigen. In artificial antigens it can be a low molecular weight substance such as an arsanilic acid derivative.

T-cells and B-cells recognize antigens in different ways. T-cells recognize peptide fragments of proteins that are embedded in class-II or class-I MHC molecules at the surface of cells, whereas B-cells recognize surface features of an unprocessed antigen, via immunoglobulin-like cell surface receptors. The difference in antigen recognition mechanisms of T-cells and B-cells are reflected in the different natures of their epitopes. Thus, whereas B-cells recognize surface features of an antigen or a pathogen, T-cell epitopes (which comprise peptides of about 8-12 amino acids in length) can be "internal" as well as "surface" when viewed in the context of the three-dimensional structure of the antigen. Accordingly, a B-cell epitope is preferably exposed on the surface of the antigen or pathogen, and can be linear or conformational, whereas a T-cell epitope is typically linear but is not required to be available or on the surface of the antigen. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids.

When an individual is immunized with a polypeptide antigen having multiple epitopes, in many instances the majority of responding T lymphocytes will be specific for one or a few linear epitopes from that antigen and/or a majority of the responding B lymphocytes will be specific for one or a few linear or conformational epitopes from that antigen. Such epitopes are typically referred to as "immunodominant epitopes." In an antigen having several immunodominant epitopes, a single epitope may be most dominant, and is typically referred to as the "primary" immunodominant epitope. The remaining immunodominant epitopes are typically referred to as "secondary" immunodominant epitope(s).

The term "fusion polypeptide" refers to a single polypeptide in which the amino acid sequence is derived from at least two different naturally occurring proteins or polypeptide chains.

The term "naked" as used herein refers to nucleic acids that are substantially free of other macromolecules, such as lipids, polymers, and proteins. A "naked" nucleic acid, such as a self-replicating RNA, is not formulated with other macromolecules to improve cellular uptake. Accordingly, a naked nucleic acid is not encapsulated in, absorbed on, or bound to a liposome, a microparticle or nanoparticle, a cationic emulsion, and the like.

As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate.

The term "pathogen" refers to a virus, eukaryote, prokaryote or archaea that is capable of proliferation, and causes a disease or illness in a host organism, such as a vertebrate (e.g., a mammal). A pathogen can be a viral, bacterial, protozoan, or fungal species, as well as a multi-cellular parasitic species. As used herein, two epitopes are from the same pathogen when the two epitopes are from the same pathogen species, but not necessarily from the same strain, serotype, clade, etc. Therefore, the two epitopes can be from two different subspecies, strains, or serotypes of the same pathogen (e.g., one epitope from H1N1 influenza virus, the other epitope from H3N2 influenza virus; one epitope from HIV-1 Clade B, the other epitope from HIV-1 Clade C; etc.).

As used herein, a "polypeptide antigen" refers to a polypeptide comprising one or more epitopes (either linear, conformational or both), that elicits an immunological response. Polypeptide antigens include, for example, a naturally-occurring protein, a mutational variant of a naturally-occurring protein (e.g., a protein that has amino acid substitution(s), addition(s), or deletion(s)), a truncated form of a naturally-occurring protein (e.g., an intracellular domain or extracellular domain of a membrane-anchored protein), as well as a fusion protein (a protein that is derived from at least two different naturally occurring proteins or polypeptide chains). In addition, polypeptide antigens also encompass polypeptides that comprise one or more amino acid stereoisomers, derivatives, or analogues. For example, amino acid derivatives include, e.g., chemical modifications of amino acids such as alkylation, acylation, carbamylation, iodination, etc Amino acid analogues include, e.g., compounds that have the same basic chemical structure as a naturally occurring amino acid, such as homoserine, norleucine, methionine sulfoxide, methionine methyl sulfonium. Polypeptide antigens also encompass polypeptides that are modified post-translationally (such as acetylated, phosphorylated, or glycosylated polypeptides). Therefore, an epitope of a polypeptide antigen is not limited to a peptide. For example, an epitope of a glycosylated polypeptide may be a saccharide group that is attached to the polypeptide chain.

Two protein antigens are "substantially the same" if the amino acid sequence identify between the two antigens is at least about 90%, at least about 95%, at least about 96%, at least about 97%, at least about 98%, or at least about 99%, across the length of the shorter antigen.

The terms "treat," "treating" or "treatment", as used herein, include alleviating, abating or ameliorating disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments The term "viral replicon particle" or "VRP" refers to recombinant infectious virions that cannot generate infectious progeny because of deletion of structural gene(s).

The term "virus-like particle" or "VLP" refers to a structure formed by viral coat proteins (e.g., a capsid) and optionally an evelope, but having no genetic material. A VLP resembles a viral particle.

EXEMPLIFICATION

The invention now being generally described, it will be more readily understood by reference to the following examples, which are included merely for purposes of illustration of certain aspects and embodiments of the present invention, and are not intended to limit the invention.

Methods:

RNA Synthesis

Plasmid DNA encoding alphavirus replicons (see sequences, vA317, vA17, vA336, vA160, vA322, vA311, vA306, vA142, vA526, vA527, vA318, vA140, vA318, vA372, vA368, vA369) served as a template for synthesis of RNA in vitro. Replicons contain the genetic elements required for RNA replication but lack those encoding gene products necessary for particle assembly; the structural genes of the alphavirus genome are replaced by sequences encoding a heterologous protein. Upon delivery of the replicons to eukaryotic cells, the positive-stranded RNA is translated to produce four non-structural proteins, which together replicate the genomic RNA and transcribe abundant subgenomic mRNAs encoding the heterologous gene product. Due to the lack of expression of the alphavirus structural proteins, replicons are incapable of inducing the generation of infectious particles. A bacteriophage (T7 or SP6) promoter upstream of the alphavirus cDNA facilitates the synthesis of the replicon RNA in vitro and the hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion, Austin, Tex.). Following transcription, the template DNA was digested with TURBO™ DNASE enzyme (Ambion, Austin, Tex.). The replicon RNA was precipitated with LiCl and reconstituted in nuclease-free water. Uncapped RNA was capped post-transcripionally with Vaccinia Capping Enzyme (VCE) using the SCRIPTCAP™ $m^7G$ Capping System (Epicentre Biotechnologies, Madison, Wis.) as outlined in the user manual. Post-transcriptionally capped RNA was precipitated with LiCl and reconstituted in nuclease-free water. The concentration of the RNA samples was determined by measuring the optical density at 260 nm. Integrity of the in vitro transcripts was confirmed by denaturing agarose gel electrophoresis.

LNP Formulation 1,2-dilinoleyloxy-N,N-dimethyl-3-aminopropane (DlinDM A) was synthesized using a previously published procedure [Heyes, J., Palmer, L., Bremner, K., MacLachlan, I. Cationic lipid saturation influences intracellular delivery of encapsulated nucleic acids. Journal of Controlled Release, 107: 276-287 (2005)]. 1, 2-Diastearoyl-sn-glycero-3-phosphocholine (DSPC) was purchased from Genzyme. Cholesterol was obtained from Sigma-Aldrich (St. Lois, Mo.). 1, 2-dimyristoyl-sn-glycero-3-phosphoethanolamine-N-[methoxy(polyethylene glycol)-2000] (ammonium salt) (PEG DMG 2000), 1, 2-dimyristoyl-sn-glycero-3-phosphoethanolamine-N-[methoxy(polyethylene glycol)-2000] (ammonium salt) (PEG DMG 1000) and 1, 2-dimyristoyl-sn-glycero-3-phosphoethanolamine-N-[methox-y(polyethylene glycol)-2000] (ammonium salt) (PEG DMG 3000) were obtained from Avanti Polar Lipids (Alabaster, Ala.). 1,2-dioleoyl-3-trimethylammonium-propane (chloride salt) (DOTAP) and 3134N—(N',N-dimethylaminoethane)-carbamoyl]cholesterol hydrochloride (DC-chol) were obtained from Avanti Polar Lipids. Proprietary lipids RV03, RV04, RV05, RV06, RV07, RV08, RV09, RV 10, RV11, RV12, RV15, were made as previously described in WO 2011/076807, which disclosed the lipids and methods for making them. Lipid RVO2 can be prepared according to known methods including the methods disclosed in WO 2011/057020. For example by substituting the alpha-amino and carbonyl of NorArgenine with a long chain alkenoyl and a long chain alkylamino, respectively. RVO2 has the structure

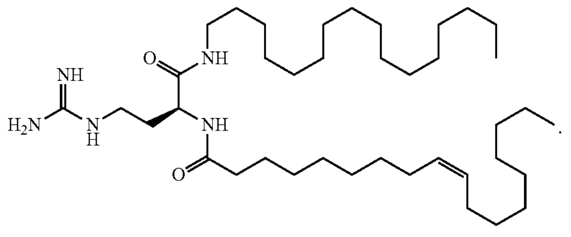 [SMILES: CCCCCCCC/C=C\CCCCCCCC(=O)N[C@@H](CCNC(=N)N)C(=O)NCCCCCCCCCCCCCCCC]

LNPs were formulated using three methods:

Method A (40 μg Batch, No Mustang, No Second Mixing, No TFF, with Dialysis)

Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 120.9 μL of the stock was added to 1.879 mL ethanol to make a working lipid stock solution of 2 mL. This amount of lipids was used to form LNPs with 40 μg RNA at a 8:1 N:P (Nitrogen to Phosphate) ratio. The protonatable nitrogen on DlinDMA (the cationic lipid) and phosphates on the RNA are used for this calculation. Each[t]g of self-replicating RNA molecule was assumed to contain 3 nmoles of anionic phosphate, each μg of DlinDMA was assumed to contains 1.6 nmoles of cationic nitrogen. A 2 mL working solution of RNA was also prepared from a stock solution of 1 μg/μL in 100 mM citrate buffer (pH 6) (Teknova). Three 20 mL glass vials (with stir bars) were rinsed with RNASE AWAY® solution (Molecular BioProducts) and washed with plenty of MILLI-Q ° water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3cc luer-lok syringes (BD Medical). 2 mL of citrate buffer (pH 6) was loaded in another 3 cc syringe. Syringes containing RNA and the lipids were connected to a T mixer (PEEK™ 500 p.m ID junction) using FEP tubing([fluorinated ethylene-propylene] 2 mm ID x 3 mm OD, Idex Health Science, Oak Harbor, Wash.). The outlet from the T mixer was also FEP tubing (2 mm ID x 3 mm). The third syringe containing the citrate buffer was connected to a separate piece of tubing (2 mm ID x 3 mm OD). All syringes were then driven at a flow rate of 7 mL/min using a syringe pump (from kdScientific, model no. KDS-220). The tube outlets were positioned to collect the mixtures in a 20 mL glass vial (while stirring). Next, LNPs were loaded into SLIDE-A-LYZER™ Dialysis Cassettes (Thermo Scientific, extra strength, 0.5-3 mL capacity) and dialyzed against 400-500 mL of 1×PBS (diluted from 10X ACCUGENE® PBS, from Lonza) overnight at 4° C. in an autoclaved plastic container before recovering the final product. For in vitro and in vivo experiments, formulations were diluted to the required RNA concentration with 1×PBS (from Teknova).

pKas

Unless explicitly indicated otherwise, all pKas referred to herein are measured in water at standard temperature and pressure. Also, unless otherwise indicated, all references to pKa are references to pKa measured using the following technique. 2 mM solution of lipid in ethanol are prepared by weighing the lipid and then dissolving in ethanol. 0.3 mM solution of fluorescent probe TNS in ethanol:methanol 9:1 is prepared by first making 3 mM solution of TNS in methanol and then diluting to 0.3 mM with ethanol.

An aqueous buffer containing sodium phosphate, sodium citrate, sodium acetate and sodium chloride, at the concentrations 20 mM, 25 mM, 20 mM and 150 mM, respectively, is prepared. The buffer is split into eight parts and the pH adjusted either with 12N HCl or 6N NaOH to 4.44-4.52, 5.27, 6.15-6.21, 6.57, 7.10-7.20, 7.72-7.80, 8.27-8.33 and 10.47-11.12. 400 uL of 2 mM lipid solution and 800 uL of 0.3 mM TNS solution are mixed.

Using the Tecan Genesis RSP 150 high throughput liquid handler and Gemini Software, 7.5 uL of probe/lipid mix are added to 242.5 uL of buffer in a 1 mL 96 well plate (model NUNC 260252, Nalgae Nunc International). This is done with all eight buffers.

After mixing in 1 mL 96 well plate, 100 uL of each probe/lipid/buffer mixture is transferred to a 250 uL black with clear bottom 96 well plate (model COSTAR 3904, Corning). The fluorescence measurements are carried out on the SPECTRAMAX M5 spectrophotometer using software SoftMax pro 5.2 and following parameters:

Read Mode: Fluorescence, Top read

Wavelengths: Ex 322 nm, Em 431 nm, Auto Cutoff On 420 nm

Sensitivity: Readings 6, PMT: Auto

Automix: Before: Off

Autocalibrate: On

Assay plate type: 96 Well Standard clrbtm

Wells to read: Read entire plate

Settling time: Off

Column Way. Priority: Column priority

Carriage Speed: Normal

Auto read: Off

After the measurement, the background fluorescence value of an empty well on the 96 well plate is subtracted from each probe/lipid/buffer mixture. The fluorescence intensity values are then normalized to the value at lowest pH. The normalized fluorescence intensity vs. pH chart is then plotted in the Microsoft Excel software. The eight points are connected with a smooth line.

The point on the line at which the normalized fluorescence intensity is equal to 0.5 is found. The pH corresponding to normalized fluorescence intensity equal to 0.5 is found and is considered the pKa of the lipid.

Method B (75 μg Batch, PES Hollow Fibers and No Mustang):

Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. This amount of lipids was used to form LNPs with 75 μg RNA at a 8:1 N:P (Nitrogen to Phosphate) ratio. The protonatable nitrogen on DlinDMA (the cationic lipid) and phosphates on the RNA are used for this calculation. Each μg of self-replicating RNA molecule was assumed to contain 3 nmoles of anionic phosphate, each μg of DlinDMA was assumed to contains 1.6 nmoles of cationic nitrogen. A 2 mL working solution of RNA was also prepared from a stock solution of 1 μg/μL in 100 mM citrate buffer (pH 6) (Teknova). Three 20 mL glass vials (with stir bars) were rinsed with RNASE AWAY® solution (Molecular BioProducts) and washed with plenty of MILLI-Q® water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3cc luer-lok syringes (BD Medical). 2 mL of citrate buffer (pH 6) was loaded in another 3 cc syringe. Syringes containing RNA and the lipids were connected to a T mixer (PEEK™ 500 p.m ID junction) using FEP tubing([fluorinated ethylene-propylene] 2 mm ID x 3 mm OD, Idex Health Science, Oak Harbor, Wash.). The outlet from the T mixer was also FEP tubing (2 mm ID x 3 mm). The third syringe containing the citrate buffer was connected to a separate piece of tubing (2 mm ID x 3 mm OD). All syringes were then driven at a flow rate of 7 mL/min using a syringe pump (from kdScientific, model no. KDS-220). The tube outlets were positioned to collect the mixtures in a 20 mL glass vial (while stirring). The stir bar was taken out and the ethanol/aqueous solution was allowed to equilibrate to room temperature for 1 h.

Then the mixture was loaded in a 5 cc syringe (BD Medical), which was fitted to a piece of FEP tubing (2 mm ID x 3 mm OD) and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, LNPs were concentrated to 2 mL and dialyzed against 10-15 volumes of 1×PBS (from Teknova) using the Tangential Flow Filtration (TFF) system before recovering the final product. The TFF system and hollow fiber filtration membranes were purchased from Spectrum Labs and were used according to the manufacturer's guidelines. Polyethersulfone (PES) hollow fiber filtration membranes (part number P-C1-100E-100-01N) with a 100 kD pore size cutoff and 20 $cm^2$ surface area were used. For in vitro and in vivo experiments, formulations were diluted to the required RNA concentration with 1×PBS (from Teknova).

Method C (75 μg Batch, with Mustang and PES Hollow Fibers):

Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. This amount of lipids was used to form LNPs with 75 μg RNA at a 8:1 N:P (Nitrogen to Phosphate) ratio. The protonatable nitrogen on DlinDMA (the cationic lipid) and phosphates on the RNA are used for this calculation. Each μg of self-replicating RNA molecule was assumed to contain 3 nmoles of anionic phosphate, each μg of DlinDMA was assumed to contains 1.6 nmoles of cationic nitrogen. A 2 mL working solution of RNA was also prepared from a stock solution of 1 μg/μL in 100 mM citrate buffer (pH 6) (Teknova). Three 20 mL glass vials (with stir bars) were rinsed with RNASE AWAY® solution (Molecular BioProducts) and washed with plenty of MILLI-Q® water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3cc luer-lok syringes (BD Medical). 2 mL of citrate buffer (pH 6) was loaded in another 3 cc syringe. Syringes containing RNA and the lipids were connected to a T mixer (PEEK™ 500 p.m ID junction) using FEP tubing([fluorinated ethylene-propylene] 2 mm ID x 3 mm OD, Idex Health Science, Oak Harbor, Wash.). The outlet from the T mixer was also FEP tubing (2 mm ID x 3 mm). The third syringe containing the citrate buffer was connected to a separate piece of tubing (2 mm ID x 3 mm OD). All syringes were then driven at a flow rate of 7 mL/min using a syringe pump (from kdScientific, model no. KDS-220). The tube outlets were positioned to collect the mixtures in a 20 mL glass vial (while stirring). The stir bar was taken out and the ethanol/aqueous solution was allowed to equilibrate to room temperature for 1 h. Then the mixture was loaded in a 5 cc syringe (BD Medical), which was fitted to a piece of FEP tubing (2 mm ID x 3 mm OD) and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, the mixture collected from the second mixing step (LNPs) were passed through MUSTANG® Q membrane (an anion-exchange support that binds and removes anionic molecules, obtained from Pall Corporation, AnnArbor, MI, USA). Before passing the LNPs, 4 mL of 1 M NaOH, 4 mL of 1 M NaCl and 10 mL of 100 mM citrate buffer (pH 6) were successively passed through the Mustang membrane. LNPs were warmed for 10 min at 37° C. before passing through the mustang filter. Next, LNPs were concentrated to 2 mL and dialyzed against 10-15 volumes of 1×PBS (from Teknova) using the Tangential Flow Filtration (TFF) system before recovering the final product. The TFF system and hollow fiber filtration membranes were purchased from Spectrum Labs and were used according to the manufacturer's guidelines. Polyethersulfone (PES) hollow fiber filtration membranes (part number P-C1-100E-100-01N) with a 100 kD pore size cutoff and 20 $cm^2$ surface area were used. For in vitro and in vivo experiments, formulations were diluted to the required RNA concentration with 1×PBS (from Teknova).

CNE Formulations

CNEs were prepared similar to charged MF59 as previously described (Ott et al., Journal of Controlled Release, volume 79, pages 1-5, 2002), with one major modification for CMF34. DOTAP was dissolved in the squalene directly, and no organic solvent was used. It was discovered that inclusion of a solvent in emulsions that contained greater than 1.6 mg/ml DOTAP produced a foamy feedstock that could not be microfluidized to produce an emulsion. Heating squalene to 37° C. allowed DOTAP to be directly dissolved in squalene, and then the oil phase could be successfully dispersed in the aqueous phase (e.g., by homogenization) to produce an emulsion.

TABLE 3

| CNE | Cationic Lipid mg/mL | Surfactant | Squalene | oil:Lipid ratio (mole: mole) | Aqueous phase |
|---|---|---|---|---|---|
| CNE13 | DDA (in DCM) 1.45 | 0.5% SPAN 85 0.5% Tween 80 | 4.3% | 10 mM citrate buffer pH 6.5 | DDA (in DCM) |
| CNE17 | DOTAP (in DCM) 1.4 | 0.5% SPAN 85 0.5% Tween 80 | 4.3% | 52.4:1 | 10 mM citrate buffer pH 6.5 |
| CMF34 | DOTAP (no organic solvent) 4.4 | 0.5% SPAN 85 0.5% Tween 80 | 4.3% | 16.7:1 | 10 mM citrate buffer pH 6.5 |

RNA Complexation

The number of nitrogens in solution was calculated from the cationic lipid concentration, DOTAP for example has 1 nitrogen that can be protonated per molecule. The RNA concentration was used to calculate the amount of phosphate in solution using an estimate of 3 nmols of phosphate per microgram of RNA. By varying the amount of RNA:Lipid, the N/P ratio can be modified. RNA was complexed to the CNEs in a range of nitrogen/phosphate ratios (N/P). Calculation of the N/P ratio was done by calculating the number of moles of protonatable nitrogens in the emulsion per milliliter. To calculate the number of phosphates, a constant of 3 nmols of phosphate per microgram of RNA was used.

After the values were determined, the appropriate ratio of the emulsion was added to the RNA. Using these values, the RNA was diluted to the appropriate concentration and added directly into an equal volume of emulsion while vortexing lightly. The solution was allowed to sit at room temperature for approximately 2 hours. Once complexed the resulting solution was diluted to the appropriate concentration and used within 1 hour.

Particle Size

Particle size was measured using a ZETASIZER™ Nano ZS zeta potential analyzer (Malvern Instruments, Worcestershire, UK) according to the manufacturer's instructions. Particle sizes are reported as the Z average with the polydispersity index (pdi). Liposomes were diluted in 1×PBS before measurement.

Encapsulation Efficiency and RNA Concentration

The percentage of encapsulated RNA and RNA concentration were determined by QUANT-IT™ RIBOGREEN® RNA reagent kit (Invitrogen). Manufacturer's instructions were followed in the assay. The ribosomal RNA standard provided in the kit was used to generate a standard curve. LNPs were diluted ten fold or one hundred fold in 1*x* TE buffer (from kit), before addition of the dye. Separately, LNPs were diluted ten or 100 fold in 1X TE buffer containing 0.5% TRITON™ X surfactant (Sigma-Aldrich), before addition of the dye. Thereafter an equal amount of dye was added to each solution and then 180 μL of each solution after dye addition was loaded in duplicate into a 96 well tissue culture plate (obtained from VWR, catalog #353072). The fluorescence (Ex 485 nm, Em 528 nm) was read on a microplate reader (from BioTek Instruments, Inc.).

TRITON™ X surfactant was used to disrupt the LNPs, providing a fluorescence reading corresponding to the total RNA amount and the sample without TRITON™ X surfactant provided fluorescence corresponding to the unencapsulated RNA. % RNA encapsulation was determined as follows: LNP RNA Encapsulation (%)=[($F_t$—$F_i$)/$F_t$] X 100, where $F_t$ is the fluorescence intensity of LNPs with TRITON™ X surfactant addition and $F_i$ is the fluorescence intensity of the LNP solution without detergent addition. These values ($F_t$ and $F_1$) were obtained after subtraction from blank (1X TE buffer) fluorescence intensity. The concentration of encapsulated RNA was obtained by comparing $F_t$—$F_i$, with the standard curve generated. All LNP formulations were dosed in vivo based on the encapsulated dose.

Gel Electrophoresis

Denaturing gel electrophoresis was performed to evaluate the integrity of the RNA after the formulation process and to assess the RNAse protection of the encapsulated RNA. The gel was cast as follows: 0.4 g of agarose (Bio-Rad, Hercules, Calif.) was added to 36 ml of DEPC treated water and heated in a microwave until dissolved and then cooled until warm. 4 ml of 10x denaturing gel buffer (Ambion, Austin, Tex.), was then added to the agarose solution. The gel was poured and was allowed to set for at least 30 minutes at room temperature. The gel was then placed in a gel tank, and 1× NORTHERNMAX® running buffer (Ambion, Austin, Tex.) was added to cover the gel by a few millimeters.

RNase Protection Assay

RNase digestion was achieved by incubation with 3.8mAU of RNase A per microgram of RNA (Ambion, Hercules, and CA) for 30 minutes at room temperature. RNase was inactivated with Protenase K (Novagen, Darmstadt, Germany) by incubating the sample at 55° C. for 10 minutes. Post RNase inactivation, a 1:1 v/v mixture of sample to 25:24:1 v/v/v, phenol: chloroform: isoamyl alcohol was added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion MILLENIUM™ markers were used to approximate the molecular weight of the RNA construct. The gel was run at 90 V. The gel was stained using 0.1% SYBR gold according to the manufacturer's guidelines (Invitrogen, Carlsbad, Calif.) in water by rocking at room temperature for 1 hour. Gel images were taken on a Bio-Rad CHEMIDOC™ XRS imaging system (Hercules, Calif.).

Secreted Alkaline Phosphatase (SEAP) Assay

To assess the kinetics and amount of antigen production in vivo, an RNA replicon encoding for SEAP was administered with and without formulation to mice via intramuscularly injection. Groups of 5 female BALB/c mice aged 8-10 weeks and weighing about 20 g were immunized with liposomes encapsulating RNA encoding for SEAP. Naked RNA was administered in RNase free 1×PBS. As a positive control, viral replicon particles (VRPs) at a dose of $5\times10^5$ infectious units (IU) were also sometimes administered. A 100 μl dose was administered to each mouse (50 μl per site) in the quadriceps muscle. Blood samples were taken 1, 3, and 6 days post injection. Serum was separated from the blood immediately after collection, and stored at −30° C. until use.

A chemiluminescent SEAP assay PHOSPHA-LIGHT™ System (Applied Biosystems, Bedford, Mass.) was used to analyze the serum. Mouse sera were diluted 1:4 in 1X PHOSPHA-LIGHT™ dilution buffer. Samples were placed in a water bath sealed with aluminum sealing foil and heat inactivated for 30 minutes at 65° C. After cooling on ice for 3 minutes, and equilibrating to room temperature, 50 µL of Phospha PHOSPHA-LIGHT™ assay buffer was added to the wells and the samples were left at room temperature for 5 minutes. Then, 50 µL of reaction buffer containing 1:20 CSPD® (chemiluminescent alkaline phosphate substrate) substrate was added, and the luminescence was measured after 20 minutes of incubation at room temperature. Luminescence was measured on a Berthold Centro LB 960 luminometer (Oak Ridge, Tenn.) with a 1 second integration per well. The activity of SEAP in each sample was measured in duplicate and the mean of these two measurements taken.

Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al. (2003) An alphavirus replicon particle chimera derived from venezuelan equine encephalitis and sindbis viruses is a potent gene-based vaccine delivery vector. J Virol 77: 10394-10403. In this system, the antigen (or reporter gene) replicons consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri et al). These replicons were packaged into VRPs by co-electroporating them into baby hamster kidney (BHK) cells along with defective helper RNAs encoding the Sindbis virus capsid and glycoprotein genes (see FIG. 2 of Perri et al., J. Virol. 77: 10394-10403 (2003)). The VRPs were then harvested and titrated by standard methods and inoculated into animals in culture fluid or other isotonic buffers.

RSV-F Trimer Subunit Vaccine

The RSV F trimer is a recombinant protein comprising the ectodomain of RSV F with a deletion of the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed in insect cells and purified by virtue of a HIS-tagged in fusion with the construct's C-terminus followed by size exclusion chromatography using conventional techniques. The resulting protein sample exhibits greater than 95% purity. For the in vivo evaluation of the F-subunit vaccine, 100 ng/mL trimer protein was adsorbed on 2 mg/mL alum using 10 mM Histidine buffer, pH 6.3 and isotonicity adjusted with sodium chloride to 150 mM. F-subunit protein was adsorbed on alum overnight with gentle stirring at 2-8° C.

Murine Immunogenicity Studies

Groups of 10 female BALB/c mice aged 8-10 weeks and weighing about 20 g were immunized at day 0 and day 21 with bleeds taken at days 14, 35 and 49. All animals were injected in the quadriceps in the two hind legs each getting an equivalent volume (50 µl per site). When measurement of T cell responses was required, spleens were harvested at day 35 or 49.

Vaccination and Challenge of Cotton Rats

Female cotton rats (*Sigmodon hispidis*) were obtained from Harlan Laboratories. All experiments were approved and performed according to Novartis Animal Care and Use Committee. Groups of animals were immunized intramuscularly (i.m., 100 µl) with the indicated vaccines on days 0 and 21. Serum samples were collected 2 weeks after each immunization. Immunized or unvaccinated control animals were challenged intranasally (i.n.) with $1\times10^5$ PFU RSV 4 weeks after the final immunization. Blood collection and RSV challenge were performed under anesthesia with 3% isoflurane using a precision vaporizer.

RSV F-Specific ELISA

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F in PBS. After washing (PBS with 0.1% TWEEN-20® surfactant), plates were blocked with Superblock Blocking Buffer in PBS (Thermo Scientific) for at least 1.5 hr at 37° C. The plates were then washed, serial dilutions of serum in assay diluent (PBS with 0.1% TWEEN-20® surfactant and 5% goat serum) from experimental or control cotton rats were added, and plates were incubated for 2 hr at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to standard, pooled sera from RSV-infected cotton rats with a defined titer of 1:2500, that was included on every plate).

RSV Micro Neutralization Assay

Serum samples were tested for the presence of neutralizing antibodies by a plaque reduction neutralization test (PRNT). Two-fold serial dilutions of HI-serum (in PBS with 5% HI-FBS) were added to an equal volume of RSV Long previously titered to give approximately 115 PFU/25 µl. Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hr at 37° C. and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

CMV Micro Neutralization Assay

Serum samples were tested for the presence of neutralizing antibodies by an infection reduction neutralization test. Two-fold serial dilutions of HI-serum (in DMEM with 10% HI FBS) were added to an equal volume of CMV (strain TB40 or clinical isolate 8819) previously titered to give approximately 200 IU/50 µl. Serum/virus mixtures were incubated for 2 hours at 37° C. and 5% CO2, to allow virus neutralization to occur, and then 50 µl of this mixture (containing approximately 200 IU) was inoculated on duplicate wells of ARPE-19 cells in 96 half well plates. Plates were incubated for 40-44 hours. The number of positive infected foci was determined by immunostaining with an AlexaFluor 488 conjugated TEl CMV monoclonal antibody followed by automated counting. The neutralization titer is defined as the reciprocal of the serum dilution producing a 50% reduction in number of positive virus foci per well, relative to controls (no serum).

Bovine Immunogenicity Studies

Twenty colostrum deprived Holstein/Holstein cross calves were used in the study. All calves were male. Animals were obtained from J & R, a local supplier and double ear-tagged for identification, as per site procedures. Initially, there was no intent to castrate and dehorn, however, when the study was extended to include $3^{rd}$ and $4^{th}$ vaccinations, these procedures were performed to help ensure animal and handler safety. The procedures were performed in accordance with RAC SOPs. The procedures were done at a time felt to have the least impact on the study results. All calves were prescreened prior to the beginning of the study, and were seronegative for BRSV via a serum neutralization assay. Seronegative calves were defined as those having titers of ≤1:4 titer to BRSV in a constant virus, decreasing serum neutralization (SN) assay with 50-500 Tissue Culture Infective $Dose_{50}$ ($TCID_{50}$) BRSV. Calves were also screened prior to acquisition, for persistent infection with Bovine Virus Diarrhea Virus (BVDV) Immunohistochemistry (IHC) testing of ear notch samples was performed with all negative results.

Calves (5 per group) were given intramuscular vaccinations on days 0, 21, 86 and 146. RNA and PBS vaccines were administered as 1.0 mL split doses on each side of the neck (2 mL total dose). The Triangle 4 product was administered as labeled (2.0 mL dose on one side of the neck). The RSV-F subunit protein vaccine (15 μg) adjvuanted with MF59 was administered as 1.0 mL split doses on each side of the neck (2 mL total dose). Serum was collected for antibody analysis on days 0, 14, 21, 35, 42, 56, 63, 86, 100, 107, 114, 121, 128, 135, 146, 160, 167, 174, 181, 188, 195, and 202.

Example I

Co-Administration of RNA and Protein to Mice

In this example, an RNA molecule encoding the RSV-F, or an RNA molecule encoding the GFP protein, was co-administered with an RSV-F antigen in polypeptide form. The effects of RNA on its "cognate" antigen and "non-cognate" antigen were assessed. The RSV-F antigen is a "non-cognate" antigen of the GFP-coding RNA because the F antigen does not share sequence homology to, and does not immunologically cross-react with the polypeptide encoded by the RNA molecule (GFP).

Three RNAs were used for this study: the vA317 replicon that expresses the surface fusion glycoprotein of RSV (RSV-F); the vA17 replicon that expresses green fluorescent protein (GFP); and the vA336 replicon that is replication-defective and encodes GFP. BALB/c mice, 5 animals per group, were given bilateral intramuscular vaccinations (50 μL per leg) on days 0 and 21. Spleens were harvested at day 49 for T cell analysis. Animals, 70 total, were divided into 14 groups (5 animals per group):

Group 1 were given bilateral intramuscular vaccinations (50 μL per leg) on days 0, 21 with VRPs ($1\times10^6$ IU) expressing the full-length wild type surface fusion glycoprotein of RSV.

Group 2 were given bilateral intramuscular vaccinations (50 μL per leg) on days 0, 21 with the RSV-F subunit protein (5 μg).

Group 3 were given bilateral intramuscular vaccinations (50 μL per leg) on days 0, 21 with the RSV-F subunit protein vaccine (5 μg) adjuvanted with alum and a small molecule TLR7 agonist (TLR7A, 25 μg).

Group 4 were given bilateral intramuscular vaccinations (50 μL per leg) on days 0, 21 with RSV-F subunit protein (5 μg) mixed with self-replicating RNA (vA317, 1 μg, RSV-F) which had been formulated with CNE17 (prior to protein addition at an N:P raio of 10:1).

Group 5 were given bilateral intramuscular vaccinations (50 μL per leg) on days 0, 21 with RSV-F subunit protein (5 μg) mixed with self-replicating RNA (vA317, 1 μg, RSV-F) which had been formulated with LNPs (RV01(36)). The LNP had the following composition: 40% DlinDMA, 10% DSPC, 48% Chol, 2% PEG DMG 2000 and an N:P ratio of 8:1. They were made using Method A, except a 150 μg RNA batch size was used.

Group 6 were given bilateral intramuscular vaccinations (50 μL per leg) on days 0, 21 with RSV-F subunit protein (5 μg) mixed with empty LNPs (RV01(36)), made as per group 5). The lipid dose was equivalent to the dose of the LNP formulation in group 9 and 12 which contained 0.01 μg RNA.

Group 7 were given bilateral intramuscular vaccinations (50 μL per leg) on days 0, 21 with RSV-F subunit protein (5 μg) mixed with empty LNPs (RV01(36)), made as per group 5). The lipid dose was equivalent to the dose of the LNP formulation in group 10 and 13 which contained 0.1 μg RNA.

Group 8 were given bilateral intramuscular vaccinations (50 μL per leg) on days 0, 21 with RSV-F subunit protein (5 μg) mixed with empty LNPs (RV01(36)), made as per group 5). The lipid dose was equivalent to the dose of the LNP formulation in group 11 and 14 which contained 1.0 μg RNA.

Group 9 were given bilateral intramuscular vaccinations (50 μL per leg) on days 0, 21 with RSV-F subunit protein (5 μg) mixed with self-replicating RNA (vA17, 1 μg, GFP) formulated with LNPs (RV01(36)), made as per group 5). The lipid dose was equivalent to the dose of the LNP formulation in groups 6 and 12.

Group 10 were given bilateral intramuscular vaccinations (50 μL per leg) on days 0, 21 with RSV-F subunit protein (5 μg) mixed with self-replicating RNA (vA17, 1 μg, GFP) formulated with LNPs (RV01(36)), made as per group 5). The lipid dose was equivalent to the dose of the LNP formulation in groups 7 and 13.

Group 11 were given bilateral intramuscular vaccinations (50 μL per leg) on days 0, 21 with RSV-F subunit protein (5 μg) mixed with self-replicating RNA (vA17, 1 μg, GFP) formulated with LNPs (RV01(36), made as per group 5). The lipid dose was equivalent to the dose of the LNP formulation in groups 8 and 14.

Group 12 were given bilateral intramuscular vaccinations (50 μL per leg) on days 0, 21 with RSV-F subunit protein (5 μg) mixed with non-replicating RNA (vA336, 1 μg, GFP) formulated with LNPs (RV01(36)), made as per group 5). The lipid dose was equivalent to the dose of the LNP formulation in groups 6 and 9.

Group 13 were given bilateral intramuscular vaccinations (50 μL per leg) on days 0, 21 with RSV-F subunit protein (5 μg) mixed with non-replicating RNA (vA317, 1 μg, GFP) formulated with LNPs (RV01(36), made as per group 5). The lipid dose was equivalent to the dose of the LNP formulation in groups 7 and 10.

Group 14 were given bilateral intramuscular vaccinations (50 μL per leg) on days 0, 21 with RSV-F subunit protein (5 μg) mixed with non-replicating RNA (vA317, 1 μg, GFP) formulated with LNPs (RV01(36), made as per group 5). The lipid dose was equivalent to the dose of the LNP formulation in groups 8 and 11.

Results and Conclusions

F-specific serum IgG titers are shown in tables I-1&2 (day 14) and I-3&4 (day 35). F-specific serum IgG1 titers are shown in tables I-5&6 (day 35) and F-specific serum IgG2a titers are shown in tables I-7-I-9 (day 35). RSV serum neutralizing antibody titers are shown in table I-10 (days 35 and 49). Average net F-specific cytokine-positive T cell frequencies (CD4+ or CD8+) are shown in Tables I-11 and 1-12.

This study showed that RNA formulated with LNP was a novel, potent adjuvant for recombinant protein (RSV F). LNP was tested without and with RNA (encoding GFP) as adjuvants for F protein. Serum antibodies and splenic T cells specific for F antigen were measured. The LNP RV01 (without RNA) was an adjuvant for F protein. RV01 formulated with GFP RNA was even more effective, indicating that both the LNP and the RNA components contribute to the adjuvanticity. RNA was needed to induce IgG2a, but not IgG1, indicating that LNP was not a "Th1" type adjuvant.

For the combination of protein (RSV F) and LNP/RNA, F RNA was compared to GFP RNA and to no RNA (LNP present in all). For antibody responses, there was relatively little difference between F RNA, GFP RNA, and no RNA, except for IgG2a, as noted above. However, F RNA induced superior CD8 T cell responses compared to GFP RNA or no RNA

TABLE I-1

F-specific serum IgG titers of BALB/c mice, 5 animals per group, 14 days after intramuscular vaccination. Data are represented as titers for individual mice and the geometric mean titers of 5 individual mice per group. If an individual animal had a titer of <25 (limit of detection), it was assigned a titer of 5.

| | dose/vaccine | | | | |
|---|---|---|---|---|---|
| | 1E6 IU VRP-VCR2.1-RSV-F-full | 5 μg RSV F | 5 μg RSV F/ 25 μg TLR7A/ alum | 5 μg RSV F + 1 μg vA317u/ CNE17 | 5 μg RSV F + 1 μg vA317u/ RV01(36) |
| F- | 1775 | 5 | 20850 | 1326 | 5464 |
| specific | 1976 | 5 | 13877 | 1816 | 14434 |
| serum | 3080 | 444 | 14239 | 2184 | 7587 |
| IgG titers | 1964 | 44 | 14590 | 1016 | 9180 |
| | 2003 | 5 | 19155 | 614 | 10938 |
| GMT | 2117 | 19 | 16302 | 1268 | 9031 |

TABLE I-2

Continued from Table I-1. F-specific serum IgG titers of BALB/c mice, 5 animals per group, 14 days after intramuscular vaccination. Data are represented as titers for individual mice and the geometric mean titers of 5 individual mice per group. If an individual animal had a titer of <25 (limit of detection), it was assigned a titer of 5.

| | dose/vaccine | | | | | | | | |
|---|---|---|---|---|---|---|---|---|---|
| | 5 μg RSV F + RV01(36) empty (0.01 μg) | 5 μg RSV F + RV01(36) empty (0.1 μg) | 5 μg RSV F + RV01(36) empty (1 μg) | 5 μg RSV F + 0.01 μg vA17u/ RV01(36) | 5 μg RSV F + 0.1 μg vA17u/ RV01(36) | 5 μg RSV F + 1 μg vA17u/ RV01(36) | 5 μg RSV F + 0.01 μg vA336u/ RV01(36) | 5 μg RSV F + 0.1 μg vA336u/ RV01(36) | 5 μg RSV F + 1 μg vA336u/ RV01(36) |
| F- | 5 | 5 | 1949 | 5 | 411 | 3412 | 5 | 478 | 1724 |
| specific | 5 | 53 | 4742 | 5 | 481 | 1835 | 37 | 641 | 3663 |
| serum | 5 | 37 | 2673 | 5 | 2727 | 1904 | 5 | 1115 | 4119 |
| IgG | 5 | 65 | 4133 | 218 | 447 | 2148 | 32 | 826 | 2759 |
| titers | 5 | 129 | 783 | 317 | 1207 | 2106 | 5 | 1043 | 2640 |
| GMT | 5 | 38 | 2402 | 24 | 781 | 2220 | 11 | 783 | 2854 |

TABLE I-3

F-specific serum IgG titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | |
|---|---|---|---|---|---|
| | 1E6 IU VRP-VCR2.1-RSV-F-full | 5 μg RSV F | 5 μg RSV F/ 25 μg TLR7A/ Alum | 5 μg RSV F + 1 μg vA317u/ CNE17 | 5 μg RSV F + 1 μg vA317u/ RV01(36) |
| F- | 34973 | 1712 | 256096 | 106631 | 137187 |
| specific | 27377 | 1528 | 233285 | 110416 | 195548 |
| serum | 46627 | 9472 | 372299 | 193437 | 177449 |
| IgG | 47593 | 10788 | 200553 | 65757 | 225507 |

TABLE I-3-continued

F-specific serum IgG titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | |
|---|---|---|---|---|---|
| | 1E6 IU VRP-VCR2.1-RSV-F-full | 5 μg RSV F | 5 μg RSV F/ 25 μg TLR7A/ Alum | 5 μg RSV F + 1 μg vA317u/ CNE17 | 5 μg RSV F + 1 μg vA317u/ RV01(36) |
| titers | 17089 | 7053 | 246051 | 106100 | 169730 |
| GMT | 32509 | 4519 | 255910 | 109704 | 178695 |

TABLE I-4

Continued from Table I-3. F-specific serum IgG titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | | | | | |
|---|---|---|---|---|---|---|---|---|---|
| | 5 μg RSV F + RV01(36) empty (0.01 μg) | 5 μg RSV F + RV01(36) empty (0.1 μg) | 5 μg RSV F + RV01(36) empty (1 μg) | 5 μg RSV F + 0.01 μg vA17u/ RV01(36) | 5 μg RSV F + 0.1 μg vA17u/ RV01(36) | 5 μg RSV F + 1 μg vA17u/ RV01(36) | 5 μg RSV F + 0.01 μg vA336u/ RV01(36) | 5 μg RSV F + 0.1 μg vA336u/ RV01(36) | 5 μg RSV F + 1 μg vA336u/ RV01(36) |
| F- | 1916 | 5300 | 148066 | 10130 | 49413 | 190336 | 5559 | 78946 | 182029 |
| specific | 462 | 56079 | 213010 | 18791 | 49915 | 215482 | 39933 | 93558 | 167670 |
| serum | 1197 | 7851 | 125433 | 19122 | 78043 | 199401 | 1694 | 77531 | 296722 |
| IgG | 67 | 27879 | 160137 | 39695 | 131798 | 186112 | 6422 | 117371 | 225668 |
| titers | 2746 | 28847 | 227934 | 66920 | 94756 | 287935 | 2973 | 155149 | 208995 |
| GMT | 721 | 17975 | 170574 | 24950 | 75194 | 212983 | 5905 | 100841 | 211890 |

TABLE I-5

F-specific serum IgG1 titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | |
|---|---|---|---|---|---|
| | 1E6 IU VRP-VCR2.1-RSV-F-full | 5 μg RSV F | 5 μg RSV F/ 25 μg TLR7A/ alum | 5 μg RSV F + 1 μg vA317u/ CNE17 | 5 μg RSV F + 1 μg vA317u/ RV01(36) |
| F- | 8215 | 1584 | 329326 | 159083 | 51705 |
| specific | 4591 | 2910 | 440698 | 149037 | 76049 |
| serum | 3224 | 17153 | 421048 | 250812 | 80830 |
| IgG1 | 7728 | 16701 | 272041 | 77892 | 90314 |
| titers | 3722 | 12119 | 368395 | 163630 | 120507 |
| GMT | 5114 | 6932 | 360919 | 149942 | 80871 |

TABLE I-6

Continued from Table I-5. F-specific serum IgG1 titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | | | | | |
|---|---|---|---|---|---|---|---|---|---|
| | 5 μg RSV F + RV01(36) empty (0.01 μg) | 5 μg RSV F + RV01(36) empty (0.1 μg) | 5 μg RSV F + RV01(36) empty (1 μg) | 5 μg RSV F + 0.01 μg vA17u/ RV01(36) | 5 μg RSV F + 0.1 μg vA17u/ RV01(36) | 5 μg RSV F + 1 μg vA17u/ RV01(36) | 5 μg RSV F + 0.01 μg vA336u/ RV01(36) | 5 μg RSV F + 0.1 μg vA336u/ RV01(36) | 5 μg RSV F + 1 μg vA336u/ RV01(36) |
| F- | 2974 | 5149 | 219778 | 11439 | 56323 | 135573 | 6937 | 76056 | 220841 |
| specific | 660 | 65459 | 513476 | 13986 | 55678 | 175715 | 55970 | 77182 | 229310 |

TABLE I-6-continued

Continued from Table I-5. F-specific serum IgG1 titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group.

| | dose/vaccine | | | | | | | | |
|---|---|---|---|---|---|---|---|---|---|
| | 5 μg RSV F + RV01(36) empty (0.01 μg) | 5 μg RSV F + RV01(36) empty (0.1 μg) | 5 μg RSV F + RV01(36) empty (1 μg) | 5 μg RSV F + 0.01 μg vA17u/ RV01(36) | 5 μg RSV F + 0.1 μg vA17u/ RV01(36) | 5 μg RSV F + 1 μg vA17u/ RV01(36) | 5 μg RSV F + 0.01 μg vA336u/ RV01(36) | 5 μg RSV F + 0.1 μg vA336u/ RV01(36) | 5 μg RSV F + 1 μg vA336u/ RV01(36) |
| serum | 1892 | 8250 | 208658 | 22003 | 91464 | 187477 | 2327 | 101123 | 276811 |
| IgG1 | 92 | 36886 | 242451 | 33160 | 100181 | 124329 | 8767 | 134221 | 268860 |
| titers | 3513 | 34019 | 318148 | 51696 | 61527 | 290264 | 3786 | 197059 | 213310 |
| GMT | 1038 | 20349 | 283034 | 22706 | 70712 | 174365 | 7859 | 109442 | 240461 |

TABLE I-7

F-specific serum IgG2a titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group. If an individual animal had a titer of <25 (limit of detection), it was assigned a titer of 5.

| | dose/vaccine | | | | |
|---|---|---|---|---|---|
| | 1E6 IU VRP-VCR2.1-RSV-F-full | 5 μg RSV F | 5 μg RSV F/ 25 μg TLR7A/ alum | 5 μg RSV F + 1 μg vA317u/ CNE17 | 5 μg RSV F + 1 μg vA317u/ RV01(36) |
| F- | 71930 | 5 | 79789 | 1489 | 299210 |
| specific | 66120 | 5 | 40013 | 6038 | 390179 |
| serum | 118752 | 539 | 236750 | 5253 | 316071 |
| IgG2a | 117259 | 457 | 60506 | 13828 | 354418 |
| titers | 34487 | 5 | 51464 | 14135 | 396302 |
| GMT | 74428 | 31 | 74877 | 6209 | 349070 |

TABLE I-8

Continued from Table I-7. F-specific serum IgG2a titers of BALB/c mice, 5 animals per group, intramuscular vaccinations on days 0 and 21. Serum was collected for antibody analysis on day 35 (2wp2). Data are represented as titers for individual mice and the geometric mean titers of 5 individual mice per group. If an individual animal had a titer of <25 (limit of detection), it was assigned a titer of 5.

| | dose/vaccine | | | | | | | | |
|---|---|---|---|---|---|---|---|---|---|
| | 5 μg RSV F + RV01(36) empty (0.01 μg) | 5 μg RSV F + RV01(36) empty (0.1 μg) | 5 μg RSV F + RV01(36) empty (1 μg) | 5 μg RSV F + 0.01 μg vA17u/ RV01(36) | 5 μg RSV F + 0.1 μg vA17u/ RV01(36) | 5 μg RSV F + 1 μg vA17u/ RV01(36) | 5 μg RSV F + 0.01 μg vA336u/ RV01(36) | 5 μg RSV F + 0.1 μg vA336u/ RV01(36) | 5 μg RSV F + 1 μg vA336u/ RV01(36) |
| F- | 5 | 41 | 5 | 525 | 40477 | 123780 | 282 | 73117 | 130968 |
| specific | 5 | 5 | 2397 | 10309 | 43203 | 58551 | 2618 | 73961 | 46273 |
| serum | 5 | 5 | 5 | 2278 | 68325 | 81341 | 284 | 47198 | 196773 |
| IgG2a | 5 | 268 | 5 | 7386 | 120738 | 115043 | 374 | 120915 | 138476 |
| titers | 630 | 34 | 5 | 18616 | 82748 | 159474 | 71 | 93851 | 138895 |
| GMT | 13 | 25 | 17 | 4424 | 65370 | 101580 | 355 | 78050 | 118060 |

TABLE I-9

| ratio of F-specific serum IgG2a:IgG1 titers | |
|---|---|
| Formulations | IgG2a:IgG1 ratio |
| F protein (5 mcg), benchmark 1 | 1:220 |
| F protein/Alum/TLR7A (25 mcg), benchmark 2 | 1:4.8 |
| VRP (1E6), benchmark 3 | 10:1 |
| F protein (5 mcg) + 1 mcg F RNA/Liposome | 5:1 |
| F protein (5 mcg) + 1 mcg F RNA/CNE17 | 1:25 |
| F protein (5 mcg) + 1 mcg GFP RNA/Liposome | 1:1.7 |
| F protein (5 mcg) + 1 mcg GFP RNA/CNE17 | 1:2.0 |
| F protein (5 mcg) + 0.01 mcg equivalent of liposome (without RNA) | 1:79 |
| F protein (5 mcg) + 0.1 mcg equivalent of liposome (without RNA) | 1:388 |
| F protein (5 mcg) + 1.0 mcg equivalent of liposome (without RNA) | 1:1204 |

TABLE I-10

RSV serum neutralization titers of BALB/c mice, 5 animals per group, after intramuscular vaccinations on days 0 and 21. Serum was collected for analysis on days 35 (2wp2) and 49 (4wp2). Data are represented as 60% plaque reduction neutralization titers of pools of 5 mice, 1 pool per group.

| | RSV serum neutralization titers | |
|---|---|---|
| dose/vaccine | 2wp2 | 4wp2 |
| 1E6 IU VRP-VCR2.1-RSV-F-full | 53 | 62 |
| 5 μg RSV F | <20 | 20 |
| 5 μg RSV F/25 μg TLR7A/alum | 1002 | 1703 |
| 5 μg RSV F + 1 μg vA317u/CNE17 | 531 | 352 |
| 5 μg RSV F + 1 μg vA317u/RV01(36) | 333 | 291 |
| 5 μg RSV F + RV01(36) empty (0.01 μg) | <20 | 24 |
| 5 μg RSV F + RV01(36) empty (0.1 μg) | <20 | 30 |
| 5 μg RSV F + RV01(36) empty (1 μg) | 74 | 108 |
| 5 μg RSV F + 0.01 μg vA17u/RV01(36) | 27 | 34 |
| 5 μg RSV F + 0.1 μg vA17u/RV01(36) | 61 | 70 |
| 5 μg RSV F + 1 μg vA17u/RV01(36) | 133 | 113 |
| 5 μg RSV F + 0.01 μg vA336u/RV01(36) | <20 | <20 |
| 5 μg RSV F + 0.1 μg vA336u/RV01(36) | 34 | 67 |
| 5 μg RSV F + 1 μg vA336u/RV01(36) | 373 | 258 |
| None | <20 | 23 |

TABLE I-11

Frequencies of RSV F-specific CD4+ splenic T cells on day 49 (4wp2). Shown are net (antigen-specific) cytokine-positive frequency (%) ±95% confidence half-interval. Net frequencies shown in bold indicate stimulated responses that were statistically significantly >0.

| | CD4+CD8− splenic T cells: % cytokine-positive and specific for RSV peptides F51-66, F164-178, F309-323 | | | |
|---|---|---|---|---|
| dose/vaccine | IFNg+ | IL2+ | IL5+ | TNFa+ |
| 1E6 IU VRP-VCR2.1-RSV-F-full | **0.10** ± 0.03 | **0.12** ± 0.05 | −0.01 ± 0.02 | **0.13** ± 0.05 |
| 5 μg RSV F | 0.00 ± 0.01 | **0.03** ± 0.02 | 0.01 ± 0.01 | 0.00 ± 0.02 |
| 5 μg RSV F/25 μg TLR7A/Alum | 0.00 ± 0.01 | **0.04** ± 0.02 | 0.00 ± 0.01 | 0.02 ± 0.02 |
| 5 μg RSV F + 1 μg vA317u/CNE17 | **0.03** ± 0.01 | **0.10** ± 0.03 | **0.01** ± 0.01 | **0.06** ± 0.03 |
| 5 μg RSV F + 1 μg vA317u/RV01(36) | **0.12** ± 0.03 | **0.31** ± 0.05 | 0.01 ± 0.01 | **0.31** ± 0.05 |
| 5 μg RSV F + RV01(36) empty (0.01 μg) | 0.00 ± 0.01 | **0.02** ± 0.01 | 0.00 ± 0.01 | **0.02** ± 0.02 |
| 5 μg RSV F + RV01(36) empty (0.1 μg) | 0.00 ± 0.01 | **0.04** ± 0.02 | **0.02** ± 0.01 | 0.01 ± 0.02 |
| 5 μg RSV F + RV01(36) empty (1 μg) | 0.00 ± 0.01 | **0.06** ± 0.02 | **0.07** ± 0.02 | 0.01 ± 0.02 |
| 5 μg RSV F + 0.01 μg vA17u/RV01(36) | **0.01** ± 0.01 | **0.06** ± 0.02 | **0.01** ± 0.01 | 0.01 ± 0.02 |
| 5 μg RSV F + 0.1 μg vA17u/RV01(36) | **0.02** ± 0.01 | **0.09** ± 0.02 | 0.01 ± 0.01 | **0.06** ± 0.02 |
| 5 μg RSV F + 1 μg vA17u/RV01(36) | **0.07** ± 0.02 | **0.21** ± 0.04 | **0.02** ± 0.02 | **0.18** ± 0.04 |
| 5 μg RSV F + 0.01 μg vA336u/RV01(36) | **0.01** ± 0.01 | **0.02** ± 0.01 | 0.00 ± 0.01 | 0.01 ± 0.02 |
| 5 μg RSV F + 0.1 μg vA336u/RV01(36) | **0.01** ± 0.01 | **0.06** ± 0.02 | 0.00 ± 0.01 | **0.04** ± 0.02 |
| 5 μg RSV F + 1 μg vA336u/RV01(36) | **0.10** ± 0.03 | **0.22** ± 0.04 | 0.00 ± 0.01 | **0.22** ± 0.04 |
| None | 0.00 ± 0.01 | 0.00 ± 0.01 | 0.00 ± 0.01 | −0.01 ± 0.02 |

TABLE I-12

Frequencies of RSV F-specific CD8+ splenic T cells on day 49 (4wp2). Shown are net (antigen-specific) cytokine-positive frequency (%) ±95% confidence half-interval. Net frequencies shown in bold indicate stimulated responses that were statistically significantly >0.

| | CD8+CD4− splenic T cells: % cytokine-positive and specific for RSV F peptides F85-93 and F249-258 | | | |
|---|---|---|---|---|
| dose/vaccine | IFNg+ | IL2+ | IL5+ | TNFa+ |
| 1E6 IU VRP-VCR2.1-RSV-F-full | **1.51** ± 0.16 | **0.59** ± 0.10 | 0.00 ± 0.02 | **1.11** ± 0.14 |
| 5 μg RSV F | −0.01 ± 0.06 | 0.03 ± 0.03 | 0.00 ± 0.01 | 0.00 ± 0.03 |
| 5 μg RSV F/25 μg TLR7A/Alum | **0.21** ± 0.07 | **0.16** ± 0.06 | 0.00 ± 0.02 | **0.22** ± 0.07 |
| 5 μg RSV F + 1 μg vA317u/CNE17 | **1.40** ± 0.15 | **0.74** ± 0.11 | 0.00 ± 0.03 | **1.03** ± 0.13 |
| 5 μg RSV F + 1 μg vA317u/RV01(36) | **5.60** ± 0.29 | **2.26** ± 0.18 | 0.00 ± 0.02 | **4.56** ± 0.26 |
| 5 μg RSV F + RV01(36) empty (0.01 μg) | **0.11** ± 0.06 | **0.07** ± 0.04 | −0.04 ± 0.03 | **0.07** ± 0.05 |
| 5 μg RSV F + RV01(36) empty (0.1 μg) | **0.19** ± 0.07 | **0.20** ± 0.06 | 0.00 ± 0.02 | **0.20** ± 0.06 |
| 5 μg RSV F + RV01(36) empty (1 μg) | **0.60** ± 0.10 | **0.66** ± 0.10 | 0.01 ± 0.02 | **0.66** ± 0.11 |
| 5 μg RSV F + 0.01 μg vA17u/RV01(36) | **0.10** ± 0.05 | **0.06** ± 0.04 | 0.02 ± 0.03 | **0.07** ± 0.04 |
| 5 μg RSV F + 0.1 μg vA17u/RV01(36) | **1.00** ± 0.13 | **0.51** ± 0.09 | −0.03 ± 0.02 | **0.72** ± 0.11 |
| 5 μg RSV F + 1 μg vA17u/RV01(36) | **2.18** ± 0.18 | **1.24** ± 0.14 | 0.00 ± 0.02 | **1.67** ± 0.16 |
| 5 μg RSV F + 0.01 μg vA336u/RV01(36) | **0.12** ± 0.06 | **0.12** ± 0.04 | 0.01 ± 0.02 | **0.13** ± 0.05 |
| 5 μg RSV F + 0.1 μg vA336u/RV01(36) | **1.01** ± 0.13 | **0.54** ± 0.10 | 0.01 ± 0.03 | **0.80** ± 0.12 |
| 5 μg RSV F + 1 μg vA336u/RV01(36) | **2.39** ± 0.19 | **1.16** ± 0.14 | 0.02 ± 0.03 | **1.93** ± 0.17 |
| None | 0.00 ± 0.03 | 0.00 ± 0.02 | −0.02 ± 0.03 | 0.02 ± 0.03 |

Example II

Co-Administration of RNA and Protein and Sequential Administration of RNA and Protein to Mice The vA142 replicon was used for this study. This construct expresses the full-length wild type surface fusion glycoprotein of RSV with the fusion peptide deleted and the 3' end of the replicon is formed by ribozyme-mediated cleavage. BALB/c mice, 116 total, were divided into 11 groups (4-22 animals per group).

Group 1 (8 animals) were given bilateral intramuscular vaccinations (50 μL per leg) on days 0, 21 with unadjuvanted RSV-F subunit protein vaccine (3 μg) and all animals were sacrificed at day 42.

Group 2 (22 animals) were given bilateral intramuscular vaccinations (50 μL per leg) on days 0, 21 with the RSV-F subunit protein vaccine (3 μg) adjuvanted with alum. 4 animals were sacrificed at day 42. 6 mice were given a third vaccination at day 42 with the RSV-F subunit protein vaccine (3 μg) adjuvanted with alum and the animals were sacrificed at day 63. 6 mice were given a third vaccination at day 42 with RNA (vA142, 1 μg) formulated with CNE17 (10:1 N:P ratio) and the animals were sacrificed at day 63. 6 mice were given a third vaccination at day 42 with RNA (vA142, 1 μg) formulated in LNP (RV01(39) (composition: DlinDMA 40%, DSPC-10%, Chol-48%, PEG DMG 5000-2% at an N:P ratio of 8:1, made using Method A, 175 μg RNA batch size) and the animals were sacrificed at day 63.

Group 3 (8 animals) were given bilateral intramuscular vaccinations (50 μL per leg) on days 0, 21 with the RSV-F subunit protein vaccine (3 μg) adjuvanted with alum and a small molecule TLR7 agonist (TLR7A), all animals were sacrificed at day 42.

Group 4 (8 animals) were given bilateral intramuscular vaccinations (50 μL per leg) on days 0, 21 with the RSV-F subunit protein vaccine (3 μg) adjuvanted with MF59 (equivalent squalene dose to CNE17) and all animals were sacrificed at day 42.

Group 5 (8 animals) were given bilateral intramuscular vaccinations (50 μL per leg) on days 0, 21 with the RSV-F subunit protein vaccine (3 μg) adjuvanted with CNE17 and animals were sacrificed at day 42.

Group 6 (16 animals) were given bilateral intramuscular vaccinations (50 μL per leg) on days 0, 21 with RNA (vA142, 1 μg) formulated with CNE17. 4 animals were sacrificed at day 42. 6 mice were given a third vaccination at day 42 with the RSV-F subunit protein vaccine (3 μg) adjuvanted with alum and the animals were sacrificed at day 63. 6 mice were given a third vaccination at day 42 with RNA (vA142, 1 μg) formulated with CNE17 and the animals were sacrificed at day 63.

Group 7 (16 animals) were given bilateral intramuscular vaccinations (50 μL per leg) on days 0, 21 with RNA (vA142, 1 μg) formulated with LNP (RV01(39)) (composition: DlinDMA 40%, DSPC-10%, Chol-48%, PEG DMG 5000-2% at an N:P ratio of 8:1, made using Method A, 175 μg RNA batch size). 4 animals were sacrificed at day 42. 6 mice were given a third vaccination at day 42 with the RSV-F subunit protein vaccine (3 μg) adjuvanted with alum and the animals were sacrificed at day 63. 6 mice were given a third vaccination at day 42 with RNA (vA142, 1 μg) formulated with LNP (RV01(39)) (composition: DlinDMA 40%, DSPC—10%, Chol—48%, PEG DMG 5000-2% at an N:P ratio of 8:1, made using Method A, 175 μg RNA batch size) and the animals were sacrificed at day 63.

Group 8 (8 animals) were given bilateral intramuscular vaccinations (50 μL per leg) on days 0, 21 with RNA (vA142, 1 μg) and the RSV-F protein subunit (no alum or MF59) formulated with CNE17. All animals were sacrificed at day 42.

Group 9 (8 animals) were given bilateral intramuscular vaccinations (50 μL per leg) on days 0, 21 with RNA (vA142, 1 μg) formulated in LNP (RV01(39)) (composition: DlinDMA 40%, DSPC— 10%, Chol-48%, PEG DMG 5000-2% at an N:P ratio of 8:1, made using Method A, 175 μg RNA batch size) and mixed with the RSV-F protein subunit (no alum or MF59). All animals were sacrificed at day 42.

Group 10 (10 animals) were given bilateral intramuscular vaccinations (50 μL per leg) on days 0, 21 with VRPs ($1\times10^6$ IU) expressing the full-length wild type surface fusion glycoprotein of RSV with the fusion peptide deleted. 4 animals were sacrificed at day 42. 6 mice were given a third vaccination at day 42 with the RSV-F subunit protein vaccine (3 μg) adjuvanted with alum and the animals were sacrificed at day 63.

Group 11 (4 Animals) Naïve control.

Serum was collected for antibody analysis on days 0, 20, 41 and 63. Spleens were harvested on days 42 and 63 for T-cell analysis.

Results

F-specific serum IgG titers are shown in table II-1 (day 20), II-2 (day 41) and II-7 (day 63). F-specific serum IgG1 titers are shown in tables II-3 (day 41) and II-8 (day 63), and F-specific serum IgG2a titers are shown in tables II-4 (day 41) and II-9 (day 63). RSV serum neutralizing antibody titers are shown in tables II-5 (day 41) and II-10 (day 63). Average net F-specific cytokine-positive T cell frequencies (CD4+ or CD8+) are shown in tables II-6 (day 42) and II-11 (day 63).

Conclusions

The data collected after the second vaccination of BALB/c mice show the following:

CNE17 is a potent adjuvant for the F subunit, as the F-specific IgG titers induced by vaccination with F subunit+CNE17 were greater than those induced by unadjuvanted F subunit, and equal to those induced by F subunit+alum or F subunit+MF59. In each of these four groups (F subunit+CNE17, unadjuvanted F subunit, F subunit+alum, F subunit+MF59) the F-specific IgG response was primarily IgG1 (very little/no IgG2a). Addition of a TLR7 agonist (TLR7A) to the F+alum vaccine increased the magnitude of the total F-specific IgG response by approximately two-fold, and induced class switching to IgG2a.

vA142+CNE17 and vA142+RV01 vaccines each induced F-specific IgG class switching to IgG2a (F-specific IgG2a titers were at least ten-fold greater than F-specific IgG1 titers when measured after the second vaccination), although the magnitude of the response to vA142+RV01 was approximately ten-fold greater response than the response to vA142+CNE17.

vA142+CNE17+F subunit (without alum or MF59) induced F-specific IgG titers that were 24-fold those induced by vA142+CNE17 (without F subunit), but were approximately equal to those induced by F subunit+CNE17 (without vA142). The F-specific IgG isotype induced by vA142+CNE17+F subunit was primarily IgG1, matching the response to F subunit+CNE17 (primarily IgG1) but not the response to vA142+CNE17 (primarily IgG2a).

vA142+RV01+F subunit (without alum or MF59) induced a F-specific IgG titer that was approximately equal in magnitude to that induced by vA142+CNE17 (without F subunit). The F-specific IgG isotype induced by the vA142+RV01+F subunit vaccine was primarily IgG2a, matching the response to vA142+CNE17.

The RSV neutralization titers at the two weeks post second vaccination time point correlated well with the total F-specific IgG titers.

Splenic T cell responses (CD4 and CD8) to all subunit vaccines that did not contain replicon were low. Replicon vaccines induced a robust CD8 response, and a moderate CD4 response. Both T cell subsets produced primarily type 1 cytokines including IFNγ, TNFα, and IL2. The magnitude of the CD8 T cell response to vA142+RV01 was approximately equal to the response induced by VRP, and about five-fold greater than the response induced by vA142+CNE17.

vA142+CNE17+F subunit induced a robust CD8 T cell response that was greater in magnitude than the sum of the responses induced by F subunit+CNE17 and vA142+CNE17 vaccines. vA142+RV01+F subunit induced a robust CD8 response that was equal in magnitude to that induced by vA142+RV01.

The data collected after the third vaccination of BALB/c mice show the following:

A third vA142+CNE17 vaccination boosted the F-specific IgG and RSV neutralization titers three fold. A third vA142+RV01 vaccination boosted the F-specific IgG titer two fold and the RSV neutralization titer four fold.

F-specific and RSV neutralization titers were greatly enhanced after F subunit+alum vaccination of mice previously vaccinated twice with vA142+CNE17 (increased IgG titers by 46 fold and RSV neutralization titers by 62 fold). F-specific and RSV neutralization titers were also enhanced after F subunit+alum vaccination of mice previously vaccinated twice with vA142+RV01 (increased IgG titers by 5 fold and RSV neutralization titers by 6 fold). The magnitude of the RSV neutralization titers after two replicon vaccinations followed by one F subunit+alum vaccination were equal to or greater than that induced by three subunit vaccinations.

After two vaccinations, the F-specific IgG isotype induced by F subunit+alum was primarily IgG1, whereas the isoytpe induced by vA142+CNE17 or vA142+RVOlwas primarily IgG2a. This isoptype balance set by the priming vaccinations was maintained after a third vaccination with a homologous or heterologous vaccine. For example, the dominant F-specific IgG isotype was IgG1 for mice vaccinated three times with F subunit+alum, vaccinated twice with F subunit+alum and then once with vA142+CNE17, or vaccinated twice with F subunit+alum and then once with vA142+RV01. The dominant F-specific IgG isotype was IgG2a for mice vaccinated three times with vA142+CNE17, mice vaccinated three times with vA142+RV01, mice vaccinated twice with vA142+CNE17 and then once with F subunit+alum, and mice vaccinated twice with vA142+RV01 and then once with F subunit+alum. IgG1 is often associated with a T helper type 1 (Th1) and IgG2a is often associated with a T helper type 2 (Th2) response. These data show that replicon vaccines induced a Th1-type response that was maintained even after a subunit+alum boost (that in itself induces a Th2-like response).

TABLE II-1

F-specific serum IgG titers of BALB/c mice, 2-22 animals per group, 20 days (~3wp1) after intramuscular vaccination with the indicated vaccines. Data are represented as titers for individual animals and the geometric mean titer (bottom row in table) of each group. If an individual animal had a titer of <25 (limit of detection) it was assigned a titer of 5.

~3wp1 (day 20) F-specific serum IgG titers

| Group | | | | | | | | | | |
|---|---|---|---|---|---|---|---|---|---|---|
| 3 µg F trimer subunit | 3 µg F trimer subunit + alum | 3 µg F trimer subunit + alum + 25 µg TLR7A | 3 µg F trimer subunit + ⅓ dose MF59 | 3 µg F trimer subunit + CNE17 | 1 µg vA142 + CNE17 | 1 µg vA142 + RV01 (39) | 3 µg F trimer subunit + 1 µg vA142 + CNE17 | 3 µg F trimer subunit + 1 µg vA142 + RV01 (39) | 1E6 IU VRP (A142) | naive |
| 5 | 2792 | 10085 | 2169 | 2753 | 1019 | 5078 | 2561 | 3622 | 5591 | 5 |
| 128 | 3337 | 14233 | 2046 | 1911 | 388 | 3995 | 1309 | 6320 | 3304 | 5 |
| 82 | 4533 | 19072 | 2817 | 3158 | 1167 | 11053 | 1639 | 5060 | 4378 | |
| 1414 | 3182 | 6711 | 5209 | 1913 | 1977 | 6199 | 2778 | 6295 | 6363 | |
| 46 | 4991 | 21158 | 1509 | 2247 | 731 | 6295 | 2058 | 5158 | 2349 | |
| 370 | 2902 | 12073 | 1445 | 2404 | 897 | 4503 | 4365 | 5027 | 5251 | |
| 114 | 3480 | 10915 | 1936 | 1615 | 500 | 8196 | 5393 | 6767 | 5419 | |
| 384 | 3370 | 19626 | 28213 | 2130 | 885 | 5225 | 5894 | 7459 | 2965 | |
| | 4444 | | | | 653 | 7301 | | | 3856 | |
| | 2567 | | | | 854 | 4438 | | | 4493 | |
| | 3005 | | | | 1335 | 5142 | | | 4352 | |
| | 9515 | | | | 1197 | 3949 | | | | |
| | 2875 | | | | 967 | 5833 | | | | |
| | 2775 | | | | 1908 | 8050 | | | | |
| | 3918 | | | | 1676 | 2179 | | | | |
| | 1654 | | | | 388 | 3298 | | | | |
| | 5078 | | | | | | | | | |
| | 5410 | | | | | | | | | |
| | 5950 | | | | | | | | | |
| | 5159 | | | | | | | | | |
| | 7033 | | | | | | | | | |
| | 3552 | | | | | | | | | |
| 124 | 3862 | 13344 | 3063 | 2220 | 924 | 5289 | 2850 | 5591 | 4227 | 5 |

TABLE II-2

F-specific serum IgG titers of BALB/c mice, 2-22 animals per group, after intramuscular vaccination with the indicated vaccines on days 0 and 21. Serum was collected for antibody analysis on day 41 (~3wp2). Data are represented as titers for individual animals and the geometric mean titer (bottom row of table) for each group. If an individual animal had a titer of <25 (limit of detection) it was assigned a titer of 5.

~3wp2 (day 41) F-specific serum IgG titers

| Group | | | | | | | | | | |
|---|---|---|---|---|---|---|---|---|---|---|
| 3 µg F trimer subunit | 3 µg F trimer subunit + alum | 3 µg F trimer subunit + alum + 25 µg TLR7A | 3 µg F trimer subunit + ⅓ dose MF59 | 3 µg F trimer subunit + CNE17 | 1 µg vA142 + CNE17 | 1 µg vA142 + RV01 (39) | 3 µg F trimer subunit + 1 µg vA142 + CNE17 | 3 µg F trimer subunit + 1 µg vA142 + RV01 (39) | 1E6 IU VRP (A142) | naive |
| 3333 | 127489 | 371967 | 143371 | 220170 | 6311 | 41898 | 191234 | 48414 | 45898 | 5 |
| 64917 | 126823 | 279675 | 113913 | 119981 | 13605 | 72032 | 155411 | 107539 | 55587 | 5 |
| 18031 | 272342 | 442396 | 125447 | 111939 | 3550 | 114060 | 140117 | 89808 | 80201 | |
| 44805 | 163175 | 372514 | 226022 | 176715 | 9278 | 98383 | 195165 | 93729 | 24167 | |
| 27313 | 205032 | 419241 | 166683 | 79338 | 7292 | 63614 | 181607 | 81754 | 26529 | |
| 67566 | 153234 | 304957 | 140631 | 108340 | 13343 | 78069 | 193053 | 62075 | 24529 | |
| 11077 | 89144 | 412571 | 213628 | 172781 | 2963 | 64790 | 250282 | 82313 | 32024 | |
| 66825 | 208898 | 212292 | 363933 | 232211 | 15017 | 65534 | 212180 | 126066 | 35789 | |
| | 163304 | | | | 12236 | 72860 | | | 17290 | |
| | 328763 | | | | 18115 | 93245 | | | 31304 | |
| | 186277 | | | | 16334 | 78355 | | | | |
| | 254714 | | | | 5446 | 35923 | | | | |
| | 199791 | | | | 1288 | 129992 | | | | |
| | 70668 | | | | 13656 | 133508 | | | | |
| | 194242 | | | | 11395 | 30533 | | | | |
| | 187070 | | | | 18314 | 67121 | | | | |
| | 268138 | | | | 1962 | | | | | |
| | 137072 | | | | | | | | | |
| | 205685 | | | | | | | | | |
| | 85988 | | | | | | | | | |
| | 333357 | | | | | | | | | |
| | 352752 | | | | | | | | | |
| 26439 | 180136 | 343088 | 174095 | 143540 | 7879 | 71680 | 187277 | 83253 | 33886 | 5 |

TABLE II-3

F-specific serum IgG1 titers of BALB/c mice, 2-22 animals per group, after intramuscular vaccination with the indicated vaccines on days 0 and 21. Serum was collected for antibody analysis on day 41 (~3wp2). Data are represented as titers for individual animals and the geometric mean titer (bottom row of table) for each group. If an individual animal had a titer of <25 (limit of detection) it was assigned a titer of 5.

~3wp2 (day 41) F-specific serum IgG1 titers

Group

| 3 µg F trimer subunit | 3 µg F trimer subunit + alum | 3 µg F trimer subunit + alum + 25 µg TLR7A | 3 µg F trimer subunit + 1/3 dose MF59 | 3 µg F trimer subunit + CNE17 | 1 µg vA142 + CNE17 | 1 µg vA142 + RV01 (39) | 3 µg F trimer subunit + 1 µg vA142 + CNE17 | 3 µg F trimer subunit + 1 µg vA142 + RV01 (39) | 1E6 IU VRP (A142) | naive |
|---|---|---|---|---|---|---|---|---|---|---|
| 4751 | 225245 | 350032 | 266739 | 903304 | 1650 | 14319 | 451989 | 17066 | 13904 | 5 |
| 107732 | 238261 | 271960 | 178609 | 197261 | 4957 | 9623 | 418360 | 22116 | 9898 | 5 |
| 28126 | 650444 | 367427 | 219141 | 207527 | 1238 | 30034 | 279866 | 65528 | 5531 | |
| 59285 | 350077 | 315508 | 581887 | 241267 | 936 | 14032 | 449010 | 21682 | 5097 | |
| 36991 | 522278 | 360452 | 343140 | 229090 | 5016 | 8154 | 347235 | 32735 | 10355 | |
| 86261 | 285165 | 288697 | 224815 | 191527 | 519 | 6857 | 408570 | 17214 | 3932 | |
| 15630 | 132721 | 648766 | 531617 | 321951 | 7008 | 23195 | 446552 | 19802 | 4090 | |
| 86314 | 366415 | 106856 | 506364 | 457173 | 3454 | 8078 | 561199 | 39707 | 5493 | |
| | 294116 | | | | 4947 | 27901 | | | 972 | |
| | 940674 | | | | 3960 | 25553 | | | 2990 | |
| | 333129 | | | | 2330 | 17643 | | | | |
| | 302960 | | | | 552 | 6776 | | | | |
| | 352372 | | | | 504 | 57247 | | | | |
| | 94693 | | | | 1864 | 10066 | | | | |
| | 304688 | | | | 5340 | 7894 | | | | |
| | 293133 | | | | 5 | 10994 | | | | |
| | 298757 | | | | | | | | | |
| | 180582 | | | | | | | | | |
| | 317663 | | | | | | | | | |
| | 109094 | | | | | | | | | |
| | 388756 | | | | | | | | | |
| | 609926 | | | | | | | | | |
| 37208 | 300542 | 307342 | 325547 | 295168 | 1449 | 14154 | 412900 | 26423 | 5027 | 5 |

TABLE II-4

F-specific serum IgG2a titers of BALB/c mice, 2-22 animals per group, after intramuscular vaccination with the indicated vaccines on days 0 and 21. Serum was collected for antibody analysis on day 41 (~3wp2). Data are represented as titers for individual animals and the geometric mean titer (bottom row of table) for each group. If an individual animal had a titer of <125 (limit of detection) it was assigned a titer of 25.

~3wp2 (day 41) F-specific serum IgG2a titers

Group

| 3 µg F trimer subunit | 3 µg F trimer subunit + alum | 3 µg F trimer subunit + alum + 25 µg TLR7A | 3 µg F trimer subunit + ⅓ dose MF59 | 3 µg F trimer subunit + CNE17 | 1 µg vA142 + CNE17 | 1 µg vA142 + RV01 (39) | 3 µg F trimer subunit + 1 µg vA142 + CNE17 | 3 µg F trimer subunit + 1 µg vA142 + RV01 (39) | 1E6 IU VRP (A142) | naive |
|---|---|---|---|---|---|---|---|---|---|---|
| 25 | 25 | 96017 | 248 | 25 | 20432 | 87093 | 36243 | 109284 | 119958 | 25 |
| 25 | 25 | 18204 | 5412 | 25 | 20469 | 194006 | 2525 | 298231 | 153137 | 25 |
| 25 | 25 | 131509 | 1467 | 25 | 5716 | 414280 | 1440 | 113622 | 174041 | |
| 1484 | 25 | 69704 | 25 | 25 | 42031 | 340224 | 529 | 179564 | 64698 | |
| 479 | 25 | 138075 | 25 | 1660 | 26914 | 172298 | 17489 | 148624 | 64977 | |
| 2326 | 25 | 79634 | 25 | 25 | 11979 | 240916 | 25 | 135295 | 64744 | |
| 662 | 2631 | 71358 | 25 | 37663 | 27314 | 218653 | 25 | 179619 | 140264 | |
| 8085 | 25 | 195149 | 319060 | 25 | 28250 | 256190 | 5480 | 268365 | 101520 | |
| | 25 | | | | 35361 | 163792 | | | 61478 | |
| | 25 | | | | 33064 | 248366 | | | 89519 | |
| | 25 | | | | 16448 | 179106 | | | | |
| | 25 | | | | 4934 | 127192 | | | | |
| | 25 | | | | 49826 | 356910 | | | | |
| | 318 | | | | 27778 | 598570 | | | | |
| | 410 | | | | 34555 | 59459 | | | | |
| | 25 | | | | 6434 | 150814 | | | | |
| | 25 | | | | | | | | | |
| | 25 | | | | | | | | | |
| | 25 | | | | | | | | | |
| | 25 | | | | | | | | | |

TABLE II-4-continued

F-specific serum IgG2a titers of BALB/c mice, 2-22 animals per group, after intramuscular vaccination with the indicated vaccines on days 0 and 21. Serum was collected for antibody analysis on day 41 (~3wp2). Data are represented as titers for individual animals and the geometric mean titer (bottom row of table) for each group. If an individual animal had a titer of <125 (limit of detection) it was assigned a titer of 25.

~3wp2 (day 41) F-specific serum IgG2a titers

| Group | | | | | | | | | | |
|---|---|---|---|---|---|---|---|---|---|---|
| 3 μg F trimer subunit | 3 μg F trimer subunit + alum | 3 μg F trimer subunit + alum + 25 μg TLR7A | 3 μg F trimer subunit + ⅓ dose MF59 | 3 μg F trimer subunit + CNE17 | 1 μg vA142 + CNE17 | 1 μg vA142 + RV01 (39) | 3 μg F trimer subunit + 1 μg vA142 + CNE17 | 3 μg F trimer subunit + 1 μg vA142 + RV01 (39) | 1E6 IU VRP (A142) | naive |
| | 25 | | | | | | | | | |
| | 1268 | | | | | | | | | |
| 329 | 47 | 83891 | 354 | 105 | 20135 | 205134 | 1195 | 168328 | 96244 | 25 |

TABLE II-5

RSV serum neutralization titers of BALB/c mice after intramuscular vaccinations with the indicated vaccines on days 0 and 21. Serum was collected for analysis on day 41 (~3wp2). Data are represented as 60% RSV neutralization titers for pools of 3-4 animals per group and geometric mean titers of 1-7 pools per group. If an individual pool had a titer of <20 (limit of detection) it was assigned a titer of 10.

| | RSV serum neutralization titers ~3wp2 (day 41) | | | | | | | |
|---|---|---|---|---|---|---|---|---|
| Group | pool 1 | pool 2 | pool 3 | pool 4 | pool 5 | pool 6 | pool 7 | GMT |
| 3 ug F trimer subunit | 10 | | | | | | | 10 |
| 3 ug F trimer subunit + alum | 159 | 221 | 655 | 562 | 396 | 198 | 303 | 315 |
| 3 ug F trimer subunit + alum + 25 ug TLR7A | 595 | 214 | | | | | | 357 |
| 3 ug F trimer subunit + 1/3 dose MF59 | 509 | 71 | | | | | | 190 |
| 3 ug F trimer subunit + CNE17 | 106 | 149 | | | | | | 126 |
| 1 ug vA142 + CNE17 | 29 | 38 | 34 | 31 | 41 | | | 34 |
| 1 ug vA142 + RV01 (39) | 344 | 1995 | 311 | 148 | 331 | | | 402 |
| 3 ug F trimer subunit + 1 ug vA142 + CNE17 | 73 | 352 | | | | | | 160 |
| 3 ug F trimer subunit + 1 ug vA142 + RV01 (39) | 116 | 262 | | | | | | 174 |
| 1E6 IU VRP (A142) | 82 | 61 | 40 | | | | | 58 |

TABLE II-6

Frequencies of RSV F-specific CD4+ or CD8+ splenic T cells of BALB/c mice, 4 animals per group (except 2 in naive group), after intramuscular vaccination with the indicated vaccines on days 0 and 21. Spleens were collected for T cell analysis on day 42 (~3wp2). Shown are average net F-specific cytokine-positive frequencies (%) of duplicate wells of one pool of 4 spleens per group.

| | ~3wp2 (day 41) splenic F-specific T cell response | | | | | | | |
|---|---|---|---|---|---|---|---|---|
| | CD4+CD8− | | | | CD4−CD8+ | | | |
| Group | IFNg+ | TNFa+ | IL-2+ | IL-5+ | IFNg+ | TNFa+ | IL-2+ | IL-5+ |
| 3 μg F trimer subunit | 0.00 | 0.01 | 0.00 | 0.01 | 0.01 | 0.01 | 0.01 | 0.00 |
| 3 μg F trimer subunit + alum | 0.00 | 0.00 | 0.02 | 0.00 | 0.01 | 0.00 | 0.04 | 0.00 |
| 3 μg F trimer subunit + alum + 25 μg TLR7A | 0.01 | 0.02 | 0.03 | 0.01 | 0.02 | 0.04 | 0.03 | 0.01 |
| 3 μg F trimer subunit + ⅓ dose MF59 | 0.02 | 0.02 | 0.05 | 0.02 | 0.09 | 0.10 | 0.24 | 0.00 |
| 3 μg F trimer subunit + CNE17 | 0.01 | 0.02 | 0.04 | 0.05 | 0.02 | 0.10 | 0.14 | 0.00 |
| 1 μg vA142 + CNE17 | 0.05 | 0.08 | 0.16 | 0.01 | 0.57 | 0.59 | 0.37 | 0.00 |
| 1 μg vA142 + RV01 (39) | 0.09 | 0.18 | 0.34 | 0.00 | 3.45 | 3.59 | 1.41 | 0.01 |
| 3 μg F trimer subunit + 1 μg vA142 + CNE17 | 0.04 | 0.08 | 0.19 | 0.09 | 2.42 | 2.55 | 0.99 | 0.01 |
| 3 μg F trimer subunit + 1 μg vA142 + RV01 (39) | 0.13 | 0.26 | 0.50 | 0.00 | 3.35 | 3.32 | 1.92 | 0.01 |

TABLE II-6-continued

Frequencies of RSV F-specific CD4+ or CD8+ splenic T cells of BALB/c mice, 4 animals per group (except 2 in naive group), after intramuscular vaccination with the indicated vaccines on days 0 and 21. Spleens were collected for T cell analysis on day 42 (~3wp2). Shown are average net F-specific cytokine-positive frequencies (%) of duplicate wells of one pool of 4 spleens per group.

| | ~3wp2 (day 41) splenic F-specific T cell response | | | | | | | |
|---|---|---|---|---|---|---|---|---|
| | CD4+CD8− | | | | CD4−CD8+ | | | |
| Group | IFNg+ | TNFa+ | IL-2+ | IL-5+ | IFNg+ | TNFa+ | IL-2+ | IL-5+ |
| 1E6 IU VRP (A142) | 0.10 | 0.18 | 0.30 | 0.01 | 2.68 | 2.93 | 1.55 | 0.00 |
| Naïve | 0.00 | 0.01 | 0.01 | 0.00 | 0.00 | 0.00 | 0.00 | 0.00 |

TABLE II-7

F-specific serum IgG titers of BALB/c mice, 2-6 animals per group, after intramuscular vaccinations with the indicated 1st, 2nd, and 3rd vaccines (administered on days 0, 21, and 42, respectively). Serum was collected for antibody analysis on day 63 (3wp3). Data are represented as titers for individual animals and the geometric mean titer for each group. If an individual animal had a titer of <25 (limit of detection) it was assigned a titer of 5.

| Group | | | | | | | | |
|---|---|---|---|---|---|---|---|---|
| 1st and 2nd vaccination | 3rd vaccination | 3wp3 (day 63) F-specific serum IgG titers | | | | | | GMT |
| 3 ug F trimer subunit + alum | 3 ug F trimer subunit + alum | 397125 | 219348 | 234682 | 474062 | 325653 | 485166 | 339498 |
| 3 ug F trimer subunit + alum | 1 ug vA142 + CNE17 | 295650 | 285307 | 301188 | 108903 | 191240 | 263752 | 227749 |
| 3 ug F trimer subunit + alum | 1 ug vA142 + RV01 (39) | 389432 | 220866 | 340951 | 263722 | 316715 | 579546 | 335242 |
| 1 ug vA142 + CNE17 | 3 ug F trimer subunit + alum | 378695 | 368173 | 638358 | 580096 | 535790 | 747680 | 523925 |
| 1 ug vA142 + CNE17 | 1 ug vA142 + CNE17 | 28392 | 25370 | 20404 | 25687 | 28161 | 5515 | 19710 |
| 1 ug vA142 + RV01 | 3 ug F trimer subunit + alum | 422179 | 446249 | 284067 | 287956 | 441567 | 506771 | 388691 |
| 1 ug vA142 + RV01 (39) | 1 ug vA142 + RV01 (39) | 124230 | 68942 | 135140 | 161575 | 81778 | 99206 | 107195 |
| 1E6 IU VRP (A142) | 3 ug F trimer subunit + alum | 560903 | 458740 | 254037 | 268794 | 491496 | 200132 | 346419 |
| naive | Naïve | 5 | 5 | | | | | 5 |

TABLE II-8

F-specific serum IgG1 titers of BALB/c mice, 2-6 animals per group, after intramuscular vaccinations with the indicated 1st, 2nd, and 3rd vaccines (administered on days 0, 21, and 42, respectively). Serum was collected for antibody analysis on day 63 (3wp3). Data are represented as titers for individual animals and the geometric mean titer for each group. If an individual animal had a titer of <125 (limit of detection) it was assigned a titer of 25.

| Group | | | | | | | | |
|---|---|---|---|---|---|---|---|---|
| 1st and 2nd vaccination | 3rd vaccination | 3wp3 (day 63) F-specific serum IgG1 titers | | | | | | GMT |
| 3 ug F trimer subunit + alum | 3 ug F trimer subunit + alum | 472727 | 245635 | 204730 | 475968 | 378693 | 569982 | 366974 |
| 3 ug F trimer subunit + alum | 1 ug vA142 + CNE17 | 332385 | 331830 | 322523 | 118291 | 189876 | 261341 | 243571 |
| 3 ug F trimer subunit + alum | 1 ug vA142 + RV01 (39) | 466588 | 291761 | 417428 | 288690 | 350836 | 598125 | 388578 |
| 1 ug vA142 + CNE17 | 3 ug F trimer subunit + alum | 110372 | 97254 | 502079 | 172198 | 242153 | 79623 | 161727 |
| 1 ug vA142 + CNE17 | 1 ug vA142 + CNE17 | 8395 | 1386 | 488 | 8881 | 12117 | 25 | 1575 |
| 1 ug vA142 + RV01 | 3 ug F trimer subunit + alum | 54308 | 155078 | 153748 | 32589 | 193390 | 105775 | 97578 |
| 1 ug vA142 + RV01 (39) | 1 ug vA142 + RV01 (39) | 25565 | 7668 | 51279 | 8030 | 18916 | 25651 | 18428 |
| 1E6 IU VRP (A142) | 3 ug F trimer subunit + alum | 304345 | 235517 | 20501 | 53684 | 105506 | 18831 | 73427 |
| naive | Naïve | 25 | 25 | | | | | 25 |

TABLE II-9

F-specific serum IgG2a titers of BALB/c mice, 2-6 animals per group, after intramuscular vaccinations with the indicated $1^{st}$, $2^{nd}$, and $3^{rd}$ vaccines (administered on days 0, 21, and 42, respectively). Serum was collected for antibody analysis on day 63 (3wp3). Data are represented as titers for individual animals and the geometric mean titer for each group. If an individual animal had a titer of <125 (limit of detection) it was assigned a titer of 25.

| Group | | | | | | | | |
|---|---|---|---|---|---|---|---|---|
| $1^{st}$ and $2^{nd}$ vaccination | $3^{rd}$ vaccination | 3wp3 (day 63) F-specific serum IgG2a titers | | | | | | GMT |
| 3 ug F trimer subunit + alum | 3 ug F trimer subunit alum | 25 | 25 | 5124 | 25 | 683 | 495 | 173 |
| 3 ug F trimer subunit + alum | 1 ug vA142 + CNE17 | 25 | 678 | 25 | 1789 | 2090 | 52 | 209 |
| 3 ug F trimer subunit + alum | 1 ug vA142 + RV01 (39) | 7279 | 4583 | 8964 | 10947 | 3749 | 10965 | 7158 |
| 1 ug vA142 + CNE17 | 3 ug F trimer subunit + alum | 544099 | 598814 | 601179 | 241979 | 529568 | 1529305 | 580802 |
| 1 ug vA142 + CNE17 | 1 ug vA142 + CNE17 | 29369 | 27933 | 38983 | 19630 | 27763 | 14863 | 25248 |
| 1 ug vA142 + RV01 (39) | 3 ug F trimer subunit + alum | 886323 | 471796 | 277106 | 837672 | 628141 | 852851 | 610941 |
| 1 ug vA142 + RV01 (39) | 1 ug vA142 + RV01 (39) | 210624 | 150131 | 198056 | 340986 | 122466 | 140132 | 182253 |
| 1E6 IU VRP (A142) | 3 ug F trimer subunit + alum | 621104 | 472535 | 674444 | 548436 | 824451 | 581684 | 611064 |
| naive | Naïve | 25 | 25 | | | | | 25 |

TABLE II-10

RSV serum neutralization titers of BALB/c mice after intramuscular vaccinations with the indicated $1^{st}$, $2^{nd}$, and $3^{rd}$ vaccines (administered on days 0, 21, and 42, respectively). Serum was collected for analysis on day 63 (3wp3). Data are represented as 60% RSV neutralization titers for 2 pools of 3 animals per group and geometric mean titers of these 2 pools per group. If an individual pool had a titer of <20 (limit of detection) it was assigned a titer of 10.

| Group | | RSV serum neutralization titers | | |
|---|---|---|---|---|
| $1^{st}$ and $2^{nd}$ | | 3wp3 (day 63) | | |
| vaccination | $3^{rd}$ vaccination | pool 1 | pool 2 | GMT |
| 3 ug F trimer subunit + alum | 3 ug F trimer subunit + alum | 539 | 2982 | 1268 |
| 3 ug F trimer subunit + alum | 1 ug vA142 + CNE17 | 1199 | 1507 | 1344 |
| 3 ug F trimer subunit + alum | 1 ug vA142 + RV01 (39) | 1943 | 4024 | 2796 |
| 1 ug vA142 + CNE17 | 3 ug F trimer subunit + alum | 2283 | 2169 | 2225 |

TABLE II-10-continued

RSV serum neutralization titers of BALB/c mice after intramuscular vaccinations with the indicated $1^{st}$, $2^{nd}$, and $3^{rd}$ vaccines (administered on days 0, 21, and 42, respectively). Serum was collected for analysis on day 63 (3wp3). Data are represented as 60% RSV neutralization titers for 2 pools of 3 animals per group and geometric mean titers of these 2 pools per group. If an individual pool had a titer of <20 (limit of detection) it was assigned a titer of 10.

| Group | | RSV serum neutralization titers | | |
|---|---|---|---|---|
| $1^{st}$ and $2^{nd}$ | | 3wp3 (day 63) | | |
| vaccination | $3^{rd}$ vaccination | pool 1 | pool 2 | GMT |
| 1 ug vA142 + CNE17 | 1 ug vA142 + CNE17 | 144 | 96 | 118 |
| 1 ug vA142 + RV01 (39) | 3 ug F trimer subunit + alum | 4654 | 4882 | 4767 |
| 1 ug vA142 + RV01 (39) | 1 ug vA142 + RV01 (39) | 530 | 1240 | 868 |
| 1E6 IU VRP (A142) | 3 ug F trimer subunit + alum | 4672 | 2287 | 3269 |
| naive | Naïve | 10 | | 10 |

TABLE II-11

Frequencies of RSV F-specific CD4+ or CD8+ splenic T cells of BALB/c mice, 6 animals per group (except 2 in naive group), after intramuscular vaccinations with the indicated $1^{st}$, $2^{nd}$, and $3^{rd}$ vaccines (administered on days 0, 21, and 42, respectively). Spleens were collected for T cell analysis on day 63 (3wp3). Shown are average net F-specific cytokine-positive frequencies (%) of duplicate wells of one pool of 6 spleens per group.

| Group | | 3wp2 (day 63) splenic F-specific T cell response | | | | | | | |
|---|---|---|---|---|---|---|---|---|---|
| $1^{st}$ and $2^{nd}$ | | CD4+CD8− | | | | CD4−CD8+ | | | |
| vaccination | $3^{rd}$ vaccination | IFNg+ | TNFa+ | IL-2+ | IL-5+ | IFNg+ | TNFa+ | IL-2+ | IL-5+ |
| 3 ug F trimer subunit + alum | 3 ug F trimer subunit + alum | 0.00 | 0.01 | 0.02 | 0.02 | 0.01 | 0.01 | 0.03 | 0.00 |
| 3 ug F trimer subunit + alum | 1 ug vA142 + CNE17 | 0.00 | 0.03 | 0.07 | 0.02 | 0.14 | 0.23 | 0.26 | 0.01 |
| 3 ug F trimer subunit + alum | 1 ug vA142 + RV01 (39) | 0.00 | 0.04 | 0.07 | 0.01 | 0.09 | 0.19 | 0.18 | 0.00 |
| 1 ug vA142 + CNE17 | 3 ug F trimer subunit + alum | 0.07 | 0.29 | 0.34 | 0.01 | 0.37 | 0.49 | 0.25 | 0.01 |

TABLE II-11-continued

Frequencies of RSV F-specific CD4+ or CD8+ splenic T cells of BALB/c mice, 6 animals per group (except 2 in naive group), after intramuscular vaccinations with the indicated 1st, 2nd, and 3rd vaccines (administered on days 0, 21, and 42, respectively). Spleens were collected for T cell analysis on day 63 (3wp3). Shown are average net F-specific cytokine-positive frequencies (%) of duplicate wells of one pool of 6 spleens per group.

| Group | | 3wp2 (day 63) splenic F-specific T cell response | | | | | | | |
|---|---|---|---|---|---|---|---|---|---|
| 1st and 2nd | | CD4+CD8− | | | | CD4−CD8+ | | | |
| vaccination | 3rd vaccination | IFNg+ | TNFa+ | IL-2+ | IL-5+ | IFNg+ | TNFa+ | IL-2+ | IL-5+ |
| 1 ug vA142 + CNE17 | 1 ug vA142 + CNE17 | 0.02 | 0.16 | 0.19 | 0.00 | 0.29 | 0.35 | 0.28 | 0.01 |
| 1 ug vA142 + RV01 (39) | 3 ug F trimer subunit + alum | 0.03 | 0.18 | 0.19 | 0.01 | 0.97 | 1.47 | 0.51 | 0.00 |
| 1 ug vA142 + RV01 (39) | 1 ug vA142 + RV01 (39) | 0.05 | 0.37 | 0.35 | 0.00 | 0.99 | 1.47 | 0.58 | 0.00 |
| 1E6 IU VRP (A142) | 3 ug F trimer subunit + alum | 0.05 | 0.19 | 0.18 | 0.00 | 1.33 | 1.75 | 0.56 | 0.02 |
| naive | Naïve | 0.00 | 0.00 | 0.00 | 0.01 | 0.01 | 0.01 | 0.02 | 0.02 |

Example III

Sequential Administration of RNA and Protein to Rats (Study 1)

Three different replicons were used for this study: the vA317 replicon, which expresses the full-length wild type surface fusion glycoprotein of RSV (RSV-F); the vA318 replicon, which expresses the truncated (transmembrane and cytoplasmic tail removed) surface fusion glycoprotein of RSV; and the vA142 replicon, which expresses the full-length wild type surface fusion glycoprotein of RSV with the fusion peptide deleted. Cotton rats, 2-8 animals per group, were given intramuscular vaccinations (100 μL in one leg) on days 0 and 21 with the three different RNAs (vA317, vA318, vA142) formulated in LNPs (RV01(29) or CNE17 (N:P ratio 10:1) and given at two doses (1.0 and 0.1 μg, 8 animals/group). LNPs had the following composition: 40% DlinDMA, 10% DSPC, 48% Chol, 2% PEG DMG 2000, N:P ratio of 8:1 and was made using Method B, except a 150 μg RNA batch size was used. Control groups received the RSV-F subunit protein vaccine (5 μg) adjuvanted with alum (8 animals/group) and VRP's expressing full-length RSV-F ($1\times10^6$ IU, 8 animals/group). All the LNP, subunit and VRP groups received a third vaccination (day 56) with RSV-F subunit protein vaccine (5 μg) adjuvanted with alum. In addition there was a naïve control (4 animals/group). Serum was collected for antibody analysis on days 0, 21, 35, 56, 70. In addition, two groups were given bilateral intramuscular vaccinations (50 μL per leg) on days 0 and 56 with RNA (vA317, 1 μg) formulated in LNPs (RV01(29) or CNE17 (8 animals/group). These groups did not receive a third vaccination with the subunit protein vaccine. Serum was collected for antibody analysis on days 0, 14, 21, 28, 35, 42, 56, 70.

Results

F-specific serum IgG titers are shown in table III-1 (day 21), III-2 (day 35), III-3 (day 56), III-4 (day 70) for the groups that received the third vaccination with the RSV-F subunit vaccine. RSV serum neutralizing antibody titers on days 21, 35, 56 and 70 are shown in table III-5. F-specific serum IgG titers on days 14, 21, 28, 35, 42, 56, 70 are shown in table III-6 for the two groups that did not receive the third vaccination with the RSV-F subunit vaccine. RSV serum neutralizing antibody titers on days 14, 21, 28, 35, 42, 56, 70 for these two groups are shown in table III-7.

Conclusions

When formulated with RV01 or CNE17, all three replicons evaluated in this study (vA317, vA318, vA142) were immunogenic in cotton rats. Each elicited serum F-specific IgG and RSV neutralizing antibodies after the first vaccination, and a second vaccination effectively boosted the response. F-specific IgG titers after the second vaccination with 1.0 μg replicon were 1.5 to 4-fold higher than after the second vaccination with 0.1 μg replicon, regardless of the formulation. The three replicons evaluted in this study (vA317, vA318, vA142) elicited comparable antibody titers suggesting that full length RSV-F (with and without the fusion peptide) and truncated RSV-F are equally immunogenic in cotton rats. There was also little difference in antibody titer when the same replicon was formulated with RV01 or CNE17, suggesting that these two formulations are equally potent in cotton rats. RSV serum neutralization titers after a second replicon vaccination were at least ten-fold lower than after a second RSV-F subunit+alum or VRP vaccination.

Cotton rats vaccinated with replicon, VRP, or subunit on days 0 and 21 were all vaccinated with 5 μg RSV-F trimer subunit+alum on day 56 (five weeks after the second vaccination). This third vaccination did not boost antibody titers in cotton rats previously vaccinated with F trimer subunit+alum, but it provided a large boost to titers in cotton rats previously vaccinated with replicon (both RV01 and CNE17 formulations). In most cases the RSV serum neutralization titers after two replicon vaccinations followed by an F subunit+alum boost were equal to or greater than titers induced by two or three sequential F subunit+alum vaccinations.

For each group and time point a ratio of F-specific IgG titer to RSV neutralizing titer can be calculated, and is one indication of the quality of the antibody response. A lower ratio suggests that a larger fraction of the vaccine-induced antibody is capable of neutralizing RSV, and is therefore functional. The data from this study show that the F-specific IgG:RSV neutralizing antibody titer ratio was lower after vaccination with replicon or VRP than after vaccination with F subunit+alum. The lower F-specific IgG:RSV neutralizing antibody titer ratio set by two replicon or VRP vaccinations was maintained after a F subunit+alum boost.

This study also evaluated the kinetics of the antibody response to 1.0 μg vA317 formulated with RV01 or CNE17. F-specific serum IgG and RSV neutralization titers induced by a single vaccination reached their peak around day 21 and were maintained through at least day 56 (50-70% drop in F-specific IgG titer, little change in RSV neutralization titer). A homologous second vaccination was given to these animals on day 56, and boosted antibody titers to a level at least equal to that achieved when the second vaccination was administered on day 21.

TABLE III-1

F-specific serum IgG titers of cotton rats, 2-8 animals per group, 21 days after intramuscular vaccination with the indicated vaccines. Data are represented as titers for individual animals and the geometric mean titer for each group. If an individual animal had a titer of <25 (limit of detection) it was assigned a titer of 5.

| Group | 3wp1 (day 21) F-specific serum IgG titers | | | | | | | | GMT |
|---|---|---|---|---|---|---|---|---|---|
| 1 ug vA318/RV01 (29) | 503 | 750 | 144 | 141 | 104 | 509 | 103 | 501 | 260 |
| 0.1 ug vA318/RV01 (29) | 47 | 109 | 141 | 40 | 120 | 180 | 161 | 68 | 95 |
| 1 ug vA318/CNE17 | 446 | 1084 | 466 | 174 | 258 | 537 | 233 | 656 | 412 |
| 0.1 ug vA318/CNE17 | 696 | 906 | 327 | 242 | 418 | 173 | 438 | 63 | 316 |
| 1 ug vA142/RV01 (29) | 592 | 379 | 1000 | 327 | 500 | 270 | 672 | 447 | 483 |
| 0.1 ug vA142/RV01 (29) | 177 | 316 | 673 | 404 | 175 | 448 | 183 | 439 | 314 |
| 1 ug vA142/CNE17 | 423 | 439 | 201 | 567 | 229 | 625 | 992 | 315 | 419 |
| 0.1 ug vA142/CNE17 | 402 | 263 | 586 | 230 | 268 | 190 | 199 | 555 | 308 |
| 1 ug vA317/RV01 (29) | 379 | 892 | 373 | 851 | 1062 | 1453 | 1512 | 1000 | 841 |
| 1E6 VRP (F-full) | 2448 | 1627 | 2057 | 2767 | 1677 | 1879 | 3891 | 1238 | 2075 |
| 5 ug F trimer subunit/alum | 8433 | 13720 | 5940 | 7794 | 27047 | 26852 | 10612 | 16237 | 12685 |
| Naïve | 5 | 5 | | | | | | | 5 |

TABLE III-2

F-specific serum IgG titers of cotton rats, 2-8 animals per group, after intramuscular vaccination with the indicated vaccines on days 0 and 21. Serum was collected for antibody analysis on day 35 (2wp2). Data are represented as titers for individual animals and the geometric mean titer for each group. If an individual animal had a titer of <25 (limit of detection) it was assigned a titer of 5.

| Group | 2wp2 (day 35) F-specific serum IgG titers | | | | | | | | GMT |
|---|---|---|---|---|---|---|---|---|---|
| 1 ug vA318/RV01 (29) | 1500 | 2447 | 1358 | 586 | 322 | 1319 | 1152 | 864 | 1027 |
| 0.1 ug vA318/RV01 (29) | 219 | 197 | 317 | 560 | 330 | 340 | 237 | 154 | 274 |
| 1 ug vA318/CNE17 | 4366 | 2334 | 2281 | 1273 | 2280 | 1178 | 422 | 2009 | 1693 |
| 0.1 ug vA318/CNE17 | 3268 | 1485 | 1161 | 826 | 772 | 919 | 2688 | 489 | 1201 |
| 1 ug vA142/RV01 (29) | 5079 | 1013 | 2300 | 1178 | 2317 | 1388 | 2036 | 1485 | 1847 |
| 0.1 ug vA142/RV01 (29) | 664 | 748 | 1085 | 2670 | 403 | 874 | 763 | 857 | 871 |
| 1 ug vA142/CNE17 | 2395 | 2025 | 1889 | 6150 | 1585 | 4536 | 3259 | | 2791 |
| 0.1 ug vA142/CNE17 | 1446 | 298 | 3021 | 1745 | 2135 | 543 | 1152 | 1867 | 1242 |
| 1 ug vA317/RV01 (29) | 2121 | 3478 | 1939 | 2833 | 7048 | 9963 | 7064 | 3475 | 4032 |
| 1E6 VRP (F-full) | 3685 | 3953 | 5080 | 4517 | 1769 | 3153 | 3080 | 10074 | 3938 |
| 5 ug F trimer subunit/alum | 49635 | 98715 | 45626 | | 55704 | 63437 | 49799 | 36424 | 54526 |
| Naïve | 5 | 5 | | | | | | | 5 |

TABLE III-3

F-specific serum IgG titers of cotton rats, 2-8 animals per group, after intramuscular vaccination with the indicated vaccines on days 0 and 21. Serum was collected for antibody analysis on day 56 (5wp2). Data are represented as titers for individual animals and the geometric mean titer for each group. If an individual animal had a titer of <25 (limit of detection) it was assigned a titer of 5.

| Group | 5wp2 (day 56) F-specific serum IgG titers | | | | | | | | GMT |
|---|---|---|---|---|---|---|---|---|---|
| 1 ug vA318/RV01 (29) | 672 | 559 | 421 | 136 | 135 | 313 | 399 | 407 | 332 |
| 0.1 ug vA318/RV01 (29) | 95 | 166 | 163 | 81 | 192 | 313 | 120 | 122 | 144 |
| 1 ug vA318/CNE17 | 1239 | 1208 | 475 | 497 | 1398 | 754 | 247 | 1076 | 749 |
| 0.1 ug vA318/CNE17 | 1608 | 809 | 533 | 475 | 365 | 414 | 998 | 136 | 535 |

TABLE III-3-continued

F-specific serum IgG titers of cotton rats, 2-8 animals per group, after intramuscular vaccination with the indicated vaccines on days 0 and 21. Serum was collected for antibody analysis on day 56 (5wp2). Data are represented as titers for individual animals and the geometric mean titer for each group. If an individual animal had a titer of <25 (limit of detection) it was assigned a titer of 5.

| Group | 5wp2 (day 56) F-specific serum IgG titers | | | | | | | | GMT |
|---|---|---|---|---|---|---|---|---|---|
| 1 ug vA142/RV01 (29) | 1361 | 652 | 2068 | 634 | 2811 | 772 | 1426 | 709 | 1124 |
| 0.1 ug vA142/RV01 (29) | 213 | 435 | 663 | 1063 | 158 | 670 | 437 | 311 | 418 |
| 1 ug vA142/CNE17 | 824 | 841 | 615 | 2296 | 859 | 1522 | 1464 | | 1094 |
| 0.1 ug vA142/CNE17 | 618 | 183 | 784 | 492 | 617 | 374 | 495 | 799 | 501 |
| 1 ug vA317/RV01 (29) | 729 | 1822 | 709 | 1824 | 1523 | 2638 | 3088 | 925 | 1452 |
| 1E6 VRP (F-full) | 1377 | 1493 | 1711 | 1716 | 1052 | 1244 | 1170 | 4569 | 1596 |
| 5 ug F trimer subunit/alum | 23322 | 42848 | 25468 | | 18597 | 27586 | 25058 | 23551 | 25846 |
| Naïve | 5 | 5 | | | | | | | 5 |

TABLE III-4

F-specific serum IgG titers of cotton rats, 2-8 animals per group, after intramuscular vaccination on days 0 and 21 with the indicated vaccines. All cotton rats (except those in naive group) were also vaccinated with 5 μg of F trimer subunit/alum on day 56. Serum was collected for antibody analysis on day 70 (2wp3). Data are represented as titers for individual animals and the geometric mean titer for each group. If an individual animal had a titer of <25 (limit of detection) it was assigned a titer of 5.

| Group | 2wp3 (day 70) F-specific serum IgG titers | | | | | | | | GMT |
|---|---|---|---|---|---|---|---|---|---|
| 1 ug vA318/RV01 (29) | 26193 | 19838 | 14953 | 6158 | 9324 | 12742 | 19583 | 15384 | 14263 |
| 0.1 ug vA318/RV01 (29) | 922 | 2275 | 2385 | 962 | 2216 | 1674 | 2365 | 6482 | 2017 |
| 1 ug vA318/CNE17 | 14101 | 35083 | 19054 | 14272 | 35651 | 26929 | 8220 | 37314 | 21122 |
| 0.1 ug vA318/CNE17 | 36218 | 37967 | 22406 | 20415 | 12633 | 8447 | 35167 | 4677 | 18004 |
| 1 ug vA142/RV01 (29) | 14004 | 8393 | 16986 | 16213 | 11520 | 5990 | 15827 | 6846 | 11168 |
| 0.1 ug vA142/RV01 (29) | 5584 | 12724 | 14350 | 17334 | 6566 | 15322 | 12849 | 9538 | 11023 |
| 1 ug vA142/CNE17 | 11441 | 13405 | 17436 | 17696 | 18594 | 20947 | 22410 | | 17016 |
| 0.1 ug vA142/CNE17 | 18417 | 24557 | 12250 | 25534 | 25210 | 15650 | 18176 | 21074 | 19554 |
| 1 ug vA317/RV01 (29) | 7825 | 17564 | 11108 | 17105 | 10895 | 11840 | 25113 | 13684 | 13852 |
| 1E6 VRP (F-full) | 7872 | 11490 | 17166 | 14129 | 15972 | 14840 | 28172 | 13892 | 14574 |
| 5 ug F trimer subunit/alum | 36631 | 75674 | 51823 | | 41784 | 59712 | 37095 | 50029 | 48864 |
| Naïve | 5 | 5 | | | | | | | 5 |

TABLE III-5

RSV serum neutralization titers of cotton rats, 2-8 animals per group (2 per group for naive) after intramuscular vaccinations on days 0 and 21 with the indicated vaccines followed by 5 ug F trimer subunit/alum for all groups (except naive) on day 56. Serum was collected for analysis on days 21 (3wp1), 35 (2wp2), 56 (5wp2), and 70 (2wp3). Data are represented as 60% RSV neutralization titers for 2 pools of 3-4 animals per group and geometric mean titers of these 2 pools per group (one pool of 2 animals for naive group). If an individual pool had a titer of <20 (limit of detection) it was assigned a titer of 10.

| | RSV serum neutralization titers | | | | | | | | | | | |
|---|---|---|---|---|---|---|---|---|---|---|---|---|
| | 3wp1 (D21) | | | 2wp2 (D35) | | | 5wp2 (D56) | | | 2wp3 (D70) | | |
| group | pool 1 | pool 2 | GMT | pool 1 | pool 2 | GMT | pool 1 | pool 2 | GMT | pool 1 | pool 2 | GMT |
| 1 ug vA318/RV01 (29) | 51 | 65 | 58 | 194 | 92 | 134 | 112 | 110 | 111 | 8446 | 3381 | 6344 |
| 0.1 ug vA318/RV01 (29) | 33 | 50 | 41 | 112 | 92 | 102 | 87 | 45 | 63 | 5514 | 8013 | 6647 |
| 1 ug vA318/CNE17 | 60 | 68 | 64 | 278 | 176 | 221 | 139 | 137 | 138 | 9640 | 6157 | 7704 |
| 0.1 ug vA318/CNE17 | 90 | 65 | 76 | 188 | 374 | 265 | 62 | 153 | 97 | 6214 | 4274 | 5154 |
| 1 ug vA142/RV01 (29) | 69 | 86 | 77 | 243 | 476 | 340 | 113 | 360 | 202 | 3510 | 8390 | 5427 |
| 0.1 ug vA142/RV01 (29) | 33 | 38 | 35 | 68 | 63 | 65 | 59 | 53 | 56 | 3123 | 1582 | 2223 |
| 1 ug vA142/CNE17 | 41 | 139 | 75 | 315 | 374 | 343 | 246 | 128 | 177 | 7802 | 8083 | 7941 |
| 0.1 ug vA142/CNE17 | 30 | 68 | 45 | 122 | 142 | 132 | 59 | 217 | 113 | 5011 | 3424 | 4142 |
| 1 ug vA317/RV01 (29) | 38 | 10 | 19 | 220 | 381 | 290 | 166 | 240 | 200 | 3627 | 4837 | 4189 |

TABLE III-5-continued

RSV serum neutralization titers of cotton rats, 2-8 animals per group (2 per group for naive) after intramuscular vaccinations on days 0 and 21 with the indicated vaccines followed by 5 ug F trimer subunit/alum for all groups (except naive) on day 56. Serum was collected for analysis on days 21 (3wp1), 35 (2wp2), 56 (5wp2), and 70 (2wp3). Data are represented as 60% RSV neutralization titers for 2 pools of 3-4 animals per group and geometric mean titers of these 2 pools per group (one pool of 2 animals for naive group). If an individual pool had a titer of <20 (limit of detection) it was assigned a titer of 10.

| | RSV serum neutralization titers | | | | | | | | | | | |
|---|---|---|---|---|---|---|---|---|---|---|---|---|
| | 3wp1 (D21) | | | 2wp2 (D35) | | | 5wp2 (D56) | | | 2wp3 (D70) | | |
| group | pool 1 | pool 2 | GMT | pool 1 | pool 2 | GMT | pool 1 | pool 2 | GMT | pool 1 | pool 2 | GMT |
| 1E6 VRP (F-full) | 77 | 141 | 104 | 996 | 2379 | 1539 | 521 | 598 | 558 | 1329 | 6222 | 2876 |
| 5 ug F trimer subunit/alum | 294 | 683 | 448 | 4029 | 4931 | 4457 | 1613 | 1647 | 1630 | 4604 | 2863 | 3631 |
| naive | 10 | | 10 | 10 | | 10 | 10 | | 10 | | | |

TABLE III-6

F-specific serum IgG titers of cotton rats, 5 animals per group, after intramuscular vaccination on days 0 and 56 with the indicated vaccines. Serum was collected for antibody analysis on days 14 (2wp1), 21 (3wp1), 28 (4wp1), 35 (5wp1), 42 (6wp1), 56 (8wp1) and 70 (2wp2). Data are represented as titers for individual animals and the geometric mean titer for each group. If an individual animal had a titer of <25 (limit of detection) it was assigned a titer of 5.

| | | F-specific serum IgG titers | | | | | | |
|---|---|---|---|---|---|---|---|---|
| Group | animal # | 2wp1 (D14) | 3wp1 (D21) | 4wp1 (D28) | 5wp1 (D35) | 6wp1 (D42) | 8wp1 (D56) | 2wp2 (D70) |
| 1 ug | 666 | 346 | 537 | 488 | 420 | 339 | 383 | 5106 |
| vA317/ | 667 | 589 | 633 | 608 | 777 | 730 | 480 | 5340 |
| RV01 | 641 | 577 | 969 | 986 | 1286 | 673 | 460 | 5241 |
| (29) | 669 | 385 | 760 | 562 | 409 | 386 | 251 | 2742 |
| | 670 | 218 | 222 | 266 | 184 | 168 | 105 | 1520 |
| | GMT | 397 | 561 | 535 | 501 | 405 | 295 | 3589 |
| 1 ug | 671 | 292 | 319 | 307 | 305 | 186 | 171 | 1276 |
| vA317/ | 672 | 141 | 152 | 194 | 200 | 91 | 43 | 2379 |
| CNE17 | 673 | 161 | 516 | 440 | 389 | 236 | 150 | 5264 |
| | 674 | 239 | 499 | 455 | 422 | 281 | 162 | 4442 |
| | 675 | 292 | 240 | 157 | 129 | 72 | 43 | 2524 |
| | GMT | 215 | 313 | 285 | 265 | 152 | 95 | 2823 |

TABLE III-7

RSV serum neutralization titers of cotton rats, 5 animals per group, after intramuscular vaccination on days 0 and 56 with the indicated vaccines. Serum was collected for antibody analysis on days 14 (2wp1), 21 (3wp1), 28 (4wp1), 35 (5wp1), 42 (6wp1), 56 (8wp1) and 70 (2wp2). Data are represented as 60% RSV neutralization titers for 1 pools of 5 animals per group. If an individual pool had a titer of <20 (limit of detection) it was assigned a titer of 10.

| | RSV serum neutralization titers | | | | | | |
|---|---|---|---|---|---|---|---|
| Group | 2wp1 (D14) | 3wp1 (D21) | 4wp1 (D28) | 5wp1 (D35) | 6wp1 (D42) | 8wp1 (D56) | 2wp2 (D70) |
| 1 ug vA317/RV01 (29) | 52 | 82 | 90 | 106 | 80 | 101 | 1348 |
| 1 ug vA317/CNE17 | 34 | 38 | 36 | 33 | 25 | 36 | 143 |

Example IV

Sequential Administration of RNA and Protein to Rats (Study 2)

The vA142 replicon, which expresses the full-length wild type surface fusion glycoprotein of RSV with the fusion peptide deleted, was used for this experiment. Cotton rats, 4-8 animals per group, were given intramuscular vaccinations (100 μL in one leg) on days 0 and 21. All cotton rats in this study (except naive) were vaccinated with 5 μg F subunit+alum on day 49 (four weeks after the second vaccination).

Group 1 self-replicating RNA (vA142, 1 μg, RSV-F) formulated in LNPs (RV01(37). The LNP had the following composition: 40% DlinDMA, 10% DSPC, 48% Chol, 2% PEG DMG 2000 and an N:P ratio of 8:1. They were made using Method B, except a 175 μg RNA batch size was used.

Group 2 self-replicating RNA (vA142, 0.1 μg, RSV-F) formulated in LNPs (RV01(37). The LNP had the following composition: 40% DlinDMA, 10% DSPC, 48% Chol, 2% PEG DMG 2000 and an N:P ratio of 8:1. They were made using Method B, except a 175 μg RNA batch size was used.

Group 3 self-replicating RNA (vA142, 1 μg, RSV-F) formulated in LNPs (RV17(10). The LNP had the following composition: NVP-LJC305-NX-2 40%, DSPC— 10%, Chol-49.5%, PEG DMG 5000-0.5% and an N:P ratio of 8:1. They were made using Method A, except a 200 μg RNA batch size was used.

Group 4 self-replicating RNA (vA142, 0.1 μg, RSV-F) formulated in LNPs (RV17(10). The LNP had the following composition: NVP-LJC305-NX-2 40%, DSPC— 10%, Chol-49.5%, PEG DMG 5000-0.5% and an N:P ratio of 8:1. They were made using Method A, except a 200 μg RNA batch size was used.

Group 5 self-replicating RNA (vA142, 1 μg, RSV-F) formulated in LNPs (RV05(11). The LNP had the following composition: NVP-LGB046-NX-1 40%, 18:2 PE (DLoPE)-30%, Chol-28%, PEG DMG 2000-2% and an N:P ratio of 8:1. They were made using Method A, except a 200 μg RNA batch size was used.

Group 6 self-replicating RNA (vA142, 0.1 μg, RSV-F) formulated in LNPs (RV05(11). The LNP had the following composition: NVP-LGB046-NX-1 40%, 18:2 PE (DLoPE)-30%, Chol-28%, PEG DMG 2000-2% and an N:P ratio of 8:1. They were made using Method A, except a 200 μg RNA batch size was used.

Group 7 self-replicating RNA (vA142, 1.0 μg, RSV-F) formulated with CNE13 at an N:P ratio of 10:1.

Group 8 self-replicating RNA (vA142, 0.1 μg, RSV-F) formulated with CNE13 at an N:P ratio of 10:1.

Group 9 self-replicating RNA (vA142, 1.0 μg, RSV-F) formulated with CNE17 at an N:P ratio of 10:1.

Group 10 self-replicating RNA (vA142, 0.1 μg, RSV-F) formulated with CNE17 at an N:P ratio of 10:1.

Group 11 VRPs ($1\times10^6$ IU) expressing the full-length wild type surface fusion glycoprotein of RSV.

Group 12 RSV-F subunit protein vaccine (5 μg) adjuvanted with alum.

Group 13 a naïve control (3 animals).

Serum was collected for antibody analysis on days 0, 21, 35, 49, 64.

Results

F-specific serum IgG titers are shown in table IV-1 (day 21), IV-2 (day 35), IV-3 (day 49), IV-4 (day 64). RSV serum neutralizing antibody titers on days 21, 35, 49 and 64 are shown in table IV-5.

Conclusions

In this study, cotton rats were vaccinated with vA142 replicon formulated RV01, RV17, RV05, CNE17, or CNE13. Each of these vaccines was given at two doses (1.0 and 0.1 μg). After the first replicon vaccination, F-specific serum IgG titers were highest with RV01, followed by RV05, RV17 and CNE17 (40-67% of the F-specific IgG titer induced by a matched dose of vA142+RV01), and finally CNE13 (6-10% of the F-specific IgG titer induced by a matched dose of vA142+RV01). After the first replicon vaccination, RSV neutralization titers were approximately equal for RV01, RV05, RV17 and CNE17, whereas titers with CNE13 were lower (35-68% of the RSV neutralization titer induced by a matched dose of vA142+RV01). Titers in all groups were boosted by a homologous second vaccination given on day 21. After the second replicon vaccination, F-specific serum IgG titers were again highest with RV01, followed closely by RV05, RV17, and CNE17, and lower with CNE13 (25-33% of the F-specific IgG titer induced by a matched dose of vA142+RV01). Post second vaccination RSV neutralization titers generally followed this same trend, although exhibited more variability within the groups. RSV serum neutralization titers two weeks after the second vaccination were at least three fold lower in replicon groups than F subunit+alum or VRP groups.

All cotton rats in this study (except naive) were vaccinated with 5 μg F subunit+alum on day 49 (four weeks after the second vaccination). This third vaccination did not boost antibody titers in cotton rats previously vaccinated with subunit, but it provided a large boost to titers in cotton rats previously vaccinated with replicon, regardless of the formultion (RV01, RV17, RV05, CNE17, CNE13). In most cases the RSV serum neutralization titers after two replicon vaccinations followed by an F subunit+alum boost were equal to titers induced by two or three sequential F subunit+alum vaccinations.

For each group and time point a ratio of F-specific IgG titer to RSV neutralizing titer can be calculated, and is one indication of the quality of the antibody response. A lower ratio suggests that a larger fraction of the vaccine-induced antibody is capable of neutralizing RSV, and is therefore functional. The data from this study show that the F-specific IgG:RSV neutralizing antibody titer ratio is lower after vaccination with replicon or VRP than after vaccination with F subunit+alum. The lower F-specific IgG:RSV neutralizing antibody titer ratio set by two replicon or VRP vaccinations was maintained after a F subunit+alum boost.

TABLE IV-1

F-specific serum IgG titers of cotton rats, 3-8 animals per group, 21 days after intramuscular vaccination with the indicated vaccines. Data are represented as titers for individual animals and the geometric mean titer for each group. If an individual animal had a titer of <25 (limit of detection) it was assigned a titer of 5.

| Group | 3wp1 (day 21) F-specific serum IgG titers | | | | | | | | GMT |
|---|---|---|---|---|---|---|---|---|---|
| 1 ug vA142/RV01 (37) | 334 | 316 | 943 | 628 | 787 | 550 | 546 | 639 | 558 |
| 0.1 ug vA142/RV01 (37) | 193 | 90 | 251 | 66 | 30 | 82 | 89 | 388 | 112 |
| 1 ug vA142/RV17 (10) | 861 | 131 | 378 | 262 | 736 | 200 | 327 | 265 | 330 |
| 0.1 ug vA142/RV17 (10) | 188 | 140 | 5 | 41 | 111 | 28 | | | 51 |
| 1 ug vA142/RV05 (11) | | 376 | 630 | 370 | 383 | 232 | 126 | 551 | 342 |
| 0.1 ug vA142/RV05 (11) | 93 | 192 | 38 | 181 | 5 | 57 | 5 | 202 | 49 |
| 1 ug vA142/CNE13 | 5 | 185 | 681 | 268 | 192 | 455 | 415 | 441 | 201 |
| 0.1 ug vA142/CNE13 | 164 | 49 | 5 | 66 | 44 | 243 | 207 | 184 | 76 |
| 1 ug vA142/CNE17 | 43 | 214 | 46 | 5 | 5 | 33 | 48 | 129 | 35 |
| 0.1 ug vA142/CNE17 | 5 | 5 | 5 | 5 | 53 | 186 | 5 | 5 | 11 |
| 1E6 VRP (F-full) | 1624 | 1101 | 3111 | 3952 | 1944 | 1097 | 573 | 1271 | 1555 |
| 5 ug F trimer subunit/alum | 1249 | 488 | 24687 | 17552 | 29911 | 22928 | 16624 | | 8425 |
| naive | 5 | 5 | 5 | | | | | | 5 |

TABLE IV-2

F-specific serum IgG titers of cotton rats, 3-8 animals per group, after intramuscular vaccination with the indicated vaccines on days 0 and 21. Serum was collected for antibody analysis on day 35 (2wp2). Data are represented as titers for individual animals and the geometric mean titer for each group. If an individual animal had a titer of <25 (limit of detection) it was assigned a titer of 5.

| Group | 2wp2 (day 35) F-specific serum IgG titers | | | | | | | | GMT |
|---|---|---|---|---|---|---|---|---|---|
| 1 ug vA142/RV01 (37) | 3608 | 1966 | 4220 | 2961 | 3896 | 4212 | 14834 | 2680 | 3938 |
| 0.1 ug vA142/RV01 (37) | 1454 | 412 | 2127 | 934 | 1138 | 2750 | 2184 | 1839 | 1403 |
| 1 ug vA142/RV17 (10) | 3488 | 1892 | 3568 | 1915 | 3094 | 1507 | 7845 | 3266 | 2927 |
| 0.1 ug vA142/RV17 (10) | 599 | 1153 | 177 | 614 | 850 | 254 | | | 503 |

TABLE IV-2-continued

F-specific serum IgG titers of cotton rats, 3-8 animals per group, after intramuscular vaccination with the indicated vaccines on days 0 and 21. Serum was collected for antibody analysis on day 35 (2wp2). Data are represented as titers for individual animals and the geometric mean titer for each group. If an individual animal had a titer of <25 (limit of detection) it was assigned a titer of 5.

| Group | 2wp2 (day 35) F-specific serum IgG titers | | | | | | | | GMT |
|---|---|---|---|---|---|---|---|---|---|
| 1 ug vA142/RV05 (11) | | 2735 | 2030 | 3331 | 4957 | 6336 | 1957 | 3067 | 3207 |
| 0.1 ug vA142/RV05 (11) | 1833 | 1490 | 1997 | 584 | 1307 | 1328 | 82 | 2348 | 1008 |
| 1 ug vA142/CNE13 | 1971 | 3234 | 15961 | 1679 | 3006 | 4928 | 1850 | 2366 | 3203 |
| 0.1 ug vA142/CNE13 | 3380 | 1879 | 1348 | 4032 | 2423 | 1902 | 1311 | 2583 | 2195 |
| 1 ug vA142/CNE17 | 241 | 3321 | 838 | 522 | 452 | 986 | 1646 | 2759 | 958 |
| 0.1 ug vA142/CNE17 | 171 | 997 | 419 | 267 | 225 | 1270 | 368 | 983 | 459 |
| 1E6 VRP (F-full) | 4944 | 5023 | 5603 | 12192 | 14184 | 5764 | 6392 | 10678 | 7448 |
| 5 ug F trimer subunit/alum | 60431 | 34850 | 94259 | 116203 | 75778 | 108013 | 124309 | | 81297 |
| naive | 5 | 5 | 5 | | | | | | 5 |

TABLE IV-3

F-specific serum IgG titers of cotton rats, 3-8 animals per group, after intramuscular vaccination with the indicated vaccines on days 0 and 21. Serum was collected for antibody analysis on day 49 (4wp2). Data are represented as titers for individual animals and the geometric mean titer for each group. If an individual animal had a titer of <25 (limit of detection) it was assigned a titer of 5.

| Group | 4wp2 (day 49) F-specific serum IgG titers | | | | | | | | GMT |
|---|---|---|---|---|---|---|---|---|---|
| 1 ug vA142/RV01 (37) | 1681 | 961 | 2154 | 2220 | 2861 | 2710 | 9271 | 1870 | 2383 |
| 0.1 ug vA142/RV01 (37) | 1271 | 254 | 935 | 671 | 870 | 1446 | 1485 | 1650 | 943 |
| 1 ug vA142/RV17 (10) | 3595 | 1977 | 2836 | 1408 | 4314 | 1075 | 2652 | 1811 | 2239 |
| 0.1 ug vA142/RV17 (10) | 745 | 787 | 137 | 468 | 752 | 570 | | | 503 |
| 1 ug vA142/RV05 (11) | | 2309 | 1028 | 1957 | 3162 | 2916 | 2343 | 2123 | 2151 |
| 0.1 ug vA142/RV05 (11) | 1899 | 897 | 1234 | 855 | 482 | 488 | 5 | 2268 | 513 |
| 1 ug vA142/CNE13 | 922 | 2475 | 7883 | 964 | 1626 | 3663 | 1241 | 1124 | 1861 |
| 0.1 ug vA142/CNE13 | 1702 | 1234 | 1090 | 2190 | 1261 | 1066 | 878 | 1766 | 1341 |
| 1 ug vA142/CNE17 | 238 | 6470 | 884 | 879 | 530 | 1066 | 1186 | 4942 | 1188 |
| 0.1 ug vA142/CNE17 | 237 | 613 | 211 | 186 | 158 | 744 | 301 | 715 | 331 |
| 1E6 VRP (F-full) | 2537 | 2594 | 1662 | 6465 | 10802 | 3442 | 3796 | 6875 | 4023 |
| 5 ug F trimer subunit/alum | 36694 | 18062 | 65268 | 62018 | 55760 | 89468 | 110556 | | 54776 |
| naive | 5 | 5 | 5 | | | | | | 5 |

TABLE IV-4

F-specific serum IgG titers of cotton rats, 3-8 animals per group, after intramuscular vaccination on days 0 and 21 with the indicated vaccines. All cotton rats (except those in naive group) were also vaccinated with 5 μg of F trimer subunit/alum on day 49 (4wp2). Serum was collected for antibody analysis on day 64 (~2wp3). Data are represented as titers for individual animals and the geometric mean titer for each group. If an individual animal had a titer of <25 (limit of detection) it was assigned a titer of 5.

| Group | ~2wp3 (day 64) F-specific serum IgG titers | | | | | | | | GMT |
|---|---|---|---|---|---|---|---|---|---|
| 1 ug vA142/RV01 (37) | 15772 | 6101 | 14780 | 16995 | 17241 | 25359 | 27454 | 19522 | 16563 |
| 0.1 ug vA142/RV01 (37) | 25676 | 13765 | 19597 | 11461 | 7832 | 16681 | 12694 | 20780 | 15123 |
| 1 ug vA142/RV17 (10) | 20604 | 22426 | 56417 | 29296 | 53866 | 14992 | 19221 | 17081 | 25900 |
| 0.1 ug vA142/RV17 (10) | 20857 | 24082 | 9670 | 15857 | 19641 | 53866 | | | 20821 |
| 1 ug vA142/RV05 (11) | | 32193 | 23171 | 22416 | 28063 | 19311 | 34924 | 16713 | 24494 |
| 0.1 ug vA142/RV05 (11) | 38208 | 25998 | 17304 | 20634 | 14551 | 19200 | 1528 | 19917 | 15308 |
| 1 ug vA142/CNE13 | 10884 | 15381 | 52436 | 18745 | 22023 | 20262 | 24805 | 25415 | 21537 |
| 0.1 ug vA142/CNE13 | 17474 | 35952 | 37393 | 23943 | 39407 | 16807 | 17189 | 54958 | 27753 |
| 1 ug vA142/CNE17 | 7543 | 77979 | 42889 | 7306 | 14673 | 28679 | 37562 | 54571 | 25128 |

TABLE IV-4-continued

F-specific serum IgG titers of cotton rats, 3-8 animals per group, after intramuscular vaccination on days 0 and 21 with the indicated vaccines. All cotton rats (except those in naive group) were also vaccinated with 5 μg of F trimer subunit/alum on day 49 (4wp2). Serum was collected for antibody analysis on day 64 (~2wp3). Data are represented as titers for individual animals and the geometric mean titer for each group. If an individual animal had a titer of <25 (limit of detection) it was assigned a titer of 5.

| Group | ~2wp3 (day 64) F-specific serum IgG titers | | | | | | | | GMT |
|---|---|---|---|---|---|---|---|---|---|
| 0.1 ug vA142/CNE17 | 21964 | 22163 | 35860 | 33383 | 23572 | 17133 | 39531 | 110957 | 31748 |
| 1E6 VRP (F-full) | 17455 | 27475 | 15866 | 20471 | 34132 | 29351 | 22155 | 56379 | 25777 |
| 5 ug F trimer subunit/alum | 83936 | 38397 | 100297 | 97227 | 84404 | 63790 | 159161 | | 82911 |
| naive | 5 | 5 | 5 | | | | | | 5 |

TABLE IV-5

RSV serum neutralization titers of cotton rats, 2-8 animals per group (2 per group for naive) after intramuscular vaccinations with the indicated vaccines on days 0 and 21 (3wp1). All animals (except naive) were then vaccinated with 5 μg F trimer subunit/alum on day 49 (4wp2). Serum was collected for analysis on days 21 (3wp1), 35 (2wp2), 49 (4wp2), and 64 (~2wp3). Data are represented as 60% RSV neutralization titers for 2 pools of 3-4 animals per group and geometric mean titers of these 2 pools per group (one pool of 3 animals for naive group). If an individual pool had a titer of <20 (limit of detection) it was assigned a titer of 10.

| | RSV serum neutralization titers | | | | | | | | | | | |
|---|---|---|---|---|---|---|---|---|---|---|---|---|
| | 3wp1 (D21) | | | 2wp2 (D35) | | | 4wp2 (D49) | | | ~2wp3 (D64) | | |
| Group | pool 1 | pool 2 | GMT | pool 1 | pool 2 | GMT | pool 1 | pool 2 | GMT | pool 1 | pool 2 | GMT |
| 1 ug vA142/RV01 (37) | 61 | 72 | 66 | 525 | 1184 | 788 | 230 | 407 | 306 | 2742 | 2580 | 161 |
| 0.1 ug vA142/RV01 (37) | 26 | 26 | 26 | 105 | 251 | 162 | 33 | 101 | 58 | 887 | 3542 | 1772 |
| 1 ug vA142/RV17 (10) | 87 | 54 | 69 | 301 | 281 | 291 | 195 | 201 | 198 | 2177 | 3266 | 3221 |
| 0.1 ug vA142/RV17 (10) | 26 | 23 | 24 | 128 | 40 | 72 | 49 | 38 | 43 | 2219 | 581 | 1135 |
| 1 ug vA142/RV05 (11) | 70 | 80 | 75 | 468 | 428 | 448 | 178 | 228 | 201 | 3962 | 8295 | 5733 |
| 0.1 ug vA142/RV05 (11) | 29 | 25 | 27 | 610 | 226 | 371 | 192 | 138 | 163 | 3893 | 1541 | 2449 |
| 1 ug vA142/CNE13 | 32 | 54 | 42 | 358 | 270 | 311 | 181 | 113 | 143 | 709 | 1987 | 1187 |
| 0.1 ug vA142/CNE13 | 38 | 39 | 38 | 523 | 118 | 248 | 77 | 131 | 100 | 2080 | 1553 | 1797 |
| 1 ug vA142/CNE17 | 21 | 25 | 23 | 568 | 142 | 284 | 420 | 156 | 256 | 4444 | 6149 | 5227 |
| 0.1 ug vA142/CNE17 | 10 | 31 | 18 | 65 | 56 | 60 | 37 | 52 | 44 | 3040 | 5984 | 4265 |
| 1E6 VRP (F-full) | 172 | 109 | 137 | 2472 | 3354 | 2879 | 734 | 1442 | 1029 | 1768 | 2085 | 1920 |
| 5 ug F trimer subunit/alum | 248 | 379 | 307 | 2031 | 3252 | 2570 | 607 | 2081 | 1124 | 2720 | 3085 | 2897 |
| naive | 10 | 10 | | | | | | | | 10 | | 10 |

Example V

Sequential Administration of RNA and Protein to Cattle

The vA317 replicon that expresses the surface fusion glycoprotein of RSV (RSV-F) was used for this experiment. Calves (5 per group) were given intramuscular vaccinations on days 0, 21, 86 and 146. RNA and PBS vaccines were administered as 1.0 mL split doses on each side of the neck (2 mL total dose). The Triangle 4 product (a vaccine for prevention of disease caused by bovine respiratory syncytial virus as well as other pathogens; Ft. Dodge Animal Health) was administered as labeled (2.0 mL dose on one side of the neck). The RSV-F subunit protein vaccine (15 μg) adjvuanted with MF59 was administered as 1.0 mL split doses on each side of the neck (2 mL total dose). Self-replicating RNA (vA317, 60 μg) was formulated in LNP (RV01(01), with the following composition: 40% DlinDMA, 10% DSPC, 48% Chol, 2% PEG DMG 2000, N:P ratio of 8:1 and was made using Method C, except a 1.5 mg RNA batch size was used. Self replicating RNA (vA317, 60 μg) was formulated with CNE17 at an N:P ratio of 10:1.

Calves were vaccinated three times with RNA/CNE, RNA/LNP, a commercial RSV vaccine (Triangle 4), or PBS. It should be noted that the RNA vaccines in this study encoded human RSV F while the Triangle 4 contained bovine RSV F (the RSV F protein is highly conserved between BRSV and HRSV). All calves were vaccinated a fourth time with RSV-F subunit/MF59. Serum was collected for antibody analysis on days 0, 14, 21, 35, 42, 56, 63, 86, 100, 107, 114, 121, 128, 135, 146, 160, 167, 174, 181, 188, 195, and 202.

Results

F-specific serum IgG titers on days 21, 35, 56, 86, 100, 121, 146, 160, 181 and 202 are shown in table V-1. RSV serum neutralizing antibody titers on days 35, 56, 100, 107, 114, 146, 160, 167, 174 are shown in table V-2.

Conclusions

The data from this study provided proof of concept for RNA replicon RSV vaccines in large animals, with two of the five RNA/CNE-vaccinated calves demonstrating good neutralizing antibody titers after the third vaccination as measured by the complement-independent HRSV neutralization assay. In the complement-enhanced HRSV neutralization assay, all vaccinated calves had good neutralizing antibody titers after the second RNA vaccination regardless of the formulation. Furthermore, both RNA/CNE and RNA/LNP elicited F-specific serum IgG titers that were detected in a few calves after the second vaccination and in all calves after the third vaccination. Proof of concept for RNA replicon vaccines in large animals is particularly important in light of the loss in potency observed previously with DNA-based vaccines when moving from small animal models to larger animals and humans. A typical dose for DNA in cows is 0.5-1.0 mg (Taylor 2005, Boxus 2007), so it is very encouraging that immune responses were induced with these 1$^{st}$ generation RNA vaccines at a 60 μg dose. The RNA/LNP vaccine was also shown to be superior to DNA in the mouse model experiments.

These data also suggest that CNE-formulated RNA is more immunogenic than the LNP-formulated RNA in calves. This was evident in higher ELISA titers after the second vaccination, and higher neutralization titers after the third vaccination with the former formulation. RSV-F subunit/MF59 was able to boost the IgG response in all previously vaccinated calves, and boost complement-independent HRSV neutralization titers of calves previously vaccinated with RNA.

TABLE V-1

F-specific serum IgG titers of cows, 5 animals per group, after intramuscular vaccinations with the indicated vaccines on days 0, 21, 86. All cows were vaccinated with 15 μg of F trimer subunit + MF59 on day 146. Serum was collected for antibody analysis prior to vaccination (pre-immune) and on days 21, 35, 56, 86, 100, 121, 146, 160, 181, and 202. Data are represented as titers for individual cows and the geometric mean titers of 5 individual cows per group. If an individual animal had a titer of <25 (limit of detection) it was assigned a titer of 5.

| | | F-specific serum IgG titers | | | | | | | | | | |
|---|---|---|---|---|---|---|---|---|---|---|---|---|
| Group | animal # | pre-immune | 3wp1 D21 | 2wp2 D35 | 5wp2 D56 | ~9wp2 D86 | 2wp3 D100 | 5wp3 D121 | 7wp3 D146 | 2wp4 D160 | 5wp4 D181 | 8wp4 D202 |
| PBS | 2 | 5 | 5 | 5 | 5 | 5 | 5 | 5 | 5 | 36 | 49 | 139 |
| | 5 | 5 | 5 | 5 | 5 | 5 | 5 | 5 | 5 | 76 | 179 | 154 |
| | 6 | 5 | 5 | 5 | 5 | 5 | 5 | 5 | 5 | 331 | 368 | 322 |
| | 11 | 5 | 5 | 5 | 5 | 5 | 5 | | | | | |
| | 20 | 5 | 5 | 5 | 5 | 5 | 5 | 5 | 5 | 5 | 29 | 73 |
| | GMT | 5 | 5 | 5 | 5 | 5 | 5 | 5 | 5 | 46 | 98 | 150 |
| 60 ug | 1 | 5 | 5 | 62 | 36 | 28 | 4182 | 1518 | 193 | 141475 | 28402 | 6864 |
| vA317/ | 7 | 5 | 5 | 5 | 5 | 5 | 510 | 328 | 32 | 11228 | 4560 | 1437 |
| RV01 | 8 | 5 | 5 | 34 | 5 | 5 | 133 | 223 | 98 | 11078 | 3637 | 1228 |
| (01) | 10 | 5 | 5 | 5 | 30 | 86 | 1061 | | | | | |
| | 13 | 5 | 5 | 5 | 5 | 49 | 887 | 301 | 51 | 10583 | 5162 | 2531 |
| | GMT | 5 | 5 | 12 | 11 | 20 | 768 | 428 | 74 | 20774 | 7022 | 2353 |
| 60 ug | 14 | 5 | 5 | 5 | 5 | 5 | 191 | 177 | 5 | 4609 | 2093 | 1121 |
| vA317/ | 17 | 5 | 5 | 1561 | 828 | 610 | 1730 | 1785 | 110 | 6357 | 2912 | 1611 |
| CNE17 | 19 | 5 | 5 | 243 | 167 | 228 | 3239 | 1604 | 411 | 86280 | 20052 | 10056 |
| | 22 | 5 | 5 | 5 | 58 | 155 | 278 | 216 | 132 | 16082 | 8084 | 811 |
| | 23 | 5 | 5 | 5 | 5 | 5 | 927 | 410 | 55 | 967 | 2697 | 2601 |
| | GMT | 5 | 5 | 34 | 46 | 56 | 773 | 538 | 70 | 8297 | 4843 | 2073 |
| Triangle 4 | 3 | 5 | 5 | 4014 | 3242 | 2920 | 24028 | 18303 | 961 | 25068 | 14047 | 4876 |
| | 9 | 5 | 5 | 930 | 715 | 686 | 2552 | 7514 | 325 | 12088 | 4099 | 2143 |
| | 15 | 5 | 5 | 1274 | 373 | 145 | 1363 | 1095 | 140 | 8976 | 2814 | 1673 |
| | 18 | 5 | 5 | 413 | 97 | 109 | 74* | 1058* | 109* | 37419* | 11207* | 4461* |
| | 24 | 5 | 5 | 9200 | 2319 | 1138 | 1611 | 400 | 292 | 11771 | 3209 | 1184 |
| | GMT | 5 | 5 | 1784 | 721 | 514 | 3406 | 2786 | 336 | 13376 | 4775 | 2133 |

*Cow #18 was vaccinated with vA317/CNE17 vaccine at D86 (instead of Triangle 4), and therefore its titers are not included in the GMT from day 100 onwards.

TABLE V-2

RSV serum neutralization titers of cows, 5 animals per group, after intramuscular vaccinations with the indicated vaccines on days 0, 21, 86. All cows were vaccinated with 15 μg of F trimer subunit + MF59 on day 146. Serum was collected for analysis prior to vaccination (pre-immune) and on days 35, 56, 100, 107, 114, 146, 160, 167, and 174. Data are represented as 60% RSV neutralization titers of individual cows and the geometric mean titers of 5 individual cows per group. If an individual animal had a titer of <20 (limit of detection) it was assigned a titer of 10.

| | | RSV serum neutralization titers | | | | | | | | | |
|---|---|---|---|---|---|---|---|---|---|---|---|
| Group | animal # | pre-immune | 2wp2 D35 | 5wp2 D56 | 2wp3 D100 | 3wp3 D107 | 4wp3 D114 | 8wp3 D146 | 2wp4 D160 | 3wp4 D167 | 4wp4 D174 |
| PBS | 2 | 10 | 10 | 10 | 27 | 26 | 10 | 38 | 10 | 10 | 10 |
| | 5 | 10 | 10 | 10 | 23 | 24 | 21 | 10 | 10 | 10 | 10 |
| | 6 | 27 | 10 | 10 | 10 | 32 | 27 | 10 | 10 | 10 | 10 |
| | 11 | 10 | 10 | 10 | 10 | 10 | 22 | | | | |
| | 20 | 10 | 10 | 10 | 10 | 10 | 24 | 10 | 10 | 10 | 10 |

TABLE V-2-continued

RSV serum neutralization titers of cows, 5 animals per group, after intramuscular vaccinations with the indicated vaccines on days 0, 21, 86. All cows were vaccinated with 15 μg of F trimer subunit + MF59 on day 146. Serum was collected for analysis prior to vaccination (pre-immune) and on days 35, 56, 100, 107, 114, 146, 160, 167, and 174. Data are represented as 60% RSV neutralization titers of individual cows and the geometric mean titers of 5 individual cows per group. If an individual animal had a titer of <20 (limit of detection) it was assigned a titer of 10.

| | | RSV serum neutralization titers | | | | | | | | | |
|---|---|---|---|---|---|---|---|---|---|---|---|
| Group | animal # | pre-immune | 2wp2 D35 | 5wp2 D56 | 2wp3 D100 | 3wp3 D107 | 4wp3 D114 | 8wp3 D146 | 2wp4 D160 | 3wp4 D167 | 4wp4 D174 |
| | GMT | 12 | 10 | 10 | 14 | 18 | 20 | 14 | 10 | 10 | 10 |
| 60 ug | 1 | 31 | 10 | 10 | 30 | 35 | 39 | 10 | 310 | 156 | 78 |
| vA317/ | 7 | 10 | 10 | 10 | 21 | 10 | 35 | 10 | 25 | 10 | 10 |
| RV01 | 8 | 10 | 10 | 10 | 22 | 10 | 10 | 10 | 29 | 28 | 10 |
| (01) | 10 | 10 | 10 | 10 | 10 | 10 | 10 | | | | |
| | 13 | 10 | 10 | 10 | 26 | 10 | 10 | 27 | 21 | 10 | 27 |
| | GMT | 13 | 10 | 10 | 20 | 13 | 17 | 13 | 47 | 26 | 21 |
| 60 ug | 14 | 10 | 10 | 10 | 10 | 10 | 21 | 10 | 10 | 10 | 10 |
| vA317/ | 17 | 10 | 10 | 10 | 99 | 93 | 123 | 10 | 145 | 110 | 75 |
| CNE17 | 19 | 10 | 10 | 10 | 173 | 179 | 132 | 48 | 420 | 379 | 233 |
| | 22 | 10 | 10 | 32 | 10 | 35 | 39 | 10 | 82 | 52 | 58 |
| | 23 | 10 | 10 | 10 | 10 | 28 | 28 | 10 | 22 | 28 | 10 |
| | GMT | 10 | 10 | 13 | 28 | 44 | 52 | 14 | 64 | 57 | 40 |
| Triangle 4 | 3 | 10 | 30 | 39 | 49 | 46 | 39 | 27 | 31 | 24 | 21 |
| | 9 | 21 | 10 | 10 | 42 | 33 | 60 | 10 | 10 | 67 | 23 |
| | 15 | 10 | 10 | 10 | 23 | 30 | 34 | 10 | 37 | 27 | 10 |
| | 18 | 10 | 10 | 10 | 10 | 60* | 62* | 10* | 67* | 70* | 62* |
| | 24 | 10 | 27 | 10 | 51 | 45 | 35 | 10 | 30 | 10 | 10 |
| | GMT | 12 | 15 | 13 | 39 | 38 | 41 | 13 | 24 | 26 | 15 |

*Cow #18 was vaccinated with vA317/CNE17 vaccine at D86 (instead of Triangle 4), and therefore its titers are not included in the GMT from day 100 onwards.

Example VI

Alphavirus Vrp Prime, Protein Boost and Coadmintration of RNA and Subunit

Mice were immunized three times, three weeks apart with VRPs expressing the gH/gL complex, VRPs expressing green fluorescent protein (VRP-G), purified gH/gL subunit with or without MF59, different sequences of VRP or VRP-G followed by subunit in PBS or MF59, VRPs expressing the gH/gL complex mixed with purified gH/gL subunit, or VRP-G mixed with purified gH/gL subunit (see Table VI-1). A group of control mice did not receive any vaccine, and additional control groups included GFP VRPs to determine whether any effects from VRP prime were specific to the encoded antigen.

TABLE VI-1

| Group | Mice | Vaccinations | Antigen | Formulation | Dose |
|---|---|---|---|---|---|
| 1 | 4 | 3 | None | — | — |
| 2 | 8 | 3 | gH FL/gL VRP | — | $10^6$ IU |
| 3 | 8 | 3 | gHsol/gL subunit | PBS | 1 μg |
| 4 | 8 | 3 | gHsol/gL subunit | MF59 | 1 μg |
| 5 | 8 | 3 | 1st dose VEE gH FL/gL VRP | — | $10^6$ IU |
| | | | 2nd and 3rd dose gHsol/gL subunit | MF59 | 1 μg |
| 6 | 8 | 3 | 1st and 2nd doses VEE gH FL/gL VRP | — | $10^6$ IU<br>1 μg |
| | | | 3rd dose gHsol/gL subunit | MF59 | |
| 7 | 8 | 3 | 1st dose VEE GFP VRP (VRP-G) | — | $10^6$ IU |
| | | | 2nd and 3rd dose gHsol/gL subunit | MF59 | 1 μg |
| 8 | 8 | 3 | 1st and 2nd doses VRP-G | — | $10^6$ IU |
| | | | 3rd dose gHsol/gL subunit | MF59 | 1 μg |
| 9 | 8 | 3 | 1st dose gH FL/gL VRP | — | $10^6$ IU |
| | | | 2nd and 3rd dose gHsol/gL subunit | PBS | 1 μg |
| 10 | 8 | 3 | 1st and 2nd doses gH FL/gL VRP | — | $10^6$ IU |
| | | | 3rd dose gHsol/gL subunit | PBS | 1 μg |
| 11 | 8 | 3 | gH FL/gL VRP + gHsol/gL subunit MIXED | — | $10^6$ IU + 1 μg |
| 12 | 8 | 3 | GFP VRP + gHsol/gL subunit MIXED | — | $10^6$ IU + 1 μg |

Sera were harvested three weeks after each immunization and used for ELISA to determine binding antibody titers, using the same purified gH/gL antigen in the assay as in the subunit vaccine. The sera were also used for HCMV microneutralization assay using TB40 infection of ARPE-19 epithelial cells.

Four weeks after the third immunization, spleens were extracted from sacrificed mice. Spleen cells were stimulated in vitro with purified gH/gL protein or a pool of 15-mer peptides (overlapping by 11 amino acids) corresponding approximately to the c-terminal half of the gH protein, stained for CD4, CD8, and cytokine expression, and analyzed using flow cytometry.

Vaccination with the gH/gL VRPs elicited strongly neutralizing antibody responses (FIG. 1). Purified gH/gL subunit elicited modest responses without adjuvant. When formulated with MF59 potently neutralizing antibody responses that were at least as strong as those elicited by gH/gL VRPs were elicted. Different VRP prime, subunit/MF59 boost regimens did not increase the neutralizing titer compared to subunit. Substituting the gH/gL VRP for a GFP-expressing GFP in the prime-boost regimens had the expected result of decreasing the magnitude of the neutralizing response. VRP prime followed by unadjuvanted protein boost did not increase neutralizing titers compared to subunit/MF59 alone. The titers for any given prime boost regimen were comparable when the subunit boost was delivered with or without MF59.

Figure 2:
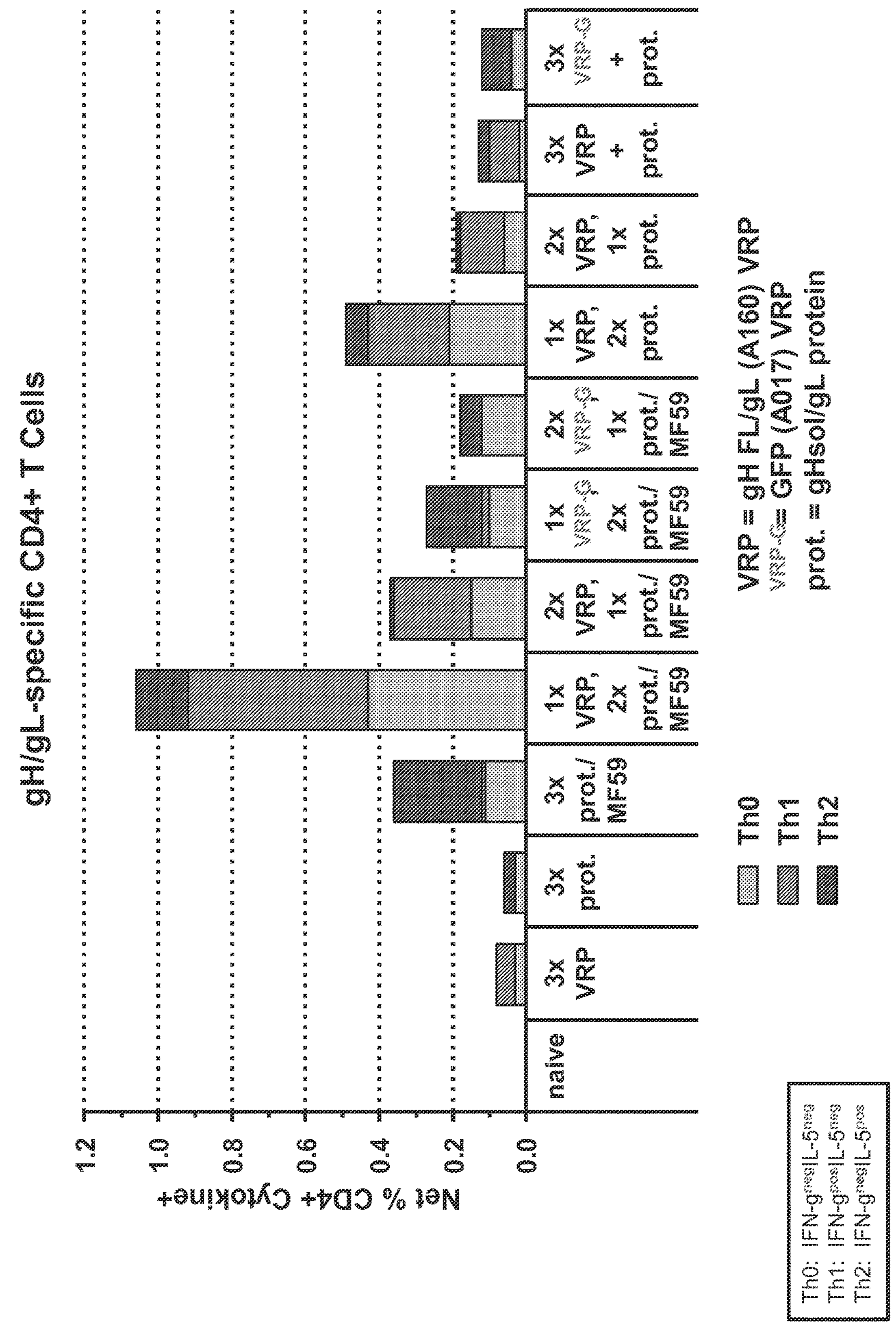
FIG. 2 is a graph showing the percentage of cytokine positive antigen-specifc CD4 T cells at 4wp3 (day 69) after immunization using the dose immunization regimen described in FIG. 1 and Example VI, Table VI-1. Splenocytes were restimulated in vitro with gHsol/gL protein.

Vaccination with VRPs or subunit without adjuvant elicited weak CD4+ T cell responses (FIG. 2). Subunit adjuvanted with MF59 elicited CD4 cells with a Th2/Th0 phenotype. The only combination of VRPs and subunit (prime-boost or mixed modality) that elicited significantly more CD4 cells than subunit/MF59 was one dose of VRPs followed by two doses of subunit/MF59. These cells had a Th1/Th0 phenotype; all groups that received a gH/gL-expressing VRP elicited cells with this phenotype. In contrast, priming or co-immunizing with GFP-expressing VRPs did not change the T cell phenotype compared to subunit/MF59.

Figure 3:
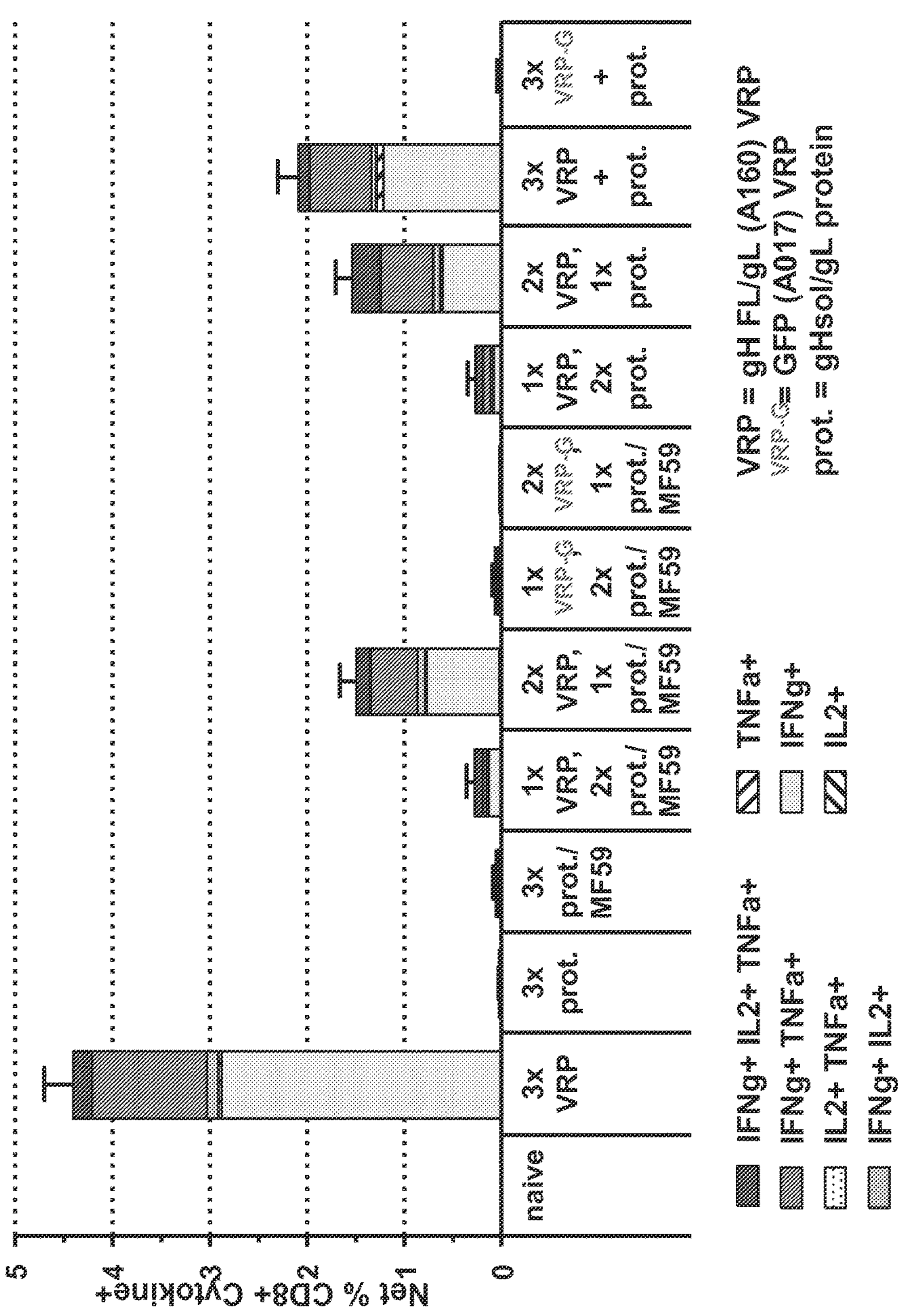
FIG. 3 is a graph showing the percentage of cytokine positive antigen-specific CD8 T cells at 4wp3 (day 69) after immunization using the dose immunization regimen described in FIG. 1 and Example VI, Table VI-1. Splenocytes were restimulated in vitro with gH peptide pool 2.

Vaccination with VRPs expressing gH/gL elicited robust CD8+ T cell responses (FIG. 3). No prime boost combination tested or co-administration with subunit improved the responses.

The data from this study showed gH/gL prime followed by gH/gL subunit boost elicited strong neutralizing titers with a concomitant CD4 T cell response, which may affect durability of the responses. As a result, following VRP prime, there is no need to adjuvant the subunit boost with MF59. VRPs that expressed a heterologous antigen did not prime animals for subsequent subunit boost, and did not adjuvant responses to subunit when co-delivered.

Example VII

A Sam™ Vaccine Prime, Protein Boost and Coadministration of RNA and Subunit Using the Hcmv Pentameric Antigen Mice were immunized three times, three weeks apart with a SAM vaccine, which is a self replicating RNA as described herein, encoding the CMV pentameric complex (gH/gL/UL128/UL130/UL131), purified pentameric subunit adjuvanted with MF59, different sequences of SAM followed by subunit in MF59, or a combination of the two (Table VII-1). The SAM vaccine was encapsulated in synthetic LNPs for non-viral delivery. A group of control mice did not receive any vaccine.

TABLE VII-1

| Group | No. Mice | No. Doses | Antigen | Formulation | Dose |
|---|---|---|---|---|---|
| 1 | 4 | — | — | — | 1 |
| 2 | 8 | 3 | SAM vaccine encoding pentameric complex (Penta SAM) | Lipid nanoparticle (LNP) | 1 microgram |
| 3 | 8 | 3 | Purified pentameric complex (Penta subunit) | MF59 | 1 microgram |
| 4 | 8 | 3 | 1st Penta SAM vaccine<br>2nd and 3rd Penta subunit | LNP<br>MF59 | 1 microgram |
| 5 | 8 | 3 | 1st and 2nd Penta SAM vaccine<br>3rd Penta subunit | LNP<br>MF59 | 1 microgram |
| 6 | 8 | 3 | Penta SAM vaccine + Penta subunit (mixed) | LNP | 1 microgram + 1 microgram |

Sera were harvested three weeks after each immunization and used for ELISA to determine binding antibody titers, using the same purified antigen in the assay as in the subunit vaccine. The sera were also used for HCMV microneutralization assay using TB40 or VR1814 infection of ARPE-19 epithelial cells. Three or four weeks after the third immunization, spleens were extracted from sacrificed mice. Spleen cells were stimulated in vitro with purified protein or a pool of 15-mer peptides (overlapping by 11 amino acids) corresponding to the c-terminal half of the gH protein, stained for cytokine expression, and analyzed using flow cytometry.

Figure 4:
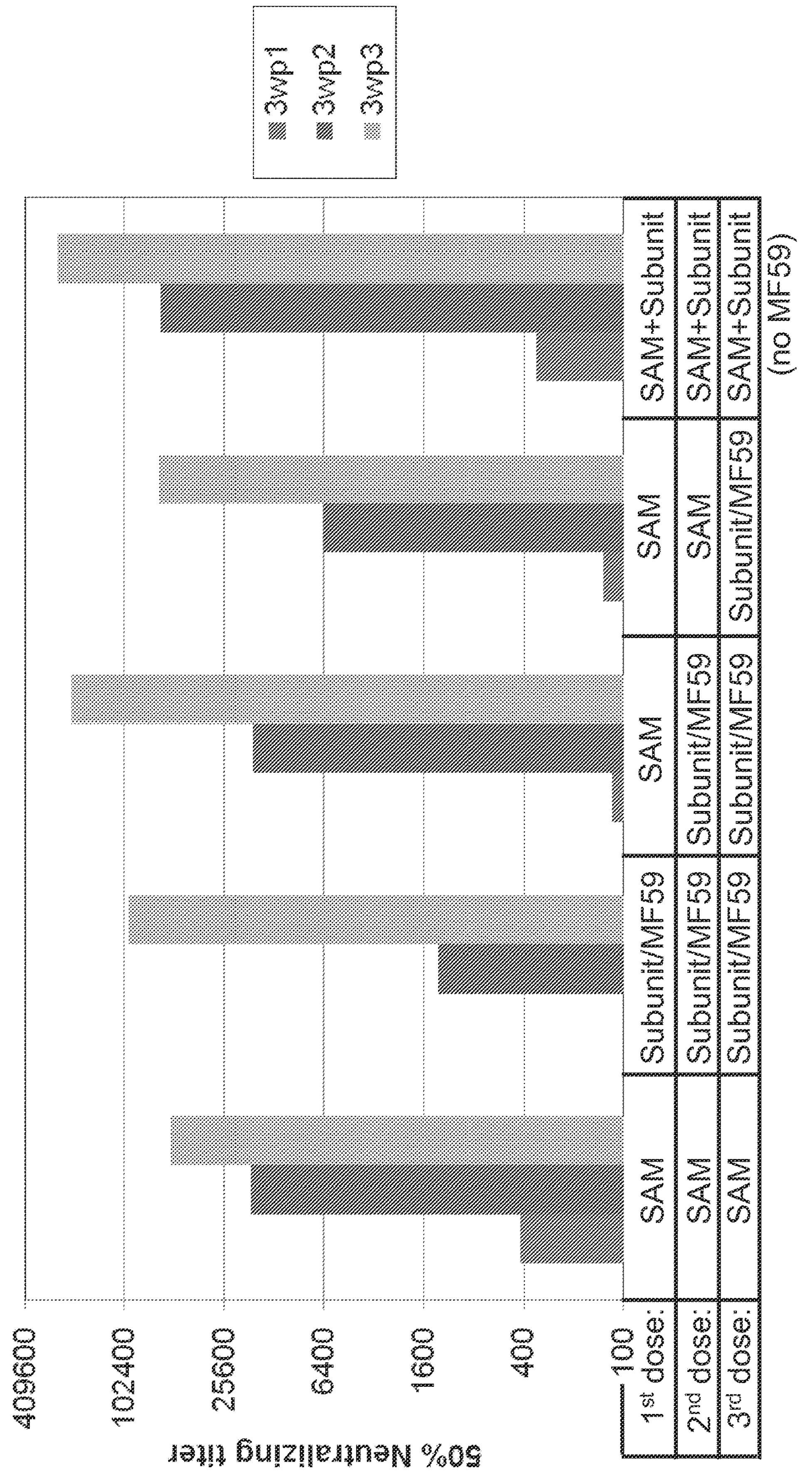
FIG. 4 is a graph showing self amplifying RNA and subunit, alone or in combination, elicit high neutralizing antibody titers. The self amplifying RNA was encapsulated in LNPs. Self amplifying RNA and subunit dose was 1 μg, mixed dose was 1+1 μg. Neutralizing assay: VR1814 infection of ARPE-19 cells in presence of complement.

The SAM vaccine and subunit/MF59 alone elicited potently neutralizing antibody responses after three doses (FIG. 4). The pentameric subunit in MF59 did not respond as well as pentameric SAM vaccine to the first and second dose of vaccine, but titers elicited by subunit/MF59 surpassed titers elicited by SAM vaccine after the third dose. One SAM vaccine prime followed by a single dose of subunit/MF59 elicited stronger neutralizing responses than two doses of subunit/MF59, but was equal to SAM vaccine alone. A second subunit/MF59 boost administered to these animals raised neutralizing responses to a level that exceeded those seen after three doses of subunit/MF59 or SAM vaccine. Two doses of SAM vaccine followed by a single dose of subunit/MF59 did not appear to benefit neutralizing responses compared to either subunit/MF or SAM vaccine alone. Mixing SAM vaccine with subunit, without MF59, elicited a strong response after the first dose, similar to RNA alone, and elicited strong neutralizing titers after two and three doses.

Figure 5:
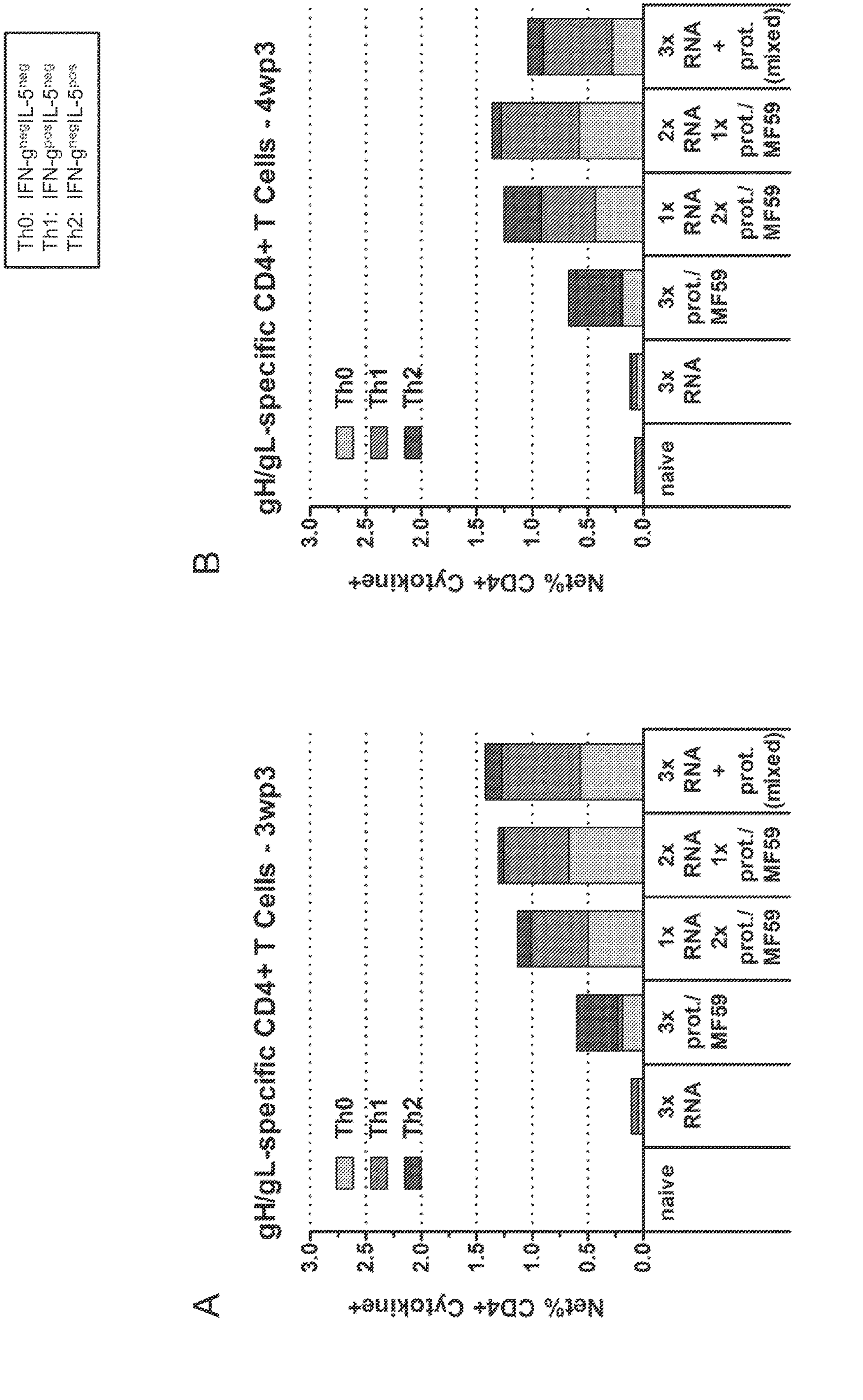
FIGS. 5A and 5B are graphs showing CD4+ T cell responses to the vaccinations using purified gH/gL and pentameric subunits at (A) 3wp3 (day 64) and (B) 4wp3 (day 71).
Figure 6:
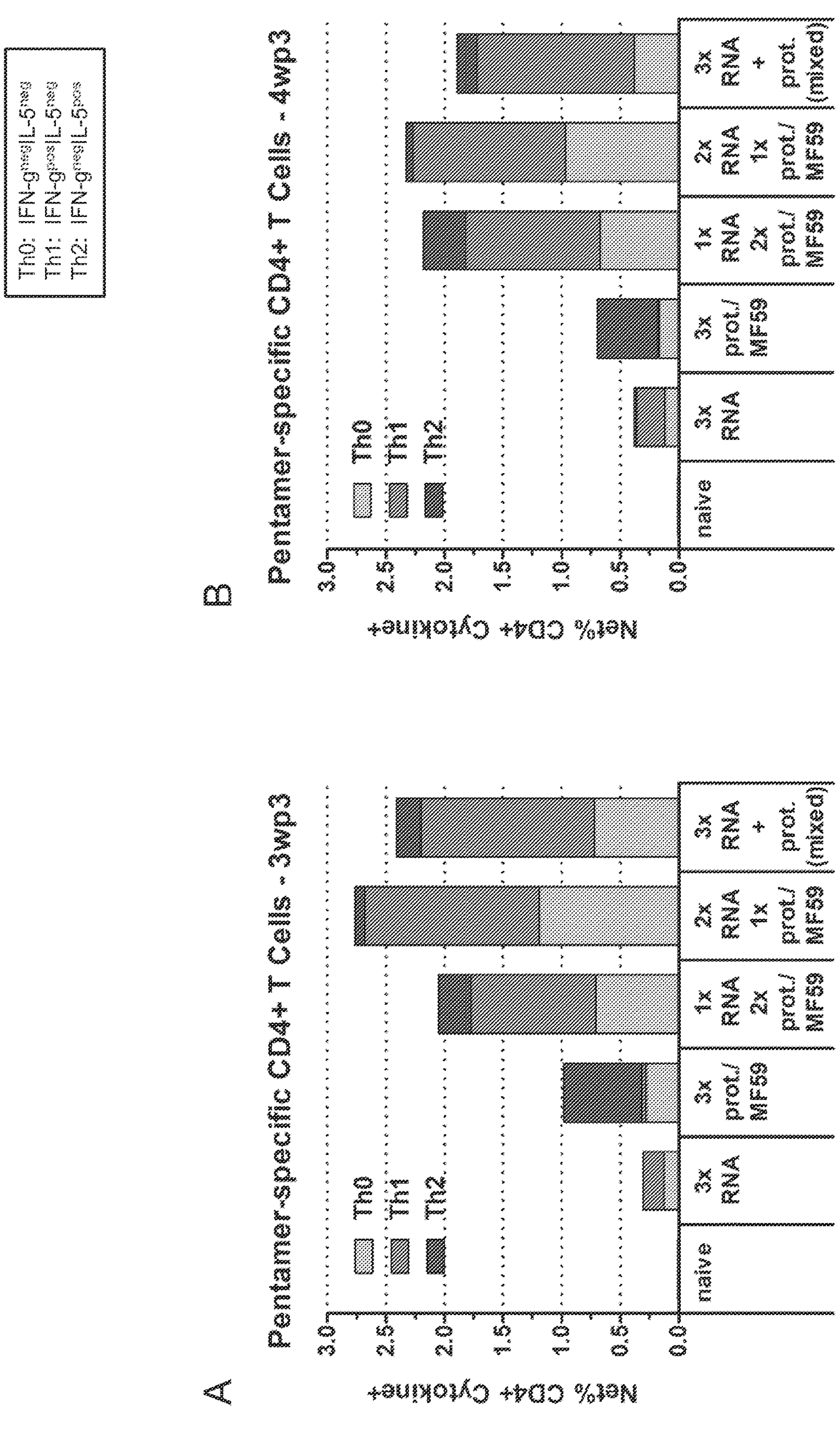
FIGS. 6A and 6B are graphs showing CD4+ T cell responses to the vaccinations using purified pentameric complex at (A) 3wp3 (day 64) and (B) 4wp3 (day 71).

CD4+ T cell responses to the vaccinations using purified gH/gL and pentameric subunits were analyzed. SAM vaccine prime protein boost and mixed SAM vaccine+subunit elicited more CD4+ T cells responding to gH/gL re-stimulation than SAM vaccine or subunit/MF59 alone (FIG. 5). CD4+ responses to RNA alone were insignificant, whereas responses to subunit/MF59 alone were Th2/Th0 phenotype. The phenotype of the responding cells from mice immunized combinations of SAM vaccine and subunit was primarily Th1/Th0. Similar trends were seen when re-stimulating cells with purified pentameric complex, although the responses were generally stronger (FIG. 6).

Figure 7:
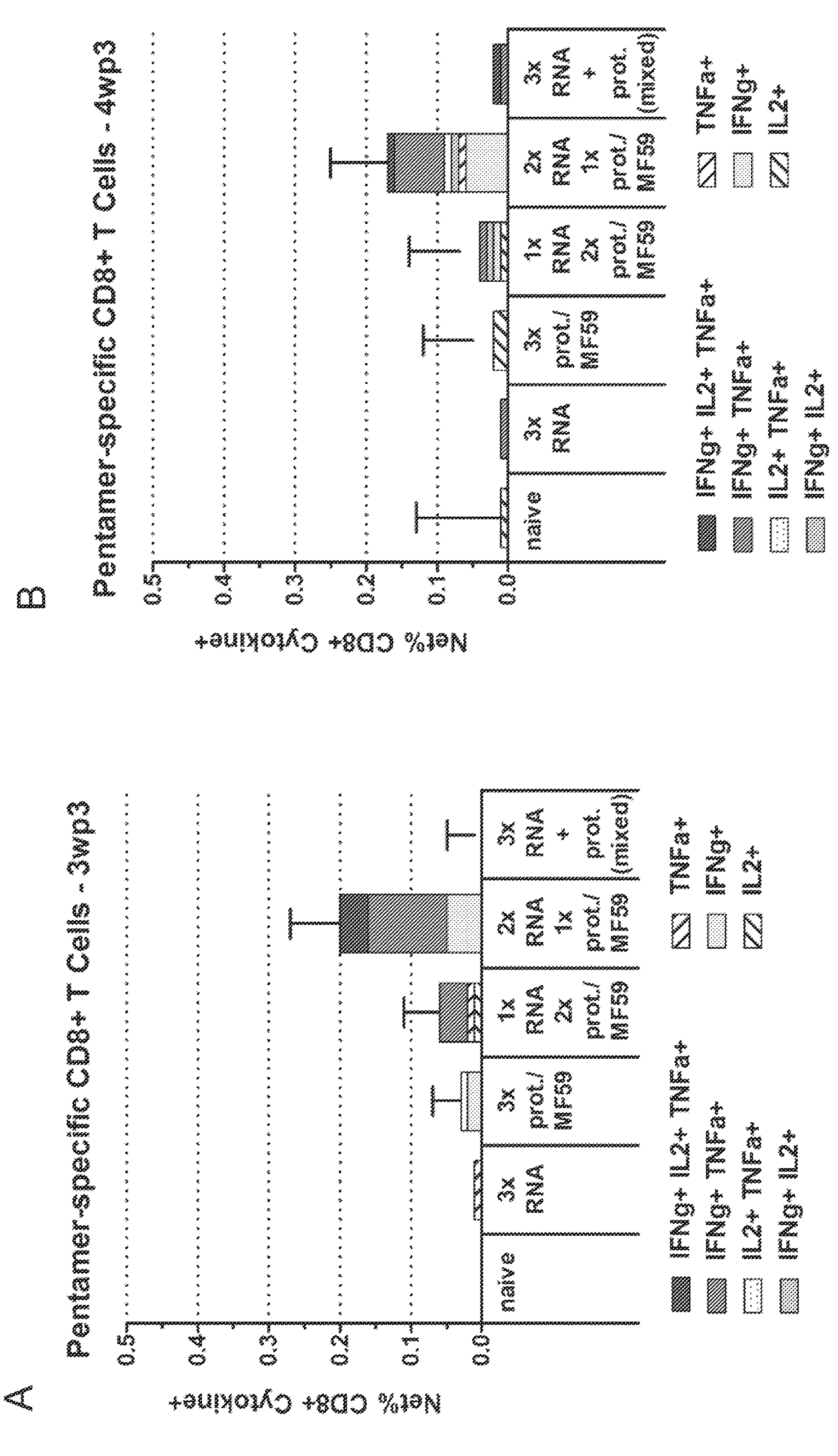
FIGS. 7A and 7B are graphs showing CD8+ T cell responses to the vaccinations using purified pentameric complex at (A) 3wp3 (day 64) and (B) 4wp3 (day 71).
Figure 8:
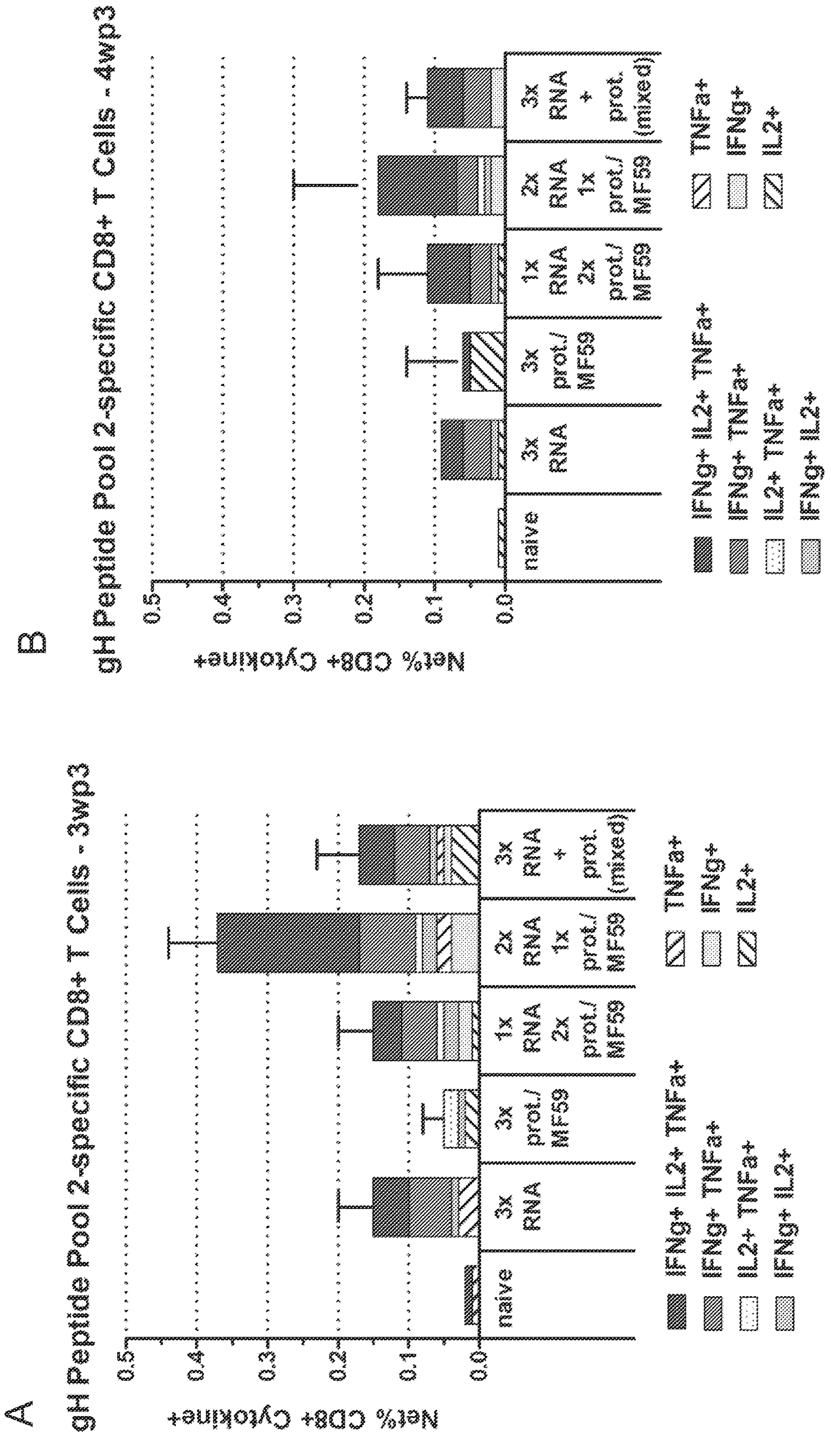
FIGS. 8A and 8B are graphs showing CD8+ T cell responses to the vaccinations using gH peptide pool 2 at (A) 3wp3 (day 64) and (B) 4wp3 (day 71).

CD8+ T cell responses to the vaccinations using purified pentameric subunit or a pool of peptides to gH were also analyzed. The only significant CD8 responses seen when re-stimulating with pentameric subunit was in the mice immunized with two doses of SAM vaccine followed by one dose of subunit/MF59 (FIG. 7). Cells from these animals also showed the strongest responses when re-stimulated with gH peptides (FIG. 8). Mice immunized with the SAM vaccine+subunit, with one dose of SAM vaccine followed by two doses of subunit/MF59, or with SAM vaccine alone, also showed significant responses to re-stimulation (FIG. 8).

Conclusions: One dose of SAM vaccine followed by two doses of subunit/MF59, as well as SAM vaccine+subunit, elicited higher neutralizing titers than subunit/MF59 alone. The response to SAM vaccine+subunit did not require addition of MF59 adjuvant. The largest impact of SAM vaccine prime subunit/MF59 boost was on cellular immune responses. Any combination including the SAM vaccine produced primarily a Th1/Th0 CD4+ response. Moreover, two immunizations with SAM vaccine followed by one immunization with subunit/MF59 produced the strongest CD8+ responses. This study shows that a SAM vaccine prime protein boost regimen can be optimized to produce a desired immune response, i.e. cellular or humoral.

Example VIII

RSV F RNA Prime (Dose Range), Protein Boost (3 μg, Varying Formulation)

RSV-F RNA prime (as a dose range), and a subunit boost (3 μg, different formulations) were administered to mice to evaluate the ability of subunit, with different formulations as indicated in Table VIII-1, to boost RNA-induced response. Each mouse received a constant 3 μg subunit dose, with variable RNA doses and different subunit adjuvants. Mice were vaccinated on days 0, 21 and 42 intramuscularly with a 100 μl dose, split between the two hind legs. Serum was sampled on day 20 for F-specific IgG, and on days 35 and 56 for IgG, IgG1, IgG2a and neutralizing antibody. Spleens were harvested on day 56.

TABLE VIII-1

| Group | n | 1st & 2nd Vacc. | 3rd Vacc. |
|---|---|---|---|
| 1 | 7 | 1 μg RNA/CMF34 | 3 μg F |
| 2 | 7 | 0.01 μg RNA/CMF34 | |
| 3 | 7 | 0.3 ng RNA/CMF34 | |
| 4 | 7 | 3 μg F | |
| 5 | 7 | 1 μg RNA/CMF34 | 3 μg F/alum |
| 6 | 7 | 0.01 μg RNA/CMF34 | |
| 7 | 7 | 0.3 ng RNA/CMF34 | |
| 8 | 7 | 3 μg F/alum | |
| 9 | 7 | 1 μg RNA/CMF34 | 3 μg F/MF59 |
| 10 | 7 | 0.01 μg RNA/CMF34 | |
| 11 | 7 | 0.3 ng RNA/CMF34 | |
| 12 | 7 | 3 μg F/MF59 | |
| 13 | 7 | 1 μg RNA/CMF34 (only 2nd) | 1 μg RNA/CMF34 (T cell ctrl.) |
| 14 | 7 | 0.01 μg RNA/CMF34 (only 2nd) | 0.1 μg RNA/CMF34 (T cell ctrl) |
| 15 | 7 | 0.3 ng RNA/CMF34 (only 2nd) | 0.3 ng RNA/CMF34 (T cell ctrl) |
| 16 | 7 | PBS | PBS |

Figure 9:
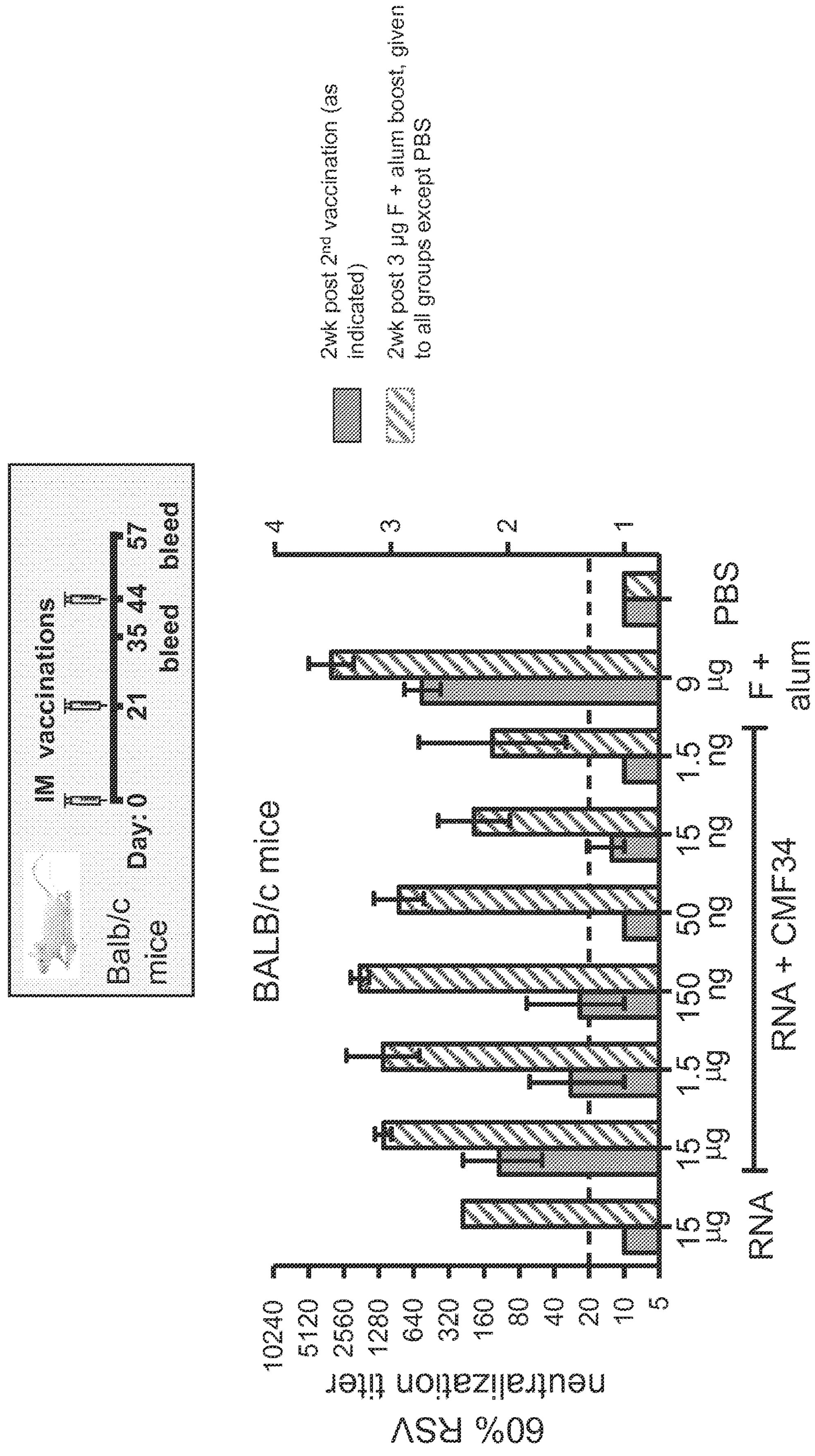
FIG. 9 is a graph showing high neutralizing antibody titers in Balb/c mice that were administered RSV-F-RNA vaccine prime, followed by RSV-F subunit vaccine boost. Mice were administered the vaccine intramuscularly on days 0, 21 and 44, and bleeds were taken on days 35 and 57.
Figure 11A:
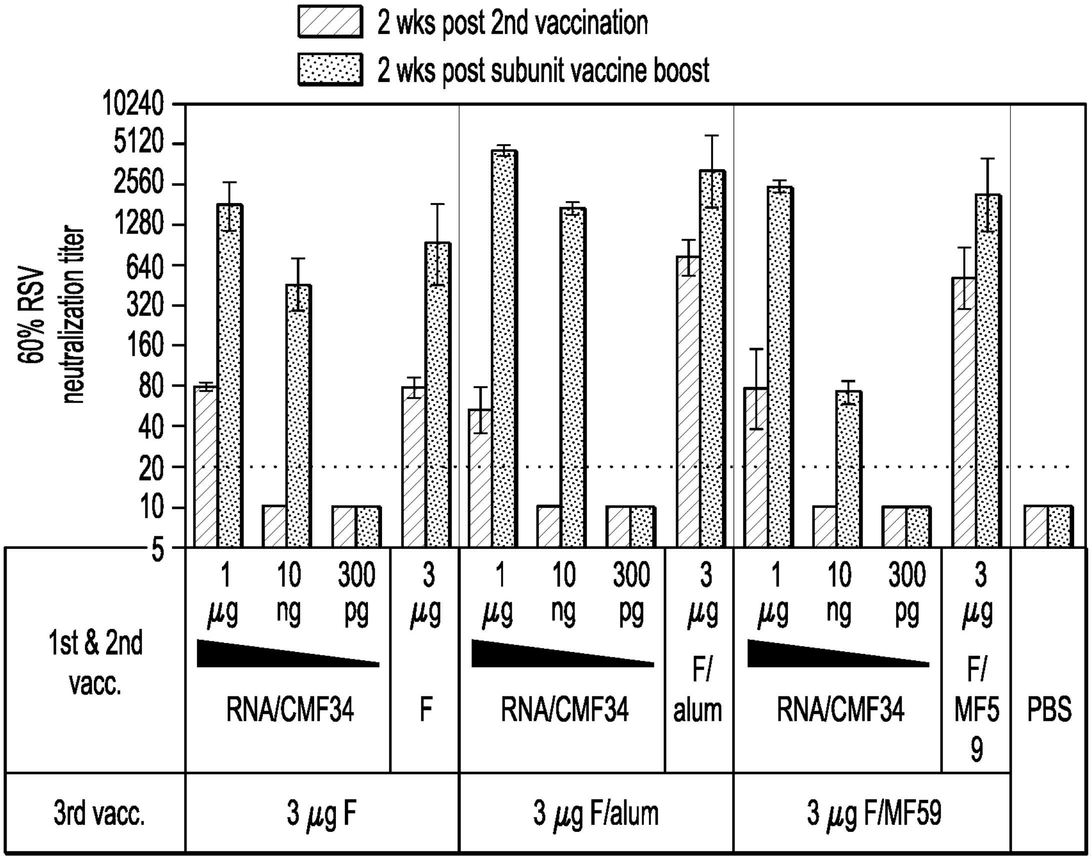
FIGS. 11A-11C are graphs showing the effect of adjuvant on subunit boost. Even though a very low dose of RNA (300 pg) does not induce a measurable RSV-specific antibody response in BALB/c mice (FIG. 11A), it is sufficient to set a Thl-biased phenotype after a subunit vaccine boost (IgG2a-biased, FIG. 11B; IFNy, FIG. 11C; no significant IL-5, FIG. 11C). Subunit vaccine adjuvant (none, alum or MF59) has little impact on the magnitude of the neutralizing antibody titer induced by RNA vaccine prime, subunit vaccine boost.
Figure 11B:
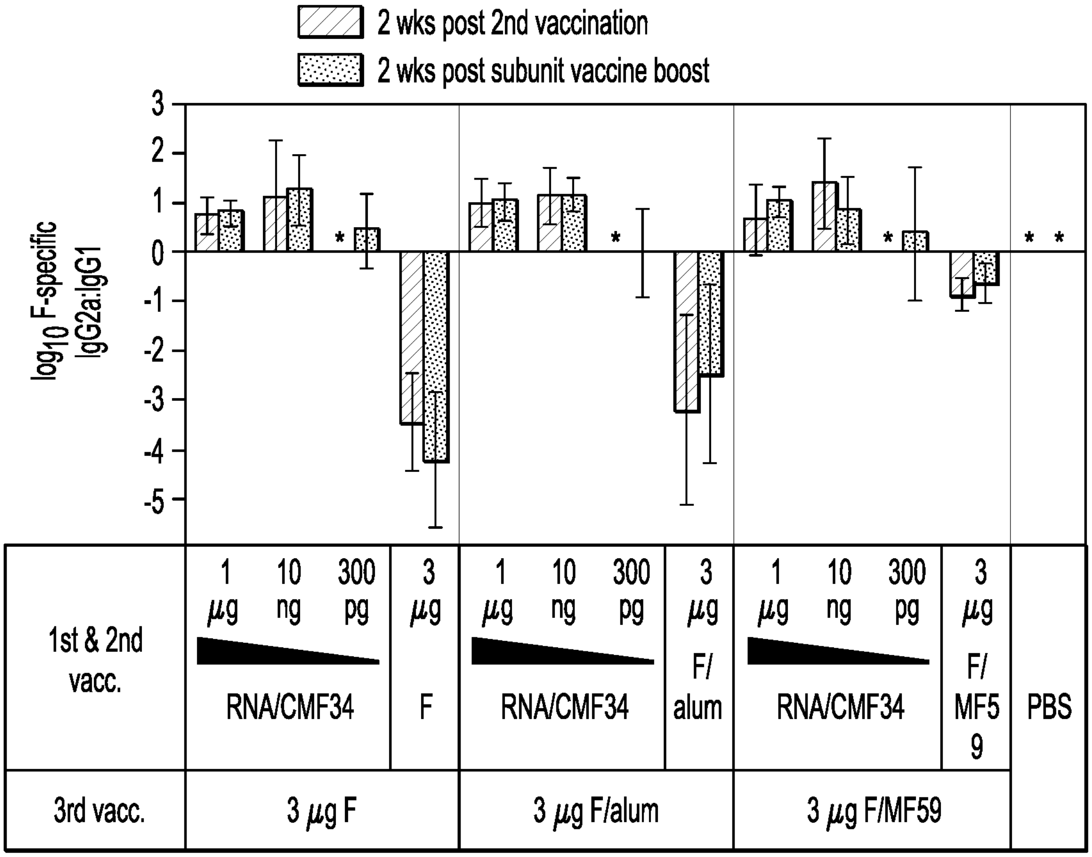
Figure 11C:
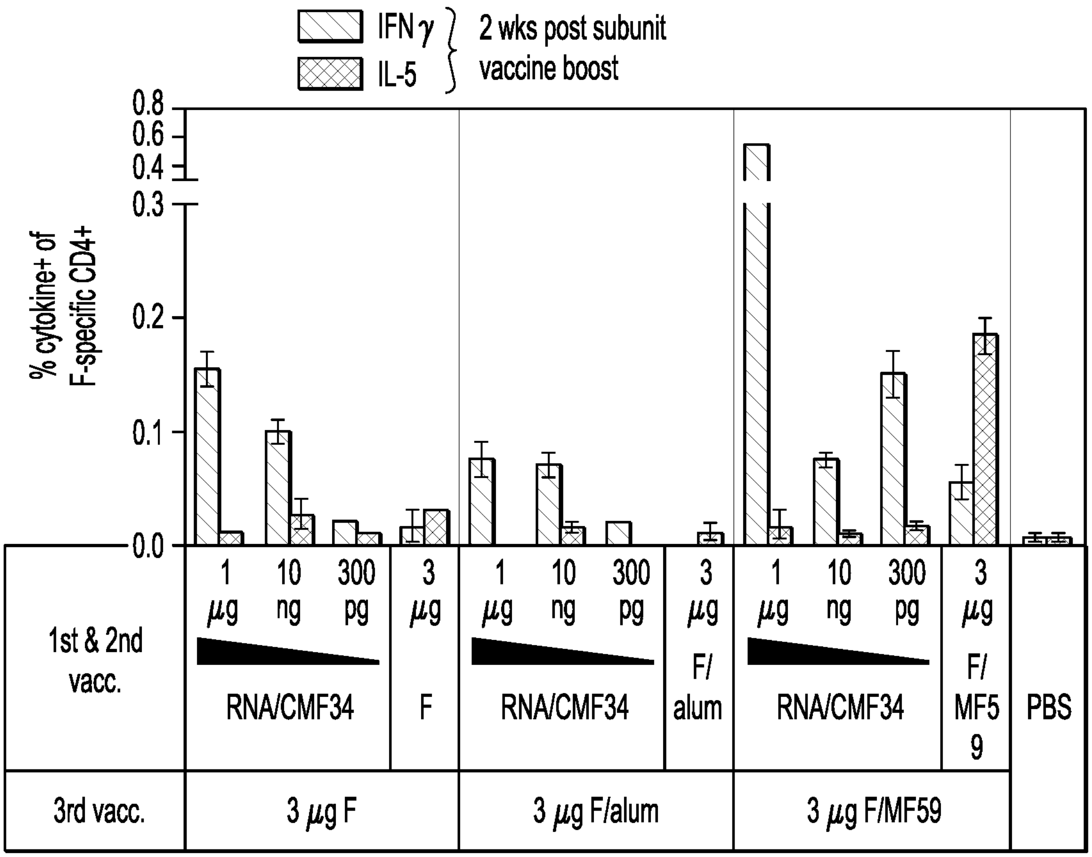

The data showed that RNA prime, subunit boost is an effective regimen for inducing high titer of RSV neutralizing antibodies (FIG. 9). The boost works with alum-adjuvanted, MF59-adjuvanted, or even unadjuvanted F subunit boost (FIG. 11).

Figure 10:
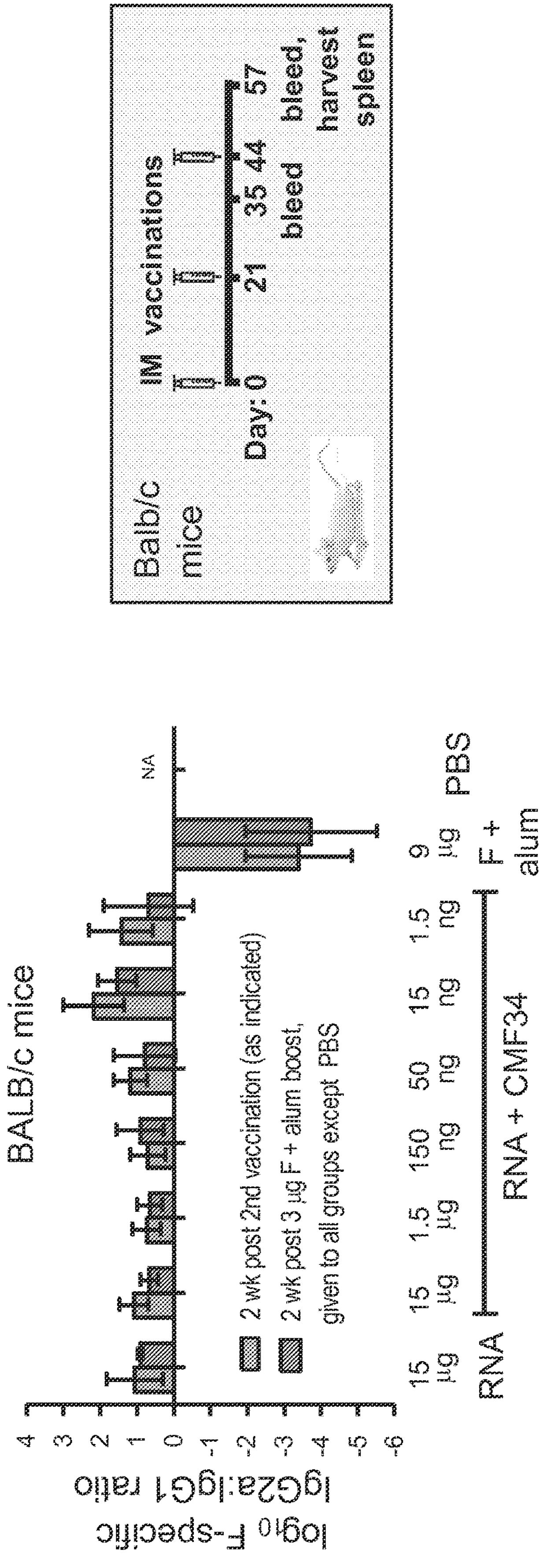
FIG. 10 is a graph showing the F-specific IgG2a:IgG1 ratio in Balb/c mice that were administered the RSV-F-RNA vaccine. The F-RNA vaccine is potent at setting a Th1 immune response, that is maintained after a F subunit vaccine boost. Mice were administered vaccinations intramuscularly on days 0, 21 and 44, and bleeds were taken on days 35 and 57. The spleens of the mice were harvested on day 57.

The RNA vaccine set a Th1-biased response (IgG2a, Th1 cytokines) that was maintained after the subunit boost, irrespective of the boost adjuvant, and even when the subunit with or without adjuvant vaccine induced more of a Th2-biased response on its own (without an RNA prime). Very low doses of the RNA vaccine, even those without a detectable immune response, were sufficient to set the Th1-biased response that was maintained after the subunit boost. (FIG. 10)

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

SEQUENCES

```
CMV gB FL (SEQ ID NO: 1):
1 -

atggaaagccggatctggtgcctggtcgtgtgcgtgaacctgtgcatcgtgtgcctgggagccgccgtgagcagc

agcagcaccagaggcaccagcgccacacacagccaccacagcagccacaccacctctgccgcccacagcagatcc

ggcagcgtgtcccagagagtgaccagcagccagaccgtgtcccacggcgtgaacgagacaatctacaacaccacc

ctgaagtacggcgacgtcgtgggcgtgaataccaccaagtacccctacagagtgtgcagcatggcccagggcacc
```

-continued gacctgatcagattcgagcggaacatcgtgtgcaccagcatgaagcccatcaacgaggacctggacgagggcatc atggtggtgtacaagagaaacatcgtggcccacaccttcaaagtgcgggtgtaccagaaggtgctgaccttccgg cggagctacgcctacatccacaccacatacctgctgggcagcaacaccgagtacgtggcccctcccatgtgggag atccaccacatcaacagccacagccagtgctacagcagctacagccgcgtgatcgccggcacagtgttcgtggcc taccaccgggacagctacgagaacaagaccatgcagctgatgcccgacgactacagcaacacccacagcaccaga tacgtgaccgtgaaggaccagtggcacagcagaggcagcacctggctgtaccgggagacatgcaacctgaactgc atggtcaccatcaccaccgccagaagcaagtacccttaccacttcttcgccacctccaccggcgacgtggtggac atcagccccttctacaacggcaccaaccggaacgccagctacttcggcgagaacgccgacaagttcttcatcttc cccaactacaccatcgtgtccgacttcggcagacccaacagcgctctggaaacccacagactggtggcctttctg gaacgggccgacagcgtgatcagctgggacatccaggacgagaagaacgtgacctgccagctgaccttctgggag gcctctgagagaaccatcagaagcgaggccgaggacagctaccacttcagcagcgccaagatgaccgccaccttc ctgagcaagaaacaggaagtgaacatgagcgactccgccctggactgcgtgagggacgaggccatcaacaagctg cagcagatcttcaacaccagctacaaccagacctacgagaagtatggcaatgtgtccgtgttcgagacaacaggc ggcctggtggtgttctggcagggcatcaagcagaaaagcctggtggagctggaacggctcgccaaccggtccagc ctgaacctgacccacaaccggaccaagcggagcaccgacggcaacaacgcaacccacctgtccaacatggaaagc gtgcacaacctggtgtacgcacagctgcagttcacctacgacaccctgcggggctacatcaacagagccctggcc cagatcgccgaggcttggtgcgtggaccagcggcggaccctggaagtgttcaaagagctgtccaagatcaacccc agcgccatcctgagcgccatctacaacaagcctatcgccgccagattcatgggcgacgtgctgggcctggccagc tgcgtgaccatcaaccagaccagcgtgaaggtgctgcgggacatgaacgtgaaagagagcccaggccgctgctac tccagacccgtggtcatcttcaacttcgccaacagctcctacgtgcagtacggccagctgggcgaggacaacgag atcctgctggggaaccaccggaccgaggaatgccagctgcccagcctgaagatctttatcgccggcaacagcgcc tacgagtatgtggactacctgttcaagcggatgatcgacctgagcagcatctccaccgtggacagcatgatcgcc ctggacatcgacccccctggaaaacaccgacttccgggtgctggaactgtacagccagaaagagctgcggagcagc aacgtgttcgacctggaagagatcatgcgggagttcaacagctacaagcagcgcgtgaaatacgtggaggacaag gtggtggacccccctgcctccttacctgaagggcctggacgacctgatgagcggactgggcgctgccggaaaagcc gtgggagtggccattggagctgtgggcggagctgtggcctctgtcgtggaaggcgtcgccacctttctgaagaac cccttcggcgccttcaccatcatcctggtggccattgccgtcgtgatcatcacctacctgatctacacccggcag cggagactgtgtacccagcccctgcagaacctgttcccctacctggtgtccgccgatggcaccacagtgaccagc ggctccaccaaggataccagcctgcaggccccacccagctacgaagagagcgtgtacaacagcggcagaaagggc cctggccctcccagctctgatgccagcacagccgcccctccctacaccaacgagcaggcctaccagatgctgctg gccctggctagactggatgccgagcagagagggcccagcagaacggcaccgacagcctggatggcagaaccggcacc caggacaagggccagaagcccaacctgctggaccggctgcggcaccggaagaacggctaccggcacctgaaggac agcgacgaggaagagaacgtctgataa - 2727

CMV gB FL (SEQ ID NO: 2)
MESRIWCLVVCVNLCIVCLGAAVSSSSTRGTSATHSHHSSHTTSAAHSRSGSVSQRVTSSQTVSHGVNETIYNTT

LKYGDVVGVNTTKYPYRVCSMAQGTDLIRFERNIVCTSMKPINEDLDEGIMVVYKRNIVAHTFKVRVYQKVLTFR

RSYAYIHTTYLLGSNTEYVAPPMWEIHHINSHSQCYSSYSRVIAGTVFVAYHRDSYENKTMQLMPDDYSNTHSTR

YVTVKDQWHSRGSTWLYRETCNLNCMVTITTARSKYPYHFFATSTGDVVDISPFYNGTNRNASYFGENADKFFIF

PNYTIVSDFGRPNSALETHRLVAFLERADSVISWDIQDEKNVTCQLTFWEASERTIRSEAEDSYHFSSAKMTATF

LSKKQEVNMSDSALDCVRDEAINKLQQIFNTSYNQTYEKYGNVSVFETTGGLVVFWQGIKQKSLVELERLANRSS

LNLTHNRTKRSTDGNNATHLSNMESVHNLVYAQLQFTYDTLRGYINRALAQIAEAWCVDQRRTLEVFKELSKINP

-continued

SAILSAIYNKPIAARFKGDVLGLASCVTINQTSVKVLRDMNVKESPGRCYSRPVVIFNFANSSYVQYGQLGEDNE

ILLGNHRTEECQLPSLKIFIAGNSAYEYVDYLFKRMIDLSSISTVDSMIALDIDPLENTDFRVLELYSQKELRSS

NVFDLEEIMREFNSYKQRVKYVEDKVVDPLPPYLKGLDDLMSGLGAAGKAVGVAIGAVGGAVASVVEGVATFLKN

PFGAFTIILVAIAVVIITYLIYTRQRRLCTQPLQNLFPYLVSADGTTVTSGSTKDTSLQAPPSYEESVYNSGRKG

PGPPSSDASTAAPPYTNEQAYQMLLALARLDAEQRAQQNGTDSLDGRTGTQDKGQKPNLLDRLRHRKNGYRHLKD

SDEEENV--

CMV gB sol 750 (SEQ ID NO: 3):
1- atggaaagccggatctggtgcctggtcgtgtgcgtgaacctgtgcatcgtgtgcctgggagccgccgtgagcagc agcagcaccagaggcaccagcgccacacacagccaccacagcagccacaccacctctgccgcccacagcagatcc ggcagcgtgtcccagagagtgaccagcagccagaccgtgtcccacggcgtgaacgagacaatctacaacaccacc ctgaagtacggcgacgtcgtgggcgtgaataccaccaagtacccctacagagtgtgcagcatggcccagggcacc gacctgatcagattcgagcggaacatcgtgtgcaccagcatgaagcccatcaacgaggacctggacgagggcatc atggtggtgtacaagagaaacatcgtggcccacaccttcaaagtgcgggtgtaccagaaggtgctgaccttccgg cggagctacgcctacatccacaccacatacctgctgggcagcaacaccgagtacgtggcccctcccatgtgggag atccaccacatcaacagccacagccagtgctacagcagctacagccgcgtgatcgccggcacagtgttcgtggcc taccaccgggacagctacgagaacaagaccatgcagctgatgcccgacgactacagcaacacccacagcaccaga tacgtgaccgtgaaggaccagtggcacagcagaggcagcacctggctgtaccgggagacatgcaacctgaactgc atggtcaccatcaccaccgccagaagcaagtacccttaccacttcttcgccacctccaccggcgacgtggtggac atcagccccttctacaacggcaccaaccggaacgccagctacttcggcgagaacgccgacaagttcttcatcttc cccaactacaccatcgtgtccgacttcggcagacccaacagcgctctggaaacccacagactggtggcctttctg gaacgggccgacagcgtgatcagctgggacatccaggacgagaagaacgtgacctgccagctgaccttctgggag gcctctgagagaaccatcagaagcgaggccgaggacagctaccacttcagcagcgccaagatgaccgccaccttc ctgagcaagaaacaggaagtgaacatgagcgactccgccctggactgcgtgagggacgaggccatcaacaagctg cagcagatcttcaacaccagctacaaccagacctacgagaagtatggcaatgtgtccgtgttcgagacaacaggc ggcctggtggtgttctggcagggcatcaagcagaaaagcctggtggagctggaacggctcgccaaccggtccagc ctgaacctgacccacaaccggaccaagcggagcaccgacggcaacaacgcaacccacctgtccaacatggaaagc gtgcacaacctggtgtacgcacagctgcagttcacctacgacaccctgcggggctacatcaacagagccctggcc cagatcgccgaggcttggtgcgtggaccagcggcggaccctggaagtgttcaaagagctgtccaagatcaacccc agcgccatcctgagcgccatctacaacaagcctatcgccgccagattcatgggcgacgtgctgggcctggccagc tgcgtgaccatcaaccagaccagcgtgaaggtgctgcgggacatgaacgtgaaagagagcccaggccgctgctac tccagacccgtggtcatcttcaacttcgccaacagctcctacgtgcagtacggccagctgggcgaggacaacgag atcctgctggggaaccaccggaccgaggaatgccagctgcccagcctgaagatctttatcgccggcaacagcgcc tacgagtatgtggactacctgttcaagcggatgatcgacctgagcagcatctccaccgtggacagcatgatcgcc ctggacatcgacccccctggaaaacaccgacttccgggtgctggaactgtacagccagaaagagctgcggagcagc aacgtgttcgacctggaagagatcatgcgggagttcaacagctacaagcagcgcgtgaaatacgtggaggacaag gtggtggacccccctgcctccttacctgaagggcctggacgacctgatgagcggactgggcgctgccggaaaagcc gtgggagtggccattggagctgtgggcggagctgtggcctctgtcgtggaaggcgtcgccacctttctgaagaac tgataa - 2256

Cmv gB sol 750 (SEQ ID NO: 4)
MESRIWCLVVCVNLCIVCLGAAVSSSSTRGTSATHSHHSSHTTSAAHSRSGSVSQRVTSSQTVSHGVNETIYNTT -continued

LKYGDVVGVNTTKYPYRVCSMAQGTDLIRFERNIVCTSMKPINEDLDEGIMVVYKRNIVAHTFKVRVYQKVLTFR

RSYAYIHTTYLLGSNTEYVAPPMWEIHHINSHSQCYSSYSRVIAGTVFVAYHRDSYENKTMQLMPDDYSNTHSTR

YVTVKDQWHSRGSTWLYRETCNLNCMVTITTARSKYPYHFFATSTGDVVDISPFYNGTNRNASYFGENADKFFIF

PNYTIVSDFGRPNSALETHRLVAFLERADSVISWDIQDEKNVTCQLTFWEASERTIRSEAEDSYHFSSAKMTATF

LSKKQEVNMSDSALDCVRDEAINKLQQIFNTSYNQTYEKYGNVSVFETTGGLVVFWQGIKQKSLVELERLANRSS

SAILSAIYNKPIAARFKGDVLGLASCVTINQTSVKVLRDMNVKESPGRCYSRPVVIFNFANSSYVQYGQLGEDNE

ILLGNHRTEECQLPSLKIFIAGNSAYEYVDYLFKRMIDLSSISTVDSMIALDIDPLENTDFRVLELYSQKELRSS

NVFDLEEIMREFNSYKQRVKYVEDKVVDPLPPYLKGLDDLMSGLGAAGKAVGVAIGAVGGAVASVVEGVATFLKN

--

CMV gB sol 692 (SEQ ID NO: 5):
1- atggaaagccggatctggtgcctggtcgtgtgcgtgaacctgtgcatcgtgtgcctgggagccgccgtgagcagc agcagcaccagaggcaccagcgccacacacagccaccacagcagccacaccacctctgccgcccacagcagatcc ggcagcgtgtcccagagagtgaccagcagccagaccgtgtcccacggcgtgaacgagacaatctacaacaccacc ctgaagtacggcgacgtcgtgggcgtgaataccaccaagtacccctacagagtgtgcagcatggcccagggcacc gacctgatcagattcgagcggaacatcgtgtgcaccagcatgaagcccatcaacgaggacctggacgagggcatc atggtggtgtacaagagaaacatcgtggcccacaccttcaaagtgcgggtgtaccagaaggtgctgaccttccgg cggagctacgcctacatccacaccacatacctgctgggcagcaacaccgagtacgtggcccctcccatgtgggag atccaccacatcaacagccacagccagtgctacagcagctacagccgcgtgatcgccggcacagtgttcgtggcc taccaccgggacagctacgagaacaagaccatgcagctgatgcccgacgactacagcaacacccacagcaccaga tacgtgaccgtgaaggaccagtggcacagcagaggcagcacctggctgtaccgggagacatgcaacctgaactgc atggtcaccatcaccaccgccagaagcaagtacccttaccacttcttcgccacctccaccggcgacgtggtggac atcagccccttctacaacggcaccaaccggaacgccagctacttcggcgagaacgccgacaagttcttcatcttc cccaactacaccatcgtgtccgacttcggcagacccaacagcgctctggaaacccacagactggtggcctttctg gaacgggccgacagcgtgatcagctgggacatccaggacgagaagaacgtgacctgccagctgaccttctgggag gcctctgagagaaccatcagaagcgaggccgaggacagctaccacttcagcagcgccaagatgaccgccaccttc ctgagcaagaaacaggaagtgaacatgagcgactccgccctggactgcgtgagggacgaggccatcaacaagctg cagcagatcttcaacaccagctacaaccagacctacgagaagtatggcaatgtgtccgtgttcgagacaacaggc ggcctggtggtgttctggcagggcatcaagcagaaaagcctggtggagctggaacggctcgccaaccggtccagc ctgaacctgacccacaaccggaccaagcggagcaccgacggcaacaacgcaacccacctgtccaacatggaaagc gtgcacaacctggtgtacgcacagctgcagttcacctacgacaccctgcggggctacatcaacagagccctggcc cagatcgccgaggcttggtgcgtggaccagcggcggaccctggaagtgttcaaagagctgtccaagatcaacccc agcgccatcctgagcgccatctacaacaagcctatcgccgccagattcatgggcgacgtgctgggcctggccagc tgcgtgaccatcaaccagaccagcgtgaaggtgctgcgggacatgaacgtgaaagagagcccaggccgctgctac tccagacccgtggtcatcttcaacttcgccaacagctcctacgtgcagtacggccagctgggcgaggacaacgag atcctgctggggaaccaccggaccgaggaatgccagctgcccagcctgaagatctttatcgccggcaacagcgcc tacgagtatgtggactacctgttcaagcggatgatcgacctgagcagcatctccaccgtggacagcatgatcgcc ctggacatcgacccccctggaaaacaccgacttccgggtgctggaactgtacagccagaaagagctgcggagcagc aacgtgttcgacctggaagagatcatgcgggagttcaacagctacaagcagtgataa - 2082

Cmv gB sol 692 (SEQ ID NO: 6):
MESRIWCLVVCVNLCIVCLGAAVSSSSTRGTSATHSHHSSHTTSAAHSRSGSVSQRVTSSQTVSHGVNETIYNTT

LKYGDVVGVNTTKYPYRVCSMAQGTDLIRFERNIVCTSMKPINEDLDEGIMVVYKRNIVAHTFKVRVYQKVLTFR

-continued

RSYAYIHTTYLLGSNTEYVAPPMWEIHHINSHSQCYSSYSRVIAGTVFVAYHRDSYENKTMQLMPDDYSNTHSTR

YVTVKDQWHSRGSTWLYRETCNLNCMVTITTARSKYPYHFFATSTGDVVDISPFYNGTNRNASYFGENADKFFIF

PNYTIVSDFGRPNSALETHRLVAFLERADSVISWDIQDEKNVTCQLTFWEASERTIRSEAEDSYHFSSAKMTATF

LSKKQEVNMSDSALDCVRDEAINKLQQIFNTSYNQTYEKYGNVSVFETTGGLVVFWQGIKQKSLVELERLANRSS

LNLTHNRTKRSTDGNNATHLSNMESVHNLVYAQLQFTYDTLRGYINRALAQIAEAWCVDQRRTLEVFKELSKINP

SAILSAIYNKPIAARFMGDVLGLASCVTINQTSVKVLRDMNVKESPGRCYSRPVVIFNFANSSYVQYGQLGEDNE

ILLGNHRTEECQLPSLKIFIAGNSAYEYVDYLFKRMIDLSSISTVDSMIALDIDPLENTDFRVLELYSQKELRSS

NVFDLEEIMREFNSYKQ--

CMV gH FL (SEQ ID NO: 7):
1- atgaggcctggcctgccctcctacctgatcatcctggccgtgtgcctgttcagccacctgctgtccagcagatac ggcgccgaggccgtgagcgagcccctggacaaggctttccacctgctgctgaacacctacggcagacccatccgg tttctgcgggagaacaccacccagtgcacctacaacagcagcctgcggaacagcaccgtcgtgagagagaacgcc atcagcttcaactttttccagagctacaaccagtactacgtgttccacatgcccagatgcctgtttgccggccct ctggccgagcagttcctgaaccaggtggacctgaccgagacactggaaagataccagcagcggctgaatacctac gccctggtgtccaaggacctggccagctaccggtcctttagccagcagctcaaggctcaggatagcctcggcgag cagcctaccaccgtgcccccctcccatcgacctgagcatcccccacgtgtggatgcctccccagaccacccctcac ggctggaccgagagccacaccacctccggcctgcacagaccccacttcaaccagacctgcatcctgttcgacggc cacgacctgctgtttagcaccgtgacccccctgcctgcaccagggcttctacctgatcgacgagctgagatacgtg aagatcaccctgaccgaggatttcttcgtggtcaccgtgtccatcgacgacgacacccccatgctgctgatcttc ggccacctgcccagagtgctgttcaaggcccccctaccagcgggacaacttcatcctgcggcagaccgagaagcac gagctgctggtgctggtcaagaaggaccagctgaaccggcactcctacctgaaggaccccgacttcctggacgcc gccctggacttcaactacctggacctgagcgccctgctgagaaacagcttccacagatacgccgtggacgtgctg aagtccggacggtgccagatgctcgatcggcggaccgtggagatggccttcgcctatgccctcgccctgttcgcc gctgccagacaggaagaggctggcgcccaggtgtcagtgcccagagccctggatagacaggccgccctgctgcag atccaggaattcatgatcacctgcctgagccagacccccccctagaaccaccctgctgctgtaccccacagccgtg gatctggccaagagggccctgtggacccccaaccagatcaccgacatcacaagcctcgtgcggctcgtgtacatc ctgagcaagcagaaccagcagcacctgatcccccagtgggccctgagacagatcgccgacttcgccctgaagctg cacaagacccatctggccagctttctgagcgccttcgccaggcaggaactgtacctgatgggcagcctggtccac agcatgctggtgcataccaccgagcggcgggagatcttcatcgtggagacaggcctgtgtagcctggccgagctg tcccactttacccagctgctggcccaccctcaccacgagtacctgagcgacctgtacaccccctgcagcagcagc ggcagacgggaccacagcctggaacggctgaccagactgttccccgatgccaccgtgcctgctacagtgcctgcc gccctgtccatcctgtccaccatgcagcccagcaccctggaaaccttccccgacctgttctgcctgcccctgggc gagagctttagcgccctgaccgtgtccgagcacgtgtcctacatcgtgaccaatcagtacctgatcaagggcatc agctaccccgtgtccaccacagtcgtgggccagagcctgatcatcacccagaccgacagccagaccaagtgcgag ctgacccggaacatgcacaccacacacagcatcaccgtggccctgaacatcagcctggaaaactgcgctttctgt cagtctgccctgctggaatacgacgatacccagggcgtgatcaacatcatgtacatgcacgacagcgacgacgtg ctgttcgccctggacccctacaacgaggtggtggtgtccagcccccggacccactacctgatgctgctgaagaac ggcaccgtgctggaagtgaccgacgtggtggtggacgccaccgacagcagactgctgatgatgagcgtgtacgcc ctgagcgccatcatcggcatctacctgctgtaccggatgctgaaaaacctgctgataa - 2232

CMV gH FL (SEQ ID NO: 8);

-continued

MRPGLPSYLIILAVCLFSHLLSSRYGAEAVSEPLDKAFHLLLNTYGRPIRFLRENTTQCTYNSSLRNSTVVRENA

ISFNFFQSYNQYYVFHMPRCLFAGPLAEQFLNQTQLTETLERYQQRLNTYALVSKDLASYRSFSQQLKAQDSLCE

QPTTVPPPIDLSIPHVWMPPQTTPHGWTESHTTSGLHRPHFNQTCILFDGHDLLFSTVTPCLHQGFYLIDELRYV

KITLTEDFFVVTVSIDDDTPMLLIFGHLPRVLFKAPYQRDNFILRQTEKHELLVLVKKDQLNRHSYLKDPDFLDA

ALDFNYLDLSALLRNSFHRYAVDVLKSGRCQMLDRRTVEMAFAYALALFAAARQEEAGAQVSVPRALDRQAALLQ

IQEFMITCLSQTPPRTTLLLYPTAVDLAKRALWTPNQITDITSLVRLVYILSKQNQQHLIPQWALRQIADFALKL

HKTHIASFLSAFARQELYU4GSLVHSMLVHTTERREIFIVETGLCSLAELSHFTQLLAHPHHEYLSDLYTPCSSS

GRRDHSLERLTRLFPDATVPATVPAALSILSTMQPSTLETFPDLFCLPLGESFSALTVSEHVSYIVTNQYLIKGI

SYPVSTTVVGQSLIITQTDSQTKCELTRNMHTTHSITVALNISLENCAFCQSALLEYDDTQGVINIMYMHDSDDV

LFALDPYNEVVVSSPRTHYLMLLKNGTVLEVTDVVVDATDSRLLMMSVYALSAIIGIYLLYRMLKTC--

CMV gH sol (SEQ ID NO: 9):
1- atgaggcctggcctgccctcctacctgatcatcctggccgtgtgcctgttcagccacctgctgtccagcagatac ggcgccgaggccgtgagcgagcccctggacaaggctttccacctgctgctgaacacctacggcagacccatccgg tttctgcgggagaacaccacccagtgcacctacaacagcagcctgcggaacagcaccgtcgtgagagagaacgcc atcagcttcaactttttccagagctacaaccagtactacgtgttccacatgcccagatgcctgtttgccggccct ctggccgagcagttcctgaaccaggtggacctgaccgagacactggaaagataccagcagcggctgaatacctac gccctggtgtccaaggacctggccagctaccggtcctttagccagcagctcaaggctcaggatagcctcggcgag cagcctaccaccgtgccccctcccatcgacctgagcatcccccacgtgtggatgcctccccagaccacccctcac ggctggaccgagagccacaccacctccggcctgcacagaccccacttcaaccagacctgcatcctgttcgacggc cacgacctgctgtttagcaccgtgacccccctgcctgcaccagggcttctacctgatcgacgagctgagatacgtg aagatcaccctgaccgaggatttcttcgtggtcaccgtgtccatcgacgacgacacccccatgctgctgatcttc ggccacctgcccagagtgctgtccaaggcccccctaccagcgggacaacttcatcctgcggcagaccgagaagcac gagctgctggtgctggtcaagaaggaccagctgaaccggcactcctacctgaaggaccccgacttcctggacgcc gccctggacttcaactacctggacctgagcgccctgctgagaaacagcttccacagatacgccgtggacgtgctg aagtccggacggtgccagatgctcgatcggcggaccgtggagatggccttcgcctatgccctcgccctgttcgcc gctgccagacaggaagaggctggcgcccaggtgtcagtgcccagagccctggatagacaggccgccctgctgcag atccaggaattcatgatcacctgcctgagccagacccccccctagaaccaccctgctgctgtaccccacagccgtg gatctggccaagagggccctgtggacccccaaccagatcaccgacatcacaagcctcgtgcggctcgtgtacatc ctgagcaagcagaaccagcagcacctgatcccccagtgggccctgagacagatcgccgacttcgccctgaagctg cacaagacccatctggccagctttctgagcgccttcgccaggcaggaactgtacctgatgggcagcctggtccac agcatgctggtgcataccaccgagcggcgggagatcttcatcgtggagacaggcctgtgtagcctggccgagctg tcccactttacccagctgctggcccaccctcaccacgagtacctgagcgacctgcacacccccctgcagcagcagc ggcagacgggaccacagcctggaacggctgaccagactgttccccgatgccaccgtgcctgctacagtgcctgcc gccctgtccatcctgtccaccatgcagcccagcaccctggaaaccttccccgacctgttctgcctgcccctgggc gagagctttagcgccctgaccgtgtccgagcacgtgtcctacatcgtgaccaatcagtacctgatcaagggcatc agctaccccgtgtccaccacagtcgtgggccagagcctgatcatcacccagaccgacagccagaccaagtgcgag ctgacccggaacatgcacaccacacacagcatcaccgtggccctgaacatcagcctggaaaactgcgctttctgt cagtctgccctgctggaatacgacgatacccagggcgtgatcaacatcatgtacatgcacgacagcgacgacgtg ctgttcgccctggacccctacaacgaggtggtggtgtccagcccccggacccactacctgatgctgctgaagaac ggcaccgtgctggaagtgaccgacgtggtggtggacgccaccgactgataa - 2151

-continued

CMV gH sol (SEQ ID NO: 10):
MRPGLPSYLIILAVCLFSHLLSSRYGAEAVSEPLDKAFHLLLNTYGRPIRFLRENTTQCTYN

SSLRNSTVVRENATSFNFFQSYNQYYVFHMPRCLFAGPLAEQFLNQVDLTETLERYQQRLNT

YALVSKDLASYRSFSQQLKAQDSLGEQPTTVPPPIDLSIPHVWMPPQTTPHGWTESHTTSGL

HRPHFNQTCILFDGHDLLFSTVTPCLHQGFYLIDELRYVKITLTEDFFVVTVSIDDDTPMLL

IFGHLPRVLFKAPYQRDNFILRQTEKHELLVLVKKDQLNRHSYLKDPDFLDAALDFNYLDLS

ALLRNSFHRYAVDVLKSGRCQMLDRRTVEMAFAYALALFAAARQEEAGAQVSVPRALDRQAA

LLQIQEFMITCLSQTPPRTTLLLYPTAVDLAKRALWTPNQITDITSLVRLVYILSKQNQQHL

IPQWALRQIADFALKLHKTHLASFLSAFARQELYLMGSLVHSMLVHTTERREIFIVETGLCS

LAELSHFTQLLAHPHHEYLSDLYTPCSSSGRRDHSLERLTRLFPDATVPATVPAALSILSTM

QPSTLETFPDLFCLPLGESFSALTVSEHVSYIVTNQYLIKGISYPVSTTVVGQSLIITQTDS

QTKCELTRNMHTTHSITVALNISLENCAFCQSALLEYDDTQGVINIMYMHDSDDVLFALDPY

NEVVVSSPRTHYLHLLKNGTVLEVTDVVVDATD--

CMV gL fl (SEQ ID NO: 11:
1- atgtgcagaaggcccgactgcggcttcagcttcagccctggacccgtgatcctgctgtggtgctgcctgctgctg cctatcgtgtcctctgccgccgtgtctgtggcccctacagccgccgagaaggtgccagccgagtgccccgagctg accagaagatgcctgctgggcgaggtgttcgagggcgacaagtacgagagctggctgcggcccctggtcaacgtg accggcagagatggcccccctgagccagctgatccggtacagacccgtgacccccgaggccgccaatagcgtgctg ctggacgaggccttcctggataccctggccctgctgtacaacaaccccgaccagctgagagccctgctgaccctg ctgtccagcgacaccgcccccagatggatgaccgtgatgcggggctacagcgagtgtggagatggcagccctgcc gtgtacacctgcgtggacgacctgtgcagaggctacgacctgaccagactgagctacggccggtccatcttcaca gagcacgtgctgggcttcgagctggtgccccccagcctgttcaacgtggtggtggccatccggaacgaggccacc agaaccaacagagccgtgcggctgcctgtgtctacagccgctgcacctgagggcatcacactgttctacggcctg tacaacgccgtgaaagagttctgcctccggcaccagctggatccccccctgctgagacacctggacaagtactac gccggcctgcccccagagctgaagcagaccagagtgaacctgcccgcccacagcagatatggccctcaggccgtg gacgccagatgataa - 840

CMV gL FL (SEQ ID NO: 12):
MCRRPDCGFSFSPGPVILLWCCLLLPIVSSAAVSVAPTAAEKVPAECPELTRRCLLGEVFEGDKYESMLRPLVNV

TGRDGPLSQLIRYRPVTPEAANSVLLDEAFLDTLALLYNNPDQLRALLTLLSSDTAPRWMTVMRGYSECGDGSPA

VYTCVDDLCRGYDLTRLSYGRSIFTEHVLGFELVPPSLFNVVVAIRNEATRTNRAVRLPVSTAAAPEGITLFYGL

YNAVKEFCLRHQLDPPLLRHLDKYYAGLPPELKQTRVNLPAHSRYGPQAVDAR--

CMV gM FL (SEQ ID NO: 13):
1- atggcccccagccacgtggacaaagtgaacacccggacttggagcgccagcatcgtgttcatggtgctgaccttc gtgaacgtgtccgtgcacctggtgctgtccaacttcccccacctgggctacccctgcgtgtactaccacgtggtg gacttcgagcggctgaacatgagcgcctacaacgtgatgcacctgcacacccccatgctgtttctggacagcgtg cagctcgtgtgctacgccgtgttcatgcagctggtgtttctggccgtgaccatctactacctcgtgtgctggatc aagatcagcatgcggaaggacaagggcatgagcctgaaccagagcacccgggacatcagctacatgggcgacagc ctgaccgccttcctgttcatcctgagcatggacaccttccagctgttcaccctgaccatgagcttccggctgccc agcatgatcgccttcatggccgccgtgcactttttctgtctgaccatcttcaacgtgtccatggtcacccagtac cggtcctacaagcggagcctgttcttcttctcccggctgcaccccaagctgaagggcaccgtgcagttccggacc ctgatcgtgaacctggtggaggtggccctgggcttcaataccaccgtggtggctatggccctgtgctacggcttc -continued ggcaacaacttcttcgtgcggaccggccatatggtgctggccgtgttcgtggtgtacgccatcatcagcatcatc tactttctgctgatcgaggccgtgttcttccagtacgtgaaggtgcagttcggctaccatctgggcgcctttttc ggcctgtgcggcctgatctaccccatcgtgcagtacgacaccttcctgagcaacgagtaccggaccggcatcagc tggtccttcggaatgctgttcttcatctgggccatgttcaccacctgcagagccgtgcggtacttcagaggcaga ggcagcggctccgtgaagtaccaggccctggccacagcctctggcgaagaggtggccgccctgagccaccacgac agcctggaaagcagacggctgcgggaggaagaggacgacgacgacgaggacttcgaggacgcctgataa -

1119

CMV gM FL (SEQ ID NO: 14):
MAPSHVDKVNTRTWSASIVFMVLTFVNVSVHLVLSNFPHLGYPCVYYHVVDFERLNMSAYNV

MHLHTPMLFLDSVQLVCYAVFMQLVFLAVTIYYLVCWIKISMRKDKGMSLNQSTRDISYMGD

SLTAFLFILSMDTFQLFTLTMSFRLPSMIAFMAAVHFFCLTIFNVSMVTQYRSYKRSLFFFS

RLHPKLKGTVQFRTLIVNLVEVALGFNTTVVAMALCYGFGNNFFVRTGHMVLAVFVVYAIIS

IIYFLLIEAVFFQYVKVQFGYHLGAFFGLCGLIYPIVQYDTFLSNEYRTGISWSFGMLFFIW

AMFTTCRAVRYFRGRGSGSVKYQALATASGEEVAALSHHDSLESRRLREEEDDDDEDFEDA-

CMV gN FL (SEQ ID NO: 15):
1- atggaatggaacaccctggtcctgggcctgctggtgctgtctgtcgtggccagcagcaacaacacatccacagcc agcacccctagacctagcagcagcacccacgccagcactaccgtgaaggctaccaccgtggccaccacaagcacc accactgctaccagcaccagctccaccacctctgccaagcctggctctaccacacacgaccccaacgtgatgagg ccccacgcccacaacgacttctacaacgctcactgcaccagccacatgcacgagctgtccctgagcagctttgcc gcctggtggaccatgctgaacgccctgatcctgatgggcgccttctgcatcgtgctgcggcactgctgcttccag aacttcaccgccaccaccaccaagggctactgataa - 411

CMV gN FL (SEQ ID NO: 16):
MEWNTLVLGLLVLSVVASSNNTSTASTPRPSSSTHASTTVKATTVATTSTTTATSTSSTTSAKPGSTTHDPNVMR

PHAHNDFYNAHCTSHMYELSLSSFAAWWTMLNALILMGAFCIVLRHCCFQNFTATTTKGY--

CMV gO FL (SEQ ID NO: 17):
1- atgggcaagaaagaaatgatcatggtcaagggcatccccaagatcatgctgctgattagcatcacctttctgctg ctgtccctgatcaactgcaacgtgctggtcaacagccggggcaccagaagatcctggccctacaccgtgctgtcc taccggggcaaagagatcctgaagaagcagaaagaggacatcctgaagcggctgatgagcaccagcagcgacggc taccggttcctgatgtaccccagccagcagaaattccacgccatcgtgatcagcatggacaagttcccccaggac tacatcctggccggacccatccggaacgacagcatcacccacatgtggttcgacttctacagcacccagctgcgg aagcccgccaaatacgtgtacagcgagtacaaccacaccgcccacaagatcaccctgaggcctcccccttgtggc accgtgcccagcatgaactgcctgagcgagatgctgaacgtgtccaagcggaacgacaccggcgagaagggctgc ggcaacttcaccaccttcaaccccatgttcttcaacgtgccccggtggaacaccaagctgtacatcggcagcaac aaagtgaacgtggacagccagaccatctactttctgggcctgaccgccctgctgctgagatacgcccagcggaac tgcacccggtccttctacctggtcaacgccatgagccggaacctgttccgggtgcccaagtacatcaacggcacc aagctgaagaacaccatgcggaagctgaagcggaagcaggccctggtcaaagagcagccccagaagaagaacaag aagtcccagagcaccaccacccccctacctgagctacaccacctccaccgccttcaacgtgaccaccaacgtgacc tacagcgccacagccgccgtgaccagagtggccacaagcaccaccggctaccggcccgacagcaactttatgaag tccatcatggccacccagctgagagatctggccacctgggtgtacaccaccctgcggtacagaaacgagcccttc tgcaagcccgaccggaacagaaccgccgtgagcgagttcatgaagaatacccacgtgctgatcagaaacgagaca -continued ccctacaccatctacggcaccctggacatgagcagcctgtactacaacgagacaatgagcgtggagaacgagaca gccagcgacaacaacgaaaccacccccacctcccccagcacccggttccagcggaccttcatcgacccccctgtgg gactacctggacagcctgctgttcctggacaagatccggaacttcagcctgcagctgcccgcctacggcaatctg accccccctgagcacagaagggccgccaacctgagcaccctgaacagcctgtggtggtggagccagtgataa -

1422

CMV gO FL (SEQ ID NO: 18):
MGKKEMIMVKGTPKIMLLISITFLLLSLINCNVLVNSRGTRRSWPYTVLSYRGKEILKKQKE

DILKRLMSTSSDGYRFLMYPSQQKFHAIVISMDKFPQDYILAGPIRNDSITHMWFDFYSTQL

RKPAKYVYSEYNHTAHKITLRPPPCGTVPSMNCLSEMLNVSKRNDTGEKGCGNFTTFNPMFF

NVPRWNTKLYIGSNKVNVDSQTIYFLGLTALLLRYAQRNCTRSFYLVNAMSRNLFRVPKYIN

GTKLKNTMRKLKRKQALVKEQPQKKNKKSQSTTTPYLSYTTSTAFNVTTNVTYSATAAVTRV

ATSTTGYRPDSNFMKSIMATQLRDLATWVYTTLRYRNEPFCKPDRNRTAVSEFMKNTHVLIR

NETPYTIYGTLDMSSLYYNETMSVENETASDNNETTPTSPSTRFQRTFIDPLWDYLDSLLFL

DKIRNFSLQLPAYGNLTPPEHRRAANLSTLNSLWWWSQ--

CMV UL128 FL (SEQ ID NO: 19):
1- atgagccccaaggacctgacccccttcctgacaaccctgtggctgctcctgggccatagcagagtgcctagagtg cgggccgaggaatgctgcgagttcatcaacgtgaaccacccccccgagcggtgctacgacttcaagatgtgcaac cggttcaccgtggccctgagatgccccgacggcgaagtgtgctacagccccgagaaaaccgccgagatccggggc atcgtgaccaccatgacccacagcctgacccggcaggtggtgcacaacaagctgaccagctgcaactacaacccc ctgtacctggaagccgacggccggatcagatgcggcaaagtgaacgacaaggcccagtacctgctgggagccgcc ggaagcgtgccctaccggtggatcaacctggaatacgacaagatcacccggatcgtgggcctggaccagtacctg gaaagcgtgaagaagcacaagcggctggacgtgtgcagagccaagatgggctacatgctgcagtgataa - 519

CMV UL128 FL (SEQ ID NO: 20):
MSPKDLTPFLTTLWLLLGHSRVPRVRAEECCEFINVNHPPERCYDFKMCNRFTVALRCPDGEVCYSPEKTAEIRG

IVTTMTHSLTRQVVHNKLTSCNYNPLYLEADGRIRCGKVNDKAQYLLGAAGSVPYRWINLEYDKITRIVGLDQYL

ESVKKHKRLDVCRAKMGYMLQ--

CMV UL130 FL (SEQ ID NO: 21):
1- atgctgcggctgctgctgagacaccacttccactgcctgctgctgtgtgccgtgtgggccacccccttgtctggcc agcccttggagcaccctgaccgccaaccagaaccctagcccccccttggtccaagctgacctacagcaagccccac gacgccgccaccttctactgccccttttctgtaccccagccctcccagaagccccctgcagttcagcggcttccag agagtgtccaccggccctgagtgccggaacgagacactgtacctgctgtacaaccgggagggccagacactggtg gagcggagcagcacctgggtgaaaaaagtgatctggtatctgagcggccggaaccagaccatcctgcagcggatg cccagaaccgccagcaagcccagcgacggcaacgtgcagatcagcgtggaggacgccaaaatcttcggcgcccac atggtgcccaagcagaccaagctgctgagattcgtggtcaacgacggcaccagatatcagatgtgcgtgatgaag ctggaaagctgggcccacgtgttccgggactactccgtgagcttccaggtccggctgaccttcaccgaggccaac aaccagacctacaccttctgcacccaccccaacctgatcgtgtgataa - 648

CMV UL130 FL (SEQ ID NO: 22):
MLRLLLRHHFHCLLLCAVWATPCLASPWSTLTANQNPSPPWSKLTYSKPHDAATFYCPFLYP

SPPRSPLQFSGFQRVSTGPECRNETLYLLYNREGQTLVERSSTWVKKVIWYLSGRNQTILQR

MPRTASKPSDGNVQISVEDAKIFGAHMVPKQTKLLRFVVNDGTRYQMCVMKLESWAHVFRDY

SVSFQVRLTFTEANNQTYTFCTHPNLIV--

-continued

CMV UL131 FL (SEQ ID NO: 23):
1- atgcggctgtgcagagtgtggctgtccgtgtgcctgtgtgccgtggtgctgggccagtgccagagagagacagcc gagaagaacgactactaccgggtgccccactactgggatgcctgcagcagagccctgcccgaccagacccggtac aaatacgtggagcagctcgtggacctgaccctgaactaccactacgacgccagccacggcctggacaacttcgac gtgctgaagcggatcaacgtgaccgaggtgtccctgctgatcagcgacttccggcggcagaacagaagaggcggc accaacaagcggaccaccttcaacgccgctggctctctggcccctcacgccagatccctggaattcagcgtgcgg ctgttcgccaactgataa - 393

CMV UL131 FL (SEQ ID NO: 24):
MRLCRVWLSVCLCAVVLGQCQRETAEKNDYYRVPHYWDACSRALPDQTRYKYVEQLVDLTLNYHYDASHGLDNFD

VLKRINVTEVSLLISDFRRQNRRGGTNKRTTFNAAGSLAPHARSLEFSVRLFAN--

---

What is claimed:

1. An immunogenic composition comprising an effective amount of: (i) a plurality of self-replicating RNA molecules that encode a first polypeptide antigen comprising a first epitope and (ii) a second polypeptide antigen comprising a second epitope, wherein said first epitope and second epitope are epitopes from the same pathogen, and wherein the self-replicating RNA molecules:

a) are not encapsulated in virus-like particles, and b) cannot perpetuate themselves in infectious form, and wherein at least haft of the self-replicating RNA molecules are encapsulated within individual liposomes that encapsulate said self-replicating RNA molecules; said composition is formulated for administration to a subject; said composition induces an immunogenic response against said pathogen when administered to a subject in vivo.

2. The immunogenic composition of claim 1, wherein said first epitope and second epitope are the same epitope.

3. The immunogenic composition of claim 1, wherein said first epitope and second epitope are different epitopes.

4. The immunogenic composition of claim 1, wherein said first polypeptide antigen and second polypeptide antigen are substantially the same.

5. The immunogenic composition of claim 1, wherein said first polypeptide antigen is a soluble or membrane anchored polypeptide, and said second polypeptide antigen is a soluble polypeptide.

6. The immunogenic composition of claim 1, wherein said first polypeptide antigen is a fusion polypeptide further comprising a third epitope from a different pathogen.

7. The immunogenic composition of claim 1, wherein said second polypeptide antigen is a fusion polypeptide further comprising a third epitope from a different pathogen.

8. The immunogenic composition of claim 1, wherein said first epitope and second epitope are epitopes from the same subspecies of the pathogen.

9. The immunogenic composition of claim 1, wherein the self-replicating RNA is an alphavirus-derived RNA replicon.

10. The immunogenic composition of claim 1, wherein the self-replicating RNA molecule comprises one or more modified nucleotides.

11. The immunogenic composition of claim 1, wherein the pathogen is a virus, and the first polypeptide antigen and second polypeptide antigen are viral antigens.

12. The immunogenic composition of claim 11, wherein the viral antigens are from respiratory syncytial virus (RSV) or Cytomegalovirus (CMV).

13. The immunogenic composition of claim 12, wherein the viral antigens are RSV-F antigens.

14. The immunogenic composition of claim 13, wherein the RSV-F antigens comprise an amino acid sequence selected from SEQ ID NOs: 25-40.

15. The immunogenic composition of claim 12, wherein the viral antigens are CMV antigens, and wherein the CMV antigens are independently selected from the group consisting of a gB antigen, a gH antigen, a gL antigen, a gM antigen, a gN antigen, a gO antigen, a UL128 antigen, a UL129 antigen, and a UL130 antigen.

16. The immunogenic composition of claim 1, further comprising an adjuvant.

17. The composition of claim 1, wherein the liposomes are formed from a mixture comprising one or more of a cationic lipid and a pegylated lipid.

18. The composition of claim 17, wherein the liposomes are formed from a mixture comprising both of (1) said one or more of a cationic lipid and (2) said pegylated lipid.

19. The composition of claim 18, wherein the liposomes are formed from a mixture further comprising cholesterol.

20. A method for inducing an immune response in a subject comprising administering to a subject in need thereof a therapeutically effective amount of a composition according to claim 1.

21. An immunogenic composition comprising an effective amount of: (i) a plurality of self-replicating RNA molecules that encode a first polypeptide antigen comprising a first epitope and (ii) a second polypeptide antigen comprising a second epitope, wherein said first epitope and second epitope are epitopes from the same pathogen, and wherein the self-replicating RNA molecules:

a) are not encapsulated in virus-like particles, and b) cannot perpetuate themselves in infectious form, and wherein at least half of said self-replicating RNA molecules are encapsulated within individual liposomes, which form an outer layer around an aqueous core containing said self-replicating RNA molecules; said composition is formulated for administration to a subject; and said composition induces an immunogenic response against said pathogen and encoded products of RNA replication and amplification of the self-replicating RNA when administered to a subject in vivo.

* * * * *

SEQUENCE LISTING

<160> NUMBER OF SEQ ID NOS: 40

<210> SEQ ID NO 1
<211> LENGTH: 2727
<212> TYPE: DNA
<213> ORGANISM: Cytomegalovirus

<400> SEQUENCE: 1
atggaaagcc ggatctggtg cctggtcgtg tgcgtgaacc tgtgcatcgt gtgcctggga 60
gccgccgtga gcagcagcag caccagaggc accagcgcca cacacagcca ccacagcagc 120
cacaccacct ctgccgccca cagcagatcc ggcagcgtgt cccagagagt gaccagcagc 180
cagaccgtgt cccacggcgt gaacgagaca atctacaaca ccaccctgaa gtacggcgac 240
gtcgtgggcg tgaataccac caagtacccc tacagagtgt gcagcatggc ccagggcacc 300
gacctgatca gattcgagcg gaacatcgtg tgcaccagca tgaagcccat caacgaggac 360
ctggacgagg gcatcatggt ggtgtacaag agaaacatcg tggcccacac cttcaaagtg 420
cgggtgtacc agaaggtgct gaccttccgg cggagctacg cctacatcca caccacatac 480
ctgctgggca gcaacaccga gtacgtggcc cctcccatgt gggagatcca ccacatcaac 540
agccacagcc agtgctacag cagctacagc cgcgtgatcg ccggcacagt gttcgtggcc 600
taccaccggg acagctacga gaacaagacc atgcagctga tgcccgacga ctacagcaac 660
acccacagca ccagatacgt gaccgtgaag gaccagtggc acagcagagg cagcacctgg 720
ctgtaccggg agacatgcaa cctgaactgc atggtcacca tcaccaccgc cagaagcaag 780 taccccttacc acttcttcgc cacctccacc ggcgacgtgg tggacatcag ccccttctac 840
aacggcacca accggaacgc cagctacttc ggcgagaacg ccgacaagtt cttcatcttc 900
cccaactaca ccatcgtgtc cgacttcggc agacccaaca gcgctctgga aacccacaga 960
ctggtggcct ttctggaacg ggccgacagc gtgatcagct gggacatcca ggacgagaag 1020
aacgtgacct gccagctgac cttctgggag gcctctgaga gaaccatcag aagcgaggcc 1080
gaggacagct accacttcag cagcgccaag atgaccgcca ccttcctgag caagaaacag 1140
gaagtgaaca tgagcgactc cgccctggac tgcgtgaggg acgaggccat caacaagctg 1200
cagcagatct tcaacaccag ctacaaccag acctacgaga agtatggcaa tgtgtccgtg 1260
ttcgagacaa caggcggcct ggtggtgttc tggcagggca tcaagcagaa aagcctggtg 1320
gagctggaac ggctcgccaa ccggtccagc ctgaacctga cccacaaccg gaccaagcgg 1380

-continued agcaccgacg gcaacaacgc aacccacctg tccaacatgg aaagcgtgca caacctggtg 1440
tacgcacagc tgcagttcac ctacgacacc ctgcggggct acatcaacag agccctggcc 1500
cagatcgccg aggcttggtg cgtggaccag cggcggaccc tggaagtgtt caaagagctg 1560
tccaagatca accccagcgc catcctgagc gccatctaca acaagcctat cgccgccaga 1620
ttcatgggcg acgtgctggg cctggccagc tgcgtgacca tcaaccagac cagcgtgaag 1680
gtgctgcggg acatgaacgt gaaagagagc ccaggccgct gctactccag acccgtggtc 1740
atcttcaact tcgccaacag ctcctacgtg cagtacggcc agctgggcga ggacaacgag 1800
atcctgctgg ggaaccaccg gaccgaggaa tgccagctgc ccagcctgaa gatctttatc 1860
gccggcaaca gcgcctacga gtatgtggac tacctgttca agcggatgat cgacctgagc 1920
agcatctcca ccgtggacag catgatcgcc ctggacatcg acccccctgga aaacaccgac 1980 ttccgggtgc tggaactgta cagccagaaa gagctgcgga gcagcaacgt gttcgacctg 2040
gaagagatca tgcgggagtt caacagctac aagcagcgcg tgaaatacgt ggaggacaag 2100
gtggtggacc ccctgcctcc ttacctgaag ggcctggacg acctgatgag cggactgggc 2160
gctgccggaa aagccgtggg agtggccatt ggagctgtgg gcggagctgt ggcctctgtc 2220
gtggaaggcg tcgccacctt tctgaagaac cccttcggcg ccttcaccat catcctggtg 2280
gccattgccg tcgtgatcat cacctacctg atctacaccc ggcagcggag actgtgtacc 2340
cagcccctgc agaacctgtt cccctacctg gtgtccgccg atggcaccac agtgaccagc 2400
ggctccacca aggataccag cctgcaggcc ccacccagct acgaagagag cgtgtacaac 2460
agcggcagaa agggccctgg ccctcccagc tctgatgcca gcacagccgc ccctccctac 2520
accaacgagc aggcctacca gatgctgctg gccctggcta gactggatgc cgagcagagg 2580
gcccagcaga acggcaccga cagcctggat ggcagaaccg gcacccagga caagggccag 2640
aagcccaacc tgctggaccg gctgcggcac cggaagaacg gctaccggca cctgaaggac 2700
agcgacgagg aagagaacgt ctgataa 2727

<210> SEQ ID NO 2
<211> LENGTH: 907
<212> TYPE: PRT
<213> ORGANISM: Cytomegalovirus

<400> SEQUENCE: 2

Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln

-continued

```
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560
```

-continued

```
Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

```
<210> SEQ ID NO 3
<211> LENGTH: 2256
<212> TYPE: DNA
<213> ORGANISM: Cytomegalovirus

<400> SEQUENCE: 3

atggaaagcc ggatctggtg cctggtcgtg tgcgtgaacc tgtgcatcgt gtgcctggga      60

gccgccgtga gcagcagcag caccagaggc accagcgcca cacacagcca ccacagcagc     120
```

```
cacaccacct ctgccgccca cagcagatcc ggcagcgtgt cccagagagt gaccagcagc    180
cagaccgtgt cccacggcgt gaacgagaca atctacaaca ccaccctgaa gtacggcgac    240
gtcgtgggcg tgaataccac caagtacccc tacagagtgt gcagcatggc ccagggcacc    300
gacctgatca gattcgagcg gaacatcgtg tgcaccagca tgaagcccat caacgaggac    360
ctggacgagg gcatcatggt ggtgtacaag agaaacatcg tggcccacac cttcaaagtg    420
cgggtgtacc agaaggtgct gaccttccgg cggagctacg cctacatcca caccacatac    480
ctgctgggca gcaacaccga gtacgtggcc cctcccatgt gggagatcca ccacatcaac    540
agccacagcc agtgctacag cagctacagc cgcgtgatcg ccggcacagt gttcgtggcc    600
taccaccggg acagctacga gaacaagacc atgcagctga tgcccgacga ctacagcaac    660
acccacagca ccagatacgt gaccgtgaag gaccagtggc acagcagagg cagcacctgg    720
ctgtaccggg agacatgcaa cctgaactgc atggtcacca tcaccaccgc cagaagcaag    780
taccccttacc acttcttcgc cacctccacc ggcgacgtgg tggacatcag ccccttctac    840
aacggcacca accggaacgc cagctacttc ggcgagaacg ccgacaagtt cttcatcttc    900
cccaactaca ccatcgtgtc cgacttcggc agacccaaca gcgctctgga aacccacaga    960
ctggtggcct ttctggaacg ggccgacagc gtgatcagct gggacatcca ggacgagaag   1020
aacgtgacct gccagctgac cttctgggag gcctctgaga gaaccatcag aagcgaggcc   1080
gaggacagct accacttcag cagcgccaag atgaccgcca ccttcctgag caagaaacag   1140
gaagtgaaca tgagcgactc cgccctggac tgcgtgaggg acgaggccat caacaagctg   1200
cagcagatct tcaacaccag ctacaaccag acctacgaga agtatggcaa tgtgtccgtg   1260
ttcgagacaa caggcggcct ggtggtgttc tggcagggca tcaagcagaa aagcctggtg   1320
gagctggaac ggctcgccaa ccggtccagc ctgaacctga cccacaaccg gaccaagcgg   1380
agcaccgacg gcaacaacgc aacccacctg tccaacatgg aaagcgtgca caacctggtg   1440
tacgcacagc tgcagttcac ctacgacacc ctgcggggct acatcaacag agccctggcc   1500
cagatcgccg aggcttggtg cgtggaccag cggcggaccc tggaagtgtt caaagagctg   1560
tccaagatca accccagcgc catcctgagc gccatctaca acaagcctat cgccgccaga   1620
ttcatgggcg acgtgctggg cctggccagc tgcgtgacca tcaaccagac cagcgtgaag   1680
gtgctgcggg acatgaacgt gaaagagagc ccaggccgct gctactccag acccgtggtc   1740
atcttcaact tcgccaacag ctcctacgtg cagtacggcc agctgggcga ggacaacgag   1800
atcctgctgg ggaaccaccg gaccgaggaa tgccagctgc ccagcctgaa gatctttatc   1860
gccggcaaca gcgcctacga gtatgtggac tacctgttca agcggatgat cgacctgagc   1920
agcatctcca ccgtggacag catgatcgcc ctggacatcg accccctgga aaacaccgac   1980
ttccgggtgc tggaactgta cagccagaaa gagctgcgga gcagcaacgt gttcgacctg   2040
gaagagatca tgcgggagtt caacagctac aagcagcgcg tgaaatacgt ggaggacaag   2100
gtggtggacc ccctgcctcc ttacctgaag ggcctggacg acctgatgag cggactgggc   2160
gctgccggaa aagccgtggg agtggccatt ggagctgtgg gcggagctgt ggcctctgtc   2220
gtggaaggcg tcgccacctt tctgaagaac tgataa                             2256
```

<210> SEQ ID NO 4
<211> LENGTH: 750
<212> TYPE: PRT
<213> ORGANISM: Cytomegalovirus

<400> SEQUENCE: 4

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415
```

-continued

```
Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn
            740                 745                 750
```

<210> SEQ ID NO 5
<211> LENGTH: 2082
<212> TYPE: DNA
<213> ORGANISM: Cytomegalovirus

<400> SEQUENCE: 5

```
atggaaagcc ggatctggtg cctggtcgtg tgcgtgaacc tgtgcatcgt gtgcctggga      60

gccgccgtga gcagcagcag caccagaggc accagcgcca cacacagcca ccacagcagc     120

cacaccacct ctgccgccca cagcagatcc ggcagcgtgt cccagagagt gaccagcagc     180

cagaccgtgt cccacggcgt gaacgagaca atctacaaca ccaccctgaa gtacggcgac     240
```

-continued

```
gtcgtgggcg tgaataccac caagtacccc tacagagtgt gcagcatggc ccagggcacc    300

gacctgatca gattcgagcg gaacatcgtg tgcaccagca tgaagcccat caacgaggac    360

ctggacgagg gcatcatggt ggtgtacaag agaaacatcg tggcccacac cttcaaagtg    420

cgggtgtacc agaaggtgct gaccttccgg cggagctacg cctacatcca caccacatac    480

ctgctgggca gcaacaccga gtacgtggcc cctcccatgt gggagatcca ccacatcaac    540

agccacagcc agtgctacag cagctacagc cgcgtgatcg ccggcacagt gttcgtggcc    600

taccaccggg acagctacga gaacaagacc atgcagctga tgcccgacga ctacagcaac    660

acccacagca ccagatacgt gaccgtgaag gaccagtggc acagcagagg cagcacctgg    720

ctgtaccggg agacatgcaa cctgaactgc atggtcacca tcaccaccgc cagaagcaag    780

taccccttacc acttcttcgc cacctccacc ggcgacgtgg tggacatcag ccccttctac    840

aacggcacca accggaacgc cagctacttc ggcgagaacg ccgacaagtt cttcatcttc    900

cccaactaca ccatcgtgtc cgacttcggc agacccaaca gcgctctgga aacccacaga    960

ctggtggcct ttctggaacg ggccgacagc gtgatcagct gggacatcca ggacgagaag   1020

aacgtgacct gccagctgac cttctgggag gcctctgaga gaaccatcag aagcgaggcc   1080

gaggacagct accacttcag cagcgccaag atgaccgcca ccttcctgag caagaaacag   1140

gaagtgaaca tgagcgactc cgccctggac tgcgtgaggg acgaggccat caacaagctg   1200

cagcagatct tcaacaccag ctacaaccag acctacgaga agtatggcaa tgtgtccgtg   1260

ttcgagacaa caggcggcct ggtggtgttc tggcagggca tcaagcagaa aagcctggtg   1320

gagctggaac ggctcgccaa ccggtccagc ctgaacctga cccacaaccg gaccaagcgg   1380

agcaccgacg gcaacaacgc aacccacctg tccaacatgg aaagcgtgca caacctggtg   1440

tacgcacagc tgcagttcac ctacgacacc ctgcggggct acatcaacag agccctggcc   1500

cagatcgccg aggcttggtg cgtggaccag cggcggaccc tggaagtgtt caaagagctg   1560

tccaagatca accccagcgc catcctgagc gccatctaca acaagcctat cgccgccaga   1620

ttcatgggcg acgtgctggg cctggccagc tgcgtgacca tcaaccagac cagcgtgaag   1680

gtgctgcggg acatgaacgt gaaagagagc ccaggccgct gctactccag acccgtggtc   1740

atcttcaact tcgccaacag ctcctacgtg cagtacggcc agctgggcga ggacaacgag   1800

atcctgctgg ggaaccaccg gaccgaggaa tgccagctgc ccagcctgaa gatctttatc   1860

gccggcaaca gcgcctacga gtatgtggac tacctgttca agcggatgat cgacctgagc   1920

agcatctcca ccgtggacag catgatcgcc ctggacatcg acccccctgga aaacaccgac   1980

ttccgggtgc tggaactgta cagccagaaa gagctgcgga gcagcaacgt gttcgacctg   2040

gaagagatca tgcgggagtt caacagctac aagcagtgat aa                      2082
```

<210> SEQ ID NO 6
<211> LENGTH: 692
<212> TYPE: PRT
<213> ORGANISM: Cytomegalovirus

<400> SEQUENCE: 6

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45
```

-continued

```
Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
```

-continued

```
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln
    690
```

<210> SEQ ID NO 7
<211> LENGTH: 2232
<212> TYPE: DNA
<213> ORGANISM: Cytomegalovirus

<400> SEQUENCE: 7

```
atgaggcctg gcctgccctc ctacctgatc atcctggccg tgtgcctgtt cagccacctg     60

ctgtccagca gatacggcgc cgaggccgtg agcgagcccc tggacaaggc tttccacctg    120

ctgctgaaca cctacggcag acccatccgg tttctgcggg agaacaccac ccagtgcacc    180

tacaacagca gcctgcggaa cagcaccgtc gtgagagaga acgccatcag cttcaacttt    240

ttccagagct acaaccagta ctacgtgttc cacatgccca gatgcctgtt tgccggccct    300

ctggccgagc agttcctgaa ccaggtggac ctgaccgaga cactggaaag ataccagcag    360

cggctgaata cctacgccct ggtgtccaag gacctggcca gctaccggtc ctttagccag    420

cagctcaagg ctcaggatag cctcggcgag cagcctacca ccgtgccccc tcccatcgac    480

ctgagcatcc cccacgtgtg gatgcctccc cagaccaccc ctcacggctg gaccgagagc    540

cacaccacct ccggcctgca cagaccccac ttcaaccaga cctgcatcct gttcgacggc    600

cacgacctgc tgtttagcac cgtgaccccc tgcctgcacc agggcttcta cctgatcgac    660

gagctgagat acgtgaagat caccctgacc gaggatttct tcgtggtcac cgtgtccatc    720

gacgacgaca cccccatgct gctgatcttc ggccacctgc ccagagtgct gttcaaggcc    780

ccctaccagc gggacaactt catcctgcgg cagaccgaga agcacgagct gctggtgctg    840
```

```
gtcaagaagg accagctgaa ccggcactcc tacctgaagg accccgactt cctggacgcc    900

gccctggact tcaactacct ggacctgagc gccctgctga gaaacagctt ccacagatac    960

gccgtggacg tgctgaagtc cggacggtgc cagatgctcg atcggcggac cgtggagatg   1020

gccttcgcct atgccctcgc cctgttcgcc gctgccagac aggaagaggc tggcgcccag   1080

gtgtcagtgc ccagagccct ggatagacag gccgccctgc tgcagatcca ggaattcatg   1140

atcacctgcc tgagccagac ccccccctaga accaccctgc tgctgtaccc cacagccgtg   1200

gatctggcca agagggccct gtggaccccc aaccagatca ccgacatcac aagcctcgtg   1260

cggctcgtgt acatcctgag caagcagaac cagcagcacc tgatccccca gtgggccctg   1320

agacagatcg ccgacttcgc cctgaagctg cacaagaccc atctggccag ctttctgagc   1380

gccttcgcca ggcaggaact gtacctgatg ggcagcctgg tccacagcat gctggtgcat   1440

accaccgagc ggcgggagat cttcatcgtg gagacaggcc tgtgtagcct ggccgagctg   1500

tcccacttta cccagctgct ggcccaccct caccacgagt acctgagcga cctgtacacc   1560

ccctgcagca gcagcggcag acgggaccac agcctggaac ggctgaccag actgttcccc   1620

gatgccaccg tgcctgctac agtgcctgcc gccctgtcca tcctgtccac catgcagccc   1680

agcaccctgg aaaccttccc cgacctgttc tgcctgcccc tgggcgagag ctttagcgcc   1740

ctgaccgtgt ccgagcacgt gtcctacatc gtgaccaatc agtacctgat caagggcatc   1800

agctaccccg tgtccaccac agtcgtgggc cagagcctga tcatcaccca gaccgacagc   1860

cagaccaagt gcgagctgac ccggaacatg cacaccacac acagcatcac cgtggccctg   1920

aacatcagcc tggaaaactg cgctttctgt cagtctgccc tgctggaata cgacgatacc   1980

cagggcgtga tcaacatcat gtacatgcac gacagcgacg acgtgctgtt cgccctggac   2040

ccctacaacg aggtggtggt gtccagcccc cggacccact acctgatgct gctgaagaac   2100

ggcaccgtgc tggaagtgac cgacgtggtg gtggacgcca ccgacagcag actgctgatg   2160

atgagcgtgt acgccctgag cgccatcatc ggcatctacc tgctgtaccg gatgctgaaa   2220

acctgctgat aa                                                       2232

<210> SEQ ID NO 8
<211> LENGTH: 742
<212> TYPE: PRT
<213> ORGANISM: Cytomegalovirus

<400> SEQUENCE: 8

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
```

```
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540
```

```
Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740


<210> SEQ ID NO 9
<211> LENGTH: 2151
<212> TYPE: DNA
<213> ORGANISM: Cytomegalovirus

<400> SEQUENCE: 9

atgaggcctg gcctgccctc ctacctgatc atcctggccg tgtgcctgtt cagccacctg      60

ctgtccagca gatacggcgc cgaggccgtg agcgagcccc tggacaaggc tttccacctg     120

ctgctgaaca cctacggcag acccatccgg tttctgcggg agaacaccac ccagtgcacc     180

tacaacagca gcctgcggaa cagcaccgtc gtgagagaga acgccatcag cttcaacttt     240

ttccagagct acaaccagta ctacgtgttc cacatgccca gatgcctgtt tgccggccct     300

ctggccgagc agttcctgaa ccaggtggac ctgaccgaga cactggaaag ataccagcag     360

cggctgaata cctacgccct ggtgtccaag gacctggcca gctaccggtc ctttagccag     420

cagctcaagg ctcaggatag cctcggcgag cagcctacca ccgtgccccc tcccatcgac     480

ctgagcatcc cccacgtgtg gatgcctccc cagaccaccc ctcacggctg gaccgagagc     540

cacaccacct ccggcctgca cagaccccac ttcaaccaga cctgcatcct gttcgacggc     600

cacgacctgc tgtttagcac cgtgaccccc tgcctgcacc agggcttcta cctgatcgac     660

gagctgagat acgtgaagat caccctgacc gaggatttct tcgtggtcac cgtgtccatc     720

gacgacgaca cccccatgct gctgatcttc ggccacctgc ccagagtgct gttcaaggcc     780

ccctaccagc gggacaactt catcctgcgg cagaccgaga agcacgagct gctggtgctg     840

gtcaagaagg accagctgaa ccggcactcc tacctgaagg accccgactt cctggacgcc     900

gccctggact tcaactacct ggacctgagc gccctgctga gaaacagctt ccacagatac     960
```

-continued

```
gccgtggacg tgctgaagtc cggacggtgc cagatgctcg atcggcggac cgtggagatg   1020

gccttcgcct atgccctcgc cctgttcgcc gctgccagac aggaagaggc tggcgcccag   1080

gtgtcagtgc ccagagccct ggatagacag gccgccctgc tgcagatcca ggaattcatg   1140

atcacctgcc tgagccagac ccccccctaga accaccctgc tgctgtaccc cacagccgtg   1200

gatctggcca agagggccct gtggaccccc aaccagatca ccgacatcac aagcctcgtg   1260

cggctcgtgt acatcctgag caagcagaac cagcagcacc tgatccccca gtgggccctg   1320

agacagatcg ccgacttcgc cctgaagctg cacaagaccc atctggccag ctttctgagc   1380

gccttcgcca ggcaggaact gtacctgatg ggcagcctgg tccacagcat gctggtgcat   1440

accaccgagc ggcgggagat cttcatcgtg gagacaggcc tgtgtagcct ggccgagctg   1500

tcccacttta cccagctgct ggcccaccct caccacgagt acctgagcga cctgtacacc   1560

ccctgcagca gcagcggcag acgggaccac agcctggaac ggctgaccag actgttcccc   1620

gatgccaccg tgcctgctac agtgcctgcc gccctgtcca tcctgtccac catgcagccc   1680

agcaccctgg aaaccttccc cgacctgttc tgcctgcccc tgggcgagag ctttagcgcc   1740

ctgaccgtgt ccgagcacgt gtcctacatc gtgaccaatc agtacctgat caagggcatc   1800

agctaccccg tgtccaccac agtcgtgggc cagagcctga tcatcaccca gaccgacagc   1860

cagaccaagt gcgagctgac ccggaacatg cacaccacac acagcatcac cgtggccctg   1920

aacatcagcc tggaaaactg cgctttctgt cagtctgccc tgctggaata cgacgatacc   1980

cagggcgtga tcaacatcat gtacatgcac gacagcgacg acgtgctgtt cgccctggac   2040

ccctacaacg aggtggtggt gtccagcccc cggacccact acctgatgct gctgaagaac   2100

ggcaccgtgc tggaagtgac cgacgtggtg gtggacgcca ccgactgata a            2151
```

```
<210> SEQ ID NO 10
<211> LENGTH: 715
<212> TYPE: PRT
<213> ORGANISM: Cytomegalovirus

<400> SEQUENCE: 10

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160
```

-continued

```
Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
```

```
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp
705                 710                 715


<210> SEQ ID NO 11
<211> LENGTH: 840
<212> TYPE: DNA
<213> ORGANISM: Cytomegalovirus

<400> SEQUENCE: 11

atgtgcagaa ggcccgactg cggcttcagc ttcagccctg gacccgtgat cctgctgtgg      60

tgctgcctgc tgctgcctat cgtgtcctct gccgccgtgt ctgtggcccc tacagccgcc     120

gagaaggtgc cagccgagtg ccccgagctg accagaagat gcctgctggg cgaggtgttc     180

gagggcgaca agtacgagag ctggctgcgg cccctggtca acgtgaccgg cagagatggc     240

cccctgagcc agctgatccg gtacagaccc gtgacccccg aggccgccaa tagcgtgctg     300

ctggacgagg ccttcctgga taccctggcc ctgctgtaca acaaccccga ccagctgaga     360

gccctgctga ccctgctgtc cagcgacacc gcccccagat ggatgaccgt gatgcggggc     420

tacagcgagt gtggagatgg cagccctgcc gtgtacacct gcgtggacga cctgtgcaga     480

ggctacgacc tgaccagact gagctacggc cggtccatct tcacagagca cgtgctgggc     540

ttcgagctgg tgcccccca g cctgttcaac gtggtggtgg ccatccggaa cgaggccacc     600

agaaccaaca gagccgtgcg gctgcctgtg tctacagccg ctgcacctga gggcatcaca     660

ctgttctacg gcctgtacaa cgccgtgaaa gagttctgcc tccggcacca gctggatccc     720

cccctgctga gacacctgga caagtactac gccggcctgc ccccagagct gaagcagacc     780

agagtgaacc tgcccgccca cagcagatat ggccctcagg ccgtggacgc cagatgataa     840


<210> SEQ ID NO 12
<211> LENGTH: 278
<212> TYPE: PRT
<213> ORGANISM: Cytomegalovirus

<400> SEQUENCE: 12

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45
```

```
Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275
```

<210> SEQ ID NO 13
<211> LENGTH: 1119
<212> TYPE: DNA
<213> ORGANISM: Cytomegalovirus

<400> SEQUENCE: 13

```
atggccccca gccacgtgga caaagtgaac acccggactt ggagcgccag catcgtgttc      60

atggtgctga ccttcgtgaa cgtgtccgtg cacctggtgc tgtccaactt cccccacctg     120

ggctacccct gcgtgtacta ccacgtggtg gacttcgagc ggctgaacat gagcgcctac     180

aacgtgatgc acctgcacac ccccatgctg tttctggaca gcgtgcagct cgtgtgctac     240

gccgtgttca tgcagctggt gtttctggcc gtgaccatct actacctcgt gtgctggatc     300

aagatcagca tgcggaagga caagggcatg agcctgaacc agagcacccg ggacatcagc     360

tacatgggcg acagcctgac cgccttcctg ttcatcctga gcatggacac cttccagctg     420

ttcaccctga ccatgagctt ccggctgccc agcatgatcg ccttcatggc cgccgtgcac     480

tttttctgtc tgaccatctt caacgtgtcc atggtcaccc agtaccggtc ctacaagcgg     540

agcctgttct tcttctcccg gctgcacccc aagctgaagg gcaccgtgca gttccggacc     600

ctgatcgtga acctggtgga ggtggccctg ggcttcaata ccaccgtggt ggctatggcc     660

ctgtgctacg gcttcggcaa caacttcttc gtgcggaccg gccatatggt gctggccgtg     720

ttcgtggtgt acgccatcat cagcatcatc tactttctgc tgatcgaggc cgtgttcttc     780
```

```
cagtacgtga aggtgcagtt cggctaccat ctgggcgcct ttttcggcct gtgcggcctg    840

atctacccca tcgtgcagta cgacaccttc ctgagcaacg agtaccggac cggcatcagc    900

tggtccttcg gaatgctgtt cttcatctgg gccatgttca ccacctgcag agccgtgcgg    960

tacttcagag gcagaggcag cggctccgtg aagtaccagg ccctggccac agcctctggc   1020

gaagaggtgg ccgccctgag ccaccacgac agcctggaaa gcagacggct gcgggaggaa   1080

gaggacgacg acgacgagga cttcgaggac gcctgataa                          1119


<210> SEQ ID NO 14
<211> LENGTH: 371
<212> TYPE: PRT
<213> ORGANISM: Cytomegalovirus

<400> SEQUENCE: 14

Met Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320
```

```
Tyr Phe Arg Gly Arg Gly Ser Gly Ser Val Lys Tyr Gln Ala Leu Ala
                325                 330                 335

Thr Ala Ser Gly Glu Glu Val Ala Ala Leu Ser His His Asp Ser Leu
            340                 345                 350

Glu Ser Arg Arg Leu Arg Glu Glu Glu Asp Asp Asp Asp Glu Asp Phe
        355                 360                 365

Glu Asp Ala
    370


<210> SEQ ID NO 15
<211> LENGTH: 411
<212> TYPE: DNA
<213> ORGANISM: Cytomegalovirus

<400> SEQUENCE: 15

atggaatgga acaccctggt cctgggcctg ctggtgctgt ctgtcgtggc cagcagcaac      60

aacacatcca cagccagcac ccctagacct agcagcagca cccacgccag cactaccgtg     120

aaggctacca ccgtggccac cacaagcacc accactgcta ccagcaccag ctccaccacc     180

tctgccaagc ctggctctac cacacacgac cccaacgtga tgaggcccca cgcccacaac     240

gacttctaca acgctcactg caccagccac atgtacgagc tgtccctgag cagctttgcc     300

gcctggtgga ccatgctgaa cgccctgatc ctgatgggcg ccttctgcat cgtgctgcgg     360

cactgctgct tccagaactt caccgccacc accaccaagg gctactgata a              411


<210> SEQ ID NO 16
<211> LENGTH: 135
<212> TYPE: PRT
<213> ORGANISM: Cytomegalovirus

<400> SEQUENCE: 16

Met Glu Trp Asn Thr Leu Val Leu Gly Leu Leu Val Leu Ser Val Val
1               5                   10                  15

Ala Ser Ser Asn Asn Thr Ser Thr Ala Ser Thr Pro Arg Pro Ser Ser
            20                  25                  30

Ser Thr His Ala Ser Thr Thr Val Lys Ala Thr Thr Val Ala Thr Thr
        35                  40                  45

Ser Thr Thr Thr Ala Thr Ser Thr Ser Ser Thr Thr Ser Ala Lys Pro
    50                  55                  60

Gly Ser Thr Thr His Asp Pro Asn Val Met Arg Pro His Ala His Asn
65                  70                  75                  80

Asp Phe Tyr Asn Ala His Cys Thr Ser His Met Tyr Glu Leu Ser Leu
                85                  90                  95

Ser Ser Phe Ala Ala Trp Trp Thr Met Leu Asn Ala Leu Ile Leu Met
            100                 105                 110

Gly Ala Phe Cys Ile Val Leu Arg His Cys Cys Phe Gln Asn Phe Thr
        115                 120                 125

Ala Thr Thr Thr Lys Gly Tyr
    130                 135


<210> SEQ ID NO 17
<211> LENGTH: 1422
<212> TYPE: DNA
<213> ORGANISM: Cytomegalovirus

<400> SEQUENCE: 17

atgggcaaga aagaaatgat catggtcaag ggcatcccca agatcatgct gctgattagc      60
```

```
atcacctttc tgctgctgtc cctgatcaac tgcaacgtgc tggtcaacag ccggggcacc    120

agaagatcct ggccctacac cgtgctgtcc taccggggca aagagatcct gaagaagcag    180

aaagaggaca tcctgaagcg gctgatgagc accagcagcg acggctaccg gttcctgatg    240

taccccagcc agcagaaatt ccacgccatc gtgatcagca tggacaagtt cccccaggac    300

tacatcctgg ccggacccat ccggaacgac agcatcaccc acatgtggtt cgacttctac    360

agcacccagc tgcggaagcc cgccaaatac gtgtacagcg agtacaacca caccgcccac    420

aagatcaccc tgaggcctcc cccttgtggc accgtgccca gcatgaactg cctgagcgag    480

atgctgaacg tgtccaagcg gaacgacacc ggcgagaagg gctgcggcaa cttcaccacc    540

ttcaacccca tgttcttcaa cgtgccccgg tggaacacca agctgtacat cggcagcaac    600

aaagtgaacg tggacagcca gaccatctac tttctgggcc tgaccgccct gctgctgaga    660

tacgcccagc ggaactgcac ccggtccttc tacctggtca acgccatgag ccggaacctg    720

ttccgggtgc ccaagtacat caacggcacc aagctgaaga acaccatgcg gaagctgaag    780

cggaagcagg ccctggtcaa agagcagccc cagaagaaga acaagaagtc ccagagcacc    840

accacccccct acctgagcta caccacctcc accgccttca acgtgaccac caacgtgacc    900

tacagcgcca cagccgccgt gaccagagtg gccacaagca ccaccggcta ccggcccgac    960

agcaacttta tgaagtccat catggccacc cagctgagag atctggccac ctgggtgtac   1020

accaccctgc ggtacagaaa cgagcccttc tgcaagcccg accggaacag aaccgccgtg   1080

agcgagttca tgaagaatac ccacgtgctg atcagaaacg agacacccta caccatctac   1140

ggcaccctgg acatgagcag cctgtactac aacgagacaa tgagcgtgga gaacgagaca   1200

gccagcgaca acaacgaaac cacccccacc tcccccagca cccggttcca gcggaccttc   1260

atcgaccccc tgtgggacta cctggacagc ctgctgttcc tggacaagat ccggaacttc   1320

agcctgcagc tgcccgccta cggcaatctg acccccccctg agcacagaag ggccgccaac   1380

ctgagcaccc tgaacagcct gtggtggtgg agccagtgat aa                       1422
```

<210> SEQ ID NO 18
<211> LENGTH: 472
<212> TYPE: PRT
<213> ORGANISM: Cytomegalovirus

<400> SEQUENCE: 18

```
Met Gly Lys Lys Glu Met Ile Met Val Lys Gly Ile Pro Lys Ile Met
1               5                   10                  15

Leu Leu Ile Ser Ile Thr Phe Leu Leu Leu Ser Leu Ile Asn Cys Asn
            20                  25                  30

Val Leu Val Asn Ser Arg Gly Thr Arg Arg Ser Trp Pro Tyr Thr Val
        35                  40                  45

Leu Ser Tyr Arg Gly Lys Glu Ile Leu Lys Lys Gln Lys Glu Asp Ile
    50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
                85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125
```

-continued

```
Lys Tyr Val Tyr Ser Glu Tyr Asn His Thr Ala His Lys Ile Thr Leu
    130                 135                 140

Arg Pro Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270

Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
            340                 345                 350

Pro Asp Arg Asn Arg Thr Ala Val Ser Glu Phe Met Lys Asn Thr His
        355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
            420                 425                 430

Phe Leu Asp Lys Ile Arg Asn Phe Ser Leu Gln Leu Pro Ala Tyr Gly
        435                 440                 445

Asn Leu Thr Pro Pro Glu His Arg Arg Ala Ala Asn Leu Ser Thr Leu
    450                 455                 460

Asn Ser Leu Trp Trp Trp Ser Gln
465                 470
```

<210> SEQ ID NO 19
<211> LENGTH: 519
<212> TYPE: DNA
<213> ORGANISM: Cytomegalovirus

<400> SEQUENCE: 19

```
atgagcccca aggacctgac ccccttcctg acaaccctgt ggctgctcct gggccatagc      60

agagtgccta gagtgcgggc cgaggaatgc tgcgagttca tcaacgtgaa ccacccccc      120

gagcggtgct acgacttcaa gatgtgcaac cggttcaccg tggccctgag atgccccgac     180
```

ggcgaagtgt gctacagccc cgagaaaacc gccgagatcc ggggcatcgt gaccaccatg 240
acccacagcc tgacccggca ggtggtgcac aacaagctga ccagctgcaa ctacaacccc 300
ctgtacctgg aagccgacgg ccggatcaga tgcggcaaag tgaacgacaa ggcccagtac 360
ctgctgggag ccgccggaag cgtgccctac cggtggatca acctggaata cgacaagatc 420
acccggatcg tgggcctgga ccagtacctg gaaagcgtga agaagcacaa gcggctggac 480
gtgtgcagag ccaagatggg ctacatgctg cagtgataa 519

<210> SEQ ID NO 20
<211> LENGTH: 171
<212> TYPE: PRT
<213> ORGANISM: Cytomegalovirus

<400> SEQUENCE: 20

Met Ser Pro Lys Asp Leu Thr Pro Phe Leu Thr Thr Leu Trp Leu Leu
1 5 10 15

Leu Gly His Ser Arg Val Pro Arg Val Arg Ala Glu Glu Cys Cys Glu
20 25 30

Phe Ile Asn Val Asn His Pro Pro Glu Arg Cys Tyr Asp Phe Lys Met
35 40 45

Cys Asn Arg Phe Thr Val Ala Leu Arg Cys Pro Asp Gly Glu Val Cys
50 55 60

Tyr Ser Pro Glu Lys Thr Ala Glu Ile Arg Gly Ile Val Thr Thr Met
65 70 75 80

Thr His Ser Leu Thr Arg Gln Val Val His Asn Lys Leu Thr Ser Cys
85 90 95

Asn Tyr Asn Pro Leu Tyr Leu Glu Ala Asp Gly Arg Ile Arg Cys Gly
100 105 110

Lys Val Asn Asp Lys Ala Gln Tyr Leu Leu Gly Ala Ala Gly Ser Val
115 120 125

Pro Tyr Arg Trp Ile Asn Leu Glu Tyr Asp Lys Ile Thr Arg Ile Val
130 135 140

Gly Leu Asp Gln Tyr Leu Glu Ser Val Lys Lys His Lys Arg Leu Asp
145 150 155 160

Val Cys Arg Ala Lys Met Gly Tyr Met Leu Gln
165 170

<210> SEQ ID NO 21
<211> LENGTH: 648
<212> TYPE: DNA
<213> ORGANISM: Cytomegalovirus

<400> SEQUENCE: 21
atgctgcggc tgctgctgag acaccacttc cactgcctgc tgctgtgtgc cgtgtgggcc 60
accccttgtc tggccagccc ttggagcacc ctgaccgcca accagaaccc tagccccccct 120 tggtccaagc tgacctacag caagccccac gacgccgcca ccttctactg cccctttctg 180
taccccagcc ctcccagaag ccccctgcag ttcagcggct tccagagagt gtccaccggc 240
cctgagtgcc ggaacgagac actgtacctg ctgtacaacc gggagggcca gacactggtg 300
gagcggagca gcacctgggt gaaaaaagtg atctggtatc tgagcggccg gaaccagacc 360
atcctgcagc ggatgcccag aaccgccagc aagcccagcg acggcaacgt gcagatcagc 420
gtggaggacg ccaaaatctt cggcgcccac atggtgccca agcagaccaa gctgctgaga 480
ttcgtggtca acgacggcac cagatatcag atgtgcgtga tgaagctgga aagctgggcc 540

```
cacgtgttcc gggactactc cgtgagcttc caggtccggc tgaccttcac cgaggccaac    600

aaccagacct acaccttctg cacccacccc aacctgatcg tgtgataa                 648


<210> SEQ ID NO 22
<211> LENGTH: 214
<212> TYPE: PRT
<213> ORGANISM: Cytomegalovirus

<400> SEQUENCE: 22

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210


<210> SEQ ID NO 23
<211> LENGTH: 393
<212> TYPE: DNA
<213> ORGANISM: Cytomegalovirus

<400> SEQUENCE: 23

atgcggctgt gcagagtgtg gctgtccgtg tgcctgtgtg ccgtggtgct gggccagtgc     60

cagagagaga cagccgagaa gaacgactac taccgggtgc cccactactg ggatgcctgc    120

agcagagccc tgcccgacca gacccggtac aaatacgtgg agcagctcgt ggacctgacc    180

ctgaactacc actacgacgc cagccacggc ctggacaact tcgacgtgct gaagcggatc    240

aacgtgaccg aggtgtccct gctgatcagc gacttccggc ggcagaacag aagaggcggc    300

accaacaagc ggaccacctt caacgccgct ggctctctgg cccctcacgc cagatccctg    360

gaattcagcg tgcggctgtt cgccaactga taa                                 393


<210> SEQ ID NO 24
```

<211> LENGTH: 129
<212> TYPE: PRT
<213> ORGANISM: Cytomegalovirus

<400> SEQUENCE: 24

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 25
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Thr Pro Ala Thr Asn Asn Arg Ala Arg Lys Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Lys Lys Phe Leu Gly Phe Leu Leu Gly Val Gly Ser Ala
        35                  40                  45

Ile Ala Ser
    50

<210> SEQ ID NO 26
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Thr Pro Ala Thr Asn Asn Arg Ala Arg Gln Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Phe Leu Gly Phe Leu Leu Gly Val Gly Ser Ala Ile Ala Ser
        35                  40                  45

<210> SEQ ID NO 27

<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Thr Pro Ala Thr Asn Asn Gln Ala Gln Asn Glu Leu Pro Gln Phe Met
1               5                   10                  15

Asn Tyr Thr Leu Asn Asn Ala Asn Asn Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50
```

<210> SEQ ID NO 28
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Thr Pro Ala Thr Asn Asn Gln Ala Gln Asn Glu Leu Pro Gln Phe Met
1               5                   10                  15

Asn Tyr Thr Leu Asn Asn Ala Gln Gln Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50
```

<210> SEQ ID NO 29
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Thr Pro Ala Thr Asn Asn Gln Ala Gln Asn Gln Asn Gln Asn Gln Asn
1               5                   10                  15

Phe Leu Gly Phe Leu Leu Gly Val Gly Ser Ala Ile Ala Ser
            20                  25                  30
```

<210> SEQ ID NO 30
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

```
Thr Pro Ala Thr Asn Asn Gln Ala Gln Asn Gln Asn Gln Asn Phe Leu
1               5                   10                  15
```

```
Gly Phe Leu Leu Gly Val Gly Ser Ala Ile Ala Ser
            20                  25


<210> SEQ ID NO 31
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Thr Pro Ala Thr Asn Asn Arg Ala Arg Gln Gln Gln Gln Arg Phe Leu
1               5                   10                  15

Gly Phe Leu Leu Gly Val Gly Ser Ala Ile Ala Ser
            20                  25


<210> SEQ ID NO 32
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Thr Pro Ala Thr Asn Asn Arg Ala Arg Arg Glu Leu Pro Gln Phe Met
1               5                   10                  15

Asn Tyr Thr Leu Asn Asn Ala Gln Gln Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50


<210> SEQ ID NO 33
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Thr Pro Ala Thr Asn Asn Gln Ala Gln Asn Glu Leu Pro Gln Phe Met
1               5                   10                  15

Asn Tyr Thr Leu Asn Asn Ala Gln Gln Thr Asn Val Thr Leu Ser Lys
            20                  25                  30

Lys Arg Lys Arg Arg Phe Leu Gly Phe Leu Leu Gly Val Gly Ser Ala
        35                  40                  45

Ile Ala Ser
    50


<210> SEQ ID NO 34
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 34

Thr Pro Ala Thr Asn Asn Arg Ala Arg Arg Glu Leu Pro Arg Phe Met
1 5 10 15

Asn Tyr Thr Leu Asn Asn Ala Lys Lys Thr Asn Val Thr Leu Ser Lys
20 25 30

Lys Arg Lys Arg Arg Ser Ala Ile Ala Ser
35 40

<210> SEQ ID NO 35
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Thr Pro Ala Thr Asn Asn Arg Ala Arg Arg Glu Leu Pro Arg Phe Met
1 5 10 15

Asn Tyr Thr Leu Asn Asn Ala Lys Lys Thr Asn Val Thr Leu Ser Lys
20 25 30

Lys Arg Lys Arg Arg Gly Val Gly Ser Ala Ile Ala Ser
35 40 45

<210> SEQ ID NO 36
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Thr Pro Ala Thr Asn Asn Arg Ala Arg Arg Glu Leu Pro Arg Phe Met
1 5 10 15

Asn Tyr Thr Leu Asn Asn Ala Lys Lys Thr Asn Val Thr Leu Ser Lys
20 25 30

Lys Arg Lys Arg Arg Ala Ser Ala Ile Ala Ser
35 40

<210> SEQ ID NO 37
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Thr Pro Ala Thr Asn Asn Ile Glu Gly Arg Glu Leu Pro Arg Phe Met
1 5 10 15

Asn Tyr Thr Leu Asn Asn Ala Lys Lys Thr Asn Val Thr Leu Ser Lys
20 25 30

Lys Ile Glu Gly Arg Phe Leu Gly Phe Leu Leu Gly Val Gly Ser Ala
35 40 45

Ile Ala Ser
50

<210> SEQ ID NO 38

```
<211> LENGTH: 528
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Ser Ala Ile Ala Ser Gly Val Ala
    130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
            180                 185                 190

Gln Leu Leu Pro Ile Val Asn Lys Gln Ser Cys Ser Ile Ser Asn Ile
        195                 200                 205

Glu Thr Val Ile Glu Phe Gln Gln Lys Asn Asn Arg Leu Leu Glu Ile
    210                 215                 220

Thr Arg Glu Arg Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
        275                 280                 285

Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365
```

```
Glu Val Asn Leu Cys Asn Val Asp Ile Phe Asn Pro Lys Tyr Asp Cys
    370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

Ile Arg Lys Ser Asp Glu Leu Leu His Asn Val Asn Ala Gly Lys Ser
            500                 505                 510

Thr Thr Asn Gly Gly Ser Ala Gly Ser Gly His His His His His His
        515                 520                 525


<210> SEQ ID NO 39
<211> LENGTH: 531
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Gly Val Gly Ser Ala Ile Ala Ser
    130                 135                 140

Gly Val Ala Val Ser Lys Val Leu His Leu Glu Gly Glu Val Asn Lys
145                 150                 155                 160

Ile Lys Ser Ala Leu Leu Ser Thr Asn Lys Ala Val Val Ser Leu Ser
                165                 170                 175

Asn Gly Val Ser Val Leu Thr Ser Lys Val Leu Asp Leu Lys Asn Tyr
            180                 185                 190

Ile Asp Lys Gln Leu Leu Pro Ile Val Asn Lys Gln Ser Cys Ser Ile
```

195 200 205

Ser Asn Ile Glu Thr Val Ile Glu Phe Gln Gln Lys Asn Asn Arg Leu
210 215 220

Leu Glu Ile Thr Arg Glu Arg Ser Val Asn Ala Gly Val Thr Thr Pro
225 230 235 240

Val Ser Thr Tyr Met Leu Thr Asn Ser Glu Leu Leu Ser Leu Ile Asn
245 250 255

Asp Met Pro Ile Thr Asn Asp Gln Lys Lys Leu Met Ser Asn Asn Val
260 265 270

Gln Ile Val Arg Gln Gln Ser Tyr Ser Ile Met Ser Ile Ile Lys Glu
275 280 285

Glu Val Leu Ala Tyr Val Val Gln Leu Pro Leu Tyr Gly Val Ile Asp
290 295 300

Thr Pro Cys Trp Lys Leu His Thr Ser Pro Leu Cys Thr Thr Asn Thr
305 310 315 320

Lys Glu Gly Ser Asn Ile Cys Leu Thr Arg Thr Asp Arg Gly Trp Tyr
325 330 335

Cys Asp Asn Ala Gly Ser Val Ser Phe Phe Pro Gln Ala Glu Thr Cys
340 345 350

Lys Val Gln Ser Asn Arg Val Phe Cys Asp Thr Met Asn Ser Leu Thr
355 360 365

Leu Pro Ser Glu Val Asn Leu Cys Asn Val Asp Ile Phe Asn Pro Lys
370 375 380

Tyr Asp Cys Lys Ile Met Thr Ser Lys Thr Asp Val Ser Ser Ser Val
385 390 395 400

Ile Thr Ser Leu Gly Ala Ile Val Ser Cys Tyr Gly Lys Thr Lys Cys
405 410 415

Thr Ala Ser Asn Lys Asn Arg Gly Ile Ile Lys Thr Phe Ser Asn Gly
420 425 430

Cys Asp Tyr Val Ser Asn Lys Gly Val Asp Thr Val Ser Val Gly Asn
435 440 445

Thr Leu Tyr Tyr Val Asn Lys Gln Glu Gly Lys Ser Leu Tyr Val Lys
450 455 460

Gly Glu Pro Ile Ile Asn Phe Tyr Asp Pro Leu Val Phe Pro Ser Asp
465 470 475 480

Glu Phe Asp Ala Ser Ile Ser Gln Val Asn Glu Lys Ile Asn Gln Ser
485 490 495

Leu Ala Phe Ile Arg Lys Ser Asp Glu Leu Leu His Asn Val Asn Ala
500 505 510

Gly Lys Ser Thr Thr Asn Gly Gly Ser Ala Gly Ser Gly His His His
515 520 525

His His His
530

<210> SEQ ID NO 40
<211> LENGTH: 529
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Met Glu Leu Leu Ile Leu Lys Ala Asn Ala Ile Thr Thr Ile Leu Thr
1 5 10 15

-continued

```
Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Ala Ser Ala Ile Ala Ser Gly Val
    130                 135                 140

Ala Val Ser Lys Val Leu His Leu Glu Gly Glu Val Asn Lys Ile Lys
145                 150                 155                 160

Ser Ala Leu Leu Ser Thr Asn Lys Ala Val Val Ser Leu Ser Asn Gly
                165                 170                 175

Val Ser Val Leu Thr Ser Lys Val Leu Asp Leu Lys Asn Tyr Ile Asp
            180                 185                 190

Lys Gln Leu Leu Pro Ile Val Asn Lys Gln Ser Cys Ser Ile Ser Asn
        195                 200                 205

Ile Glu Thr Val Ile Glu Phe Gln Gln Lys Asn Asn Arg Leu Leu Glu
    210                 215                 220

Ile Thr Arg Glu Arg Ser Val Asn Ala Gly Val Thr Thr Pro Val Ser
225                 230                 235                 240

Thr Tyr Met Leu Thr Asn Ser Glu Leu Leu Ser Leu Ile Asn Asp Met
                245                 250                 255

Pro Ile Thr Asn Asp Gln Lys Lys Leu Met Ser Asn Asn Val Gln Ile
            260                 265                 270

Val Arg Gln Gln Ser Tyr Ser Ile Met Ser Ile Ile Lys Glu Glu Val
        275                 280                 285

Leu Ala Tyr Val Val Gln Leu Pro Leu Tyr Gly Val Ile Asp Thr Pro
    290                 295                 300

Cys Trp Lys Leu His Thr Ser Pro Leu Cys Thr Thr Asn Thr Lys Glu
305                 310                 315                 320

Gly Ser Asn Ile Cys Leu Thr Arg Thr Asp Arg Gly Trp Tyr Cys Asp
                325                 330                 335

Asn Ala Gly Ser Val Ser Phe Phe Pro Gln Ala Glu Thr Cys Lys Val
            340                 345                 350

Gln Ser Asn Arg Val Phe Cys Asp Thr Met Asn Ser Leu Thr Leu Pro
        355                 360                 365

Ser Glu Val Asn Leu Cys Asn Val Asp Ile Phe Asn Pro Lys Tyr Asp
    370                 375                 380

Cys Lys Ile Met Thr Ser Lys Thr Asp Val Ser Ser Ser Val Ile Thr
385                 390                 395                 400

Ser Leu Gly Ala Ile Val Ser Cys Tyr Gly Lys Thr Lys Cys Thr Ala
                405                 410                 415

Ser Asn Lys Asn Arg Gly Ile Ile Lys Thr Phe Ser Asn Gly Cys Asp
            420                 425                 430
```

-continued

```
Tyr Val Ser Asn Lys Gly Val Asp Thr Val Ser Val Gly Asn Thr Leu
        435                 440                 445

Tyr Tyr Val Asn Lys Gln Glu Gly Lys Ser Leu Tyr Val Lys Gly Glu
    450                 455                 460

Pro Ile Ile Asn Phe Tyr Asp Pro Leu Val Phe Pro Ser Asp Glu Phe
465                 470                 475                 480

Asp Ala Ser Ile Ser Gln Val Asn Glu Lys Ile Asn Gln Ser Leu Ala
                485                 490                 495

Phe Ile Arg Lys Ser Asp Glu Leu Leu His Asn Val Asn Ala Gly Lys
            500                 505                 510

Ser Thr Thr Asn Gly Gly Ser Ala Gly Ser Gly His His His His His
        515                 520                 525

His
```